(12) United States Patent
Zheng

(10) Patent No.: US 10,526,304 B2
(45) Date of Patent: Jan. 7, 2020

(54) NEBIVOLOL SYNTHESIS METHOD AND INTERMEDIATE COMPOUND THEREOF

(71) Applicant: ZHEJIANG AUSUN PHARMACEUTICAL CO., LTD., Zhejiang (CN)

(72) Inventor: Zhiguo Zheng, Zhejiang (CN)

(73) Assignee: ZHEJIANG AUSUN PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 15/575,171

(22) PCT Filed: May 19, 2015

(86) PCT No.: PCT/CN2015/079329
§ 371 (c)(1),
(2) Date: Nov. 17, 2017

(87) PCT Pub. No.: WO2016/183809
PCT Pub. Date: Nov. 24, 2016

(65) Prior Publication Data
US 2018/0141926 A1    May 24, 2018

(51) Int. Cl.
| | |
|---|---|
| *C07D 311/76* | (2006.01) |
| *C07C 43/295* | (2006.01) |
| *C07D 311/58* | (2006.01) |
| *C07C 41/18* | (2006.01) |
| *C07C 41/20* | (2006.01) |
| *C07C 41/22* | (2006.01) |
| *C07C 41/30* | (2006.01) |
| *C07C 43/225* | (2006.01) |
| *C07C 43/23* | (2006.01) |
| *C07F 7/08* | (2006.01) |
| *C07D 301/14* | (2006.01) |
| *C07D 301/19* | (2006.01) |
| *C07D 303/22* | (2006.01) |
| *A61P 9/08* | (2006.01) |
| *A61P 9/12* | (2006.01) |
| *A61K 31/353* | (2006.01) |
| *C07D 303/36* | (2006.01) |

(52) U.S. Cl.
CPC .......... *C07D 311/76* (2013.01); *A61K 31/353* (2013.01); *A61P 9/08* (2018.01); *A61P 9/12* (2018.01); *C07C 41/18* (2013.01); *C07C 41/20* (2013.01); *C07C 41/22* (2013.01); *C07C 41/30* (2013.01); *C07C 43/225* (2013.01); *C07C 43/23* (2013.01); *C07C 43/295* (2013.01); *C07D 301/14* (2013.01); *C07D 301/19* (2013.01); *C07D 303/22* (2013.01); *C07D 303/36* (2013.01); *C07D 311/58* (2013.01); *C07F 7/08* (2013.01)

(58) Field of Classification Search
CPC .......................... C07D 311/76; C07C 43/295
See application file for complete search history.

(56) References Cited

U.S. PATENT DOCUMENTS

| | | | |
|---|---|---|---|
| 6,545,040 B1 | 4/2003 | Xhonneux et al. | |
| 2011/0250454 A1 | 10/2011 | Haldar et al. | |

FOREIGN PATENT DOCUMENTS

| | | |
|---|---|---|
| CN | 1834093 | 9/2006 |
| CN | 1978442 | 6/2007 |
| CN | 101243062 | 8/2008 |
| CN | 101463024 | 6/2009 |
| CN | 101541791 | 9/2009 |
| CN | 101553485 | 10/2009 |
| CN | 102344431 | 2/2012 |
| CN | 102816141 | 12/2012 |
| CN | 102858759 | 1/2013 |
| CN | 103833717 | 6/2014 |
| CN | 104650022 | 5/2015 |
| DE | 10 2014 107 132 | 11/2015 |
| EP | 0145067 | 6/1985 |
| EP | 0334429 | 9/1989 |
| WO | WO 2007/009143 | 1/2007 |
| WO | WO 2008/064826 | 6/2008 |
| WO | WO 2008/064827 | 6/2008 |
| WO | WO 2009/082913 | 7/2009 |
| WO | WO 2011/098474 | 8/2011 |
| WO | WO 2012/104659 A1 | 8/2012 |
| WO | WO 2013/018053 A1 | 2/2013 |
| WO | WO 2016/183809 | 11/2016 |

OTHER PUBLICATIONS

International Search Report of International Application No. PCT/CN2015/079329, dated Feb. 25, 2016, (3 pages).
Trost et al., "Synthesis of Chiral Chromans by the Pd-Catalyzed Asymmetric Allylic Alkylation (AAA): Scope, Mechanism, and Applications", J. Am. Chem. Soc., vol. 126(38), p. 11966-11983, (2004).
CAS Registry No. 1613244-24-8.
CAS Registry No. 303176-39-8.
Chandrasekhar et al., "Enantioselective Total Synthesis of the Antihypertensive Agent (S, R,R,R)-Nebivolol", Tetrahedron, vol. 56(34), p. 6339-6344, (2000).
Chinese Journal of Organic Chemistry vol. 28, p. 511-514, (2008). Zhang, Qingshan et al., "Asymmetric Synthesis of Nebivolol Intermidiate", Journal of Beijing Institute of Technology, vol. 25, No. 6, p. 546-550, (2005).
Dinda, S.K. et al., "Application of Phenolate Ion Mediated Intramolecular Epoxide Ring Opening in the Enantioselective Synthesis of Functionalized 2,3-Dihydrobenzofurans and 1-Benzopyrans[1]," *Synthesis*, 2009, 11:1886-1896.

*Primary Examiner* — Noble E Jarrell
(74) *Attorney, Agent, or Firm* — Hoxie & Associates LLC

(57) ABSTRACT

The present invention relates to nebivolol synthesis method and intermediate compound thereof. Specifically, the present invention relates to a method for synthesizing nebivolol, intermediate compound thereof, and a method for preparing the intermediate compound.

16 Claims, No Drawings

NEBIVOLOL SYNTHESIS METHOD AND INTERMEDIATE COMPOUND THEREOF

CROSS REFERENCE TO RELATED APPLICATIONS

This application is a United States Application under 35 U.S.C. 371 claiming benefit of PCT Application No. PCT/CN2015/079329, filed on May 19, 2015, the contents of which are incorporated herein by reference.

TECHNICAL FIELD

The present invention relates to a process for synthesis of medicine and intermediate compounds thereof. In particular, the present invention relates to a process for synthesis of Nebivolol, intermediate compounds thereof, and a process for preparation of the intermediate compounds.

BACKGROUND ART

Nebivolol hydrochloride, with the chemical name of (+/−)-di[2-(6-fluoro-dihydrobenzopyran-2-yl)-2-hydroxy-ethyl]amine (Formula I) hydrochloride, is a highly selective third-generation β-receptor blocker developed by Johnson & Johnson that also has vasodilation effect. It is primarily used for the treatment of mild to moderate hypertension, angina pectoris and congestive heart failure. The Nebivolol hydrochloride clinically used is a mixture of equal amounts of the dextroisomer (Formula Ia) and the levoisomer (Formula Ib), i.e., its racemate (Formula I). The effect of Nebivolol hydrochloride as blocker on β-receptor is mainly derived from the dextroisomer, but other effects depend on the presence of both the dextroisomer and the levoisomer.

The relative configuration of Nebivolol is as follows:

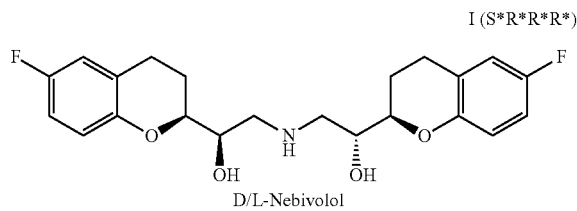 [SMILES: O[C@H](CNC[C@@H](O)[C@H]1CCc2cc(F)ccc2O1)[C@@H]1CCc2cc(F)ccc2O1]

D/L-Nebivolol wherein I (S*R*R*R*) represents racemate, which is a racemic mixture consisting of equimolar amounts of D-Nebivolol Ia (SRRR) and its enantiomer L-Nebivolol Ib (RSSS) as shown below.

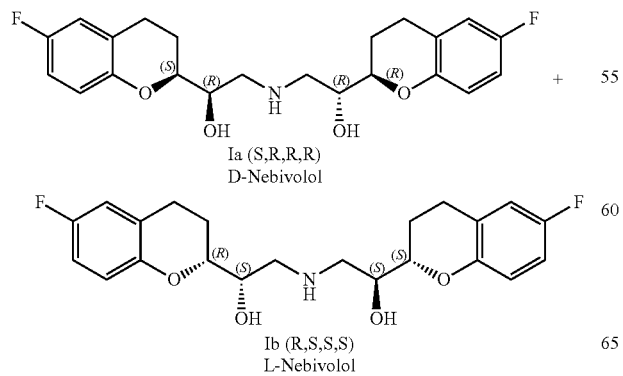

Both of the levoisomer and the dextroisomer of Nebivolol have important biological activity, the levoisomer has endothelial cell-dependent vasodilation effect, and the dextroisomer has a strong β1-receptor blockade effect. A mixture of the levoisomer and dextroisomer is clinically used now, which allows the activities of the two isomers to be synergistic, ensuring that Nebivolol has a unique advantage in addition to the above β-receptor blockade effect: β1-receptor is selectively antagonized by enhancing release of NO, resulting in vasodilation. It does not affect β2 receptor, and does not cause contraction of bronchial smooth muscle and vascular smooth muscle. Therefore, in view of the important pharmacological value of Nebivolol, it is of great economic and social benefits to develop a process for the preparation of Nebivolol and its optical isomers, which is highly efficient, low-cost, and meets the requirements of industrialization.

The molecular structure of Nebivolol contains four chiral carbon atoms as marked below, wherein isomer S*R*R*R* is the Nebivolol used clinically, and it is represented as racemic mixture containing equimolar amounts of D-isomer with absolute configuration SRRR and its enantiomer L-isomer with absolute configuration RSSS.

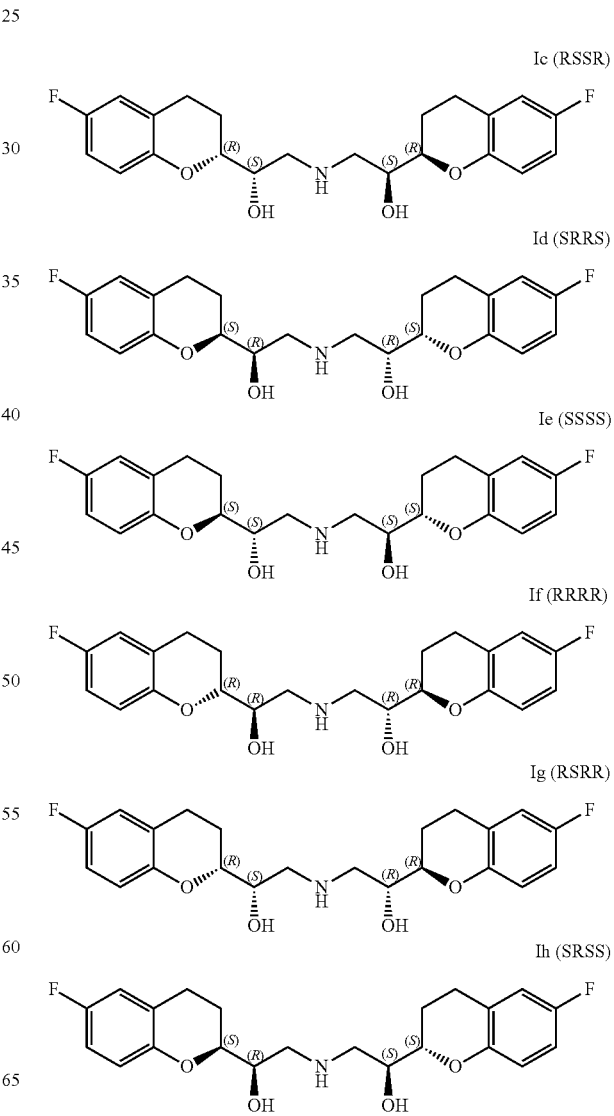

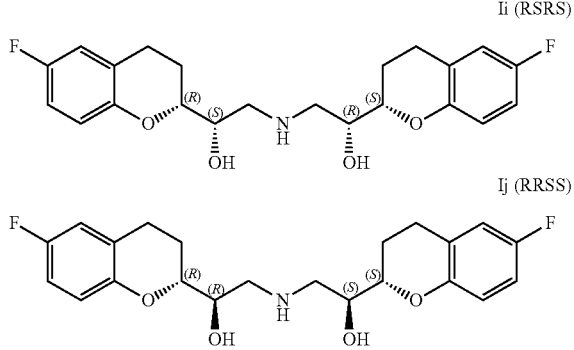

Nebivolol is structurally characterized in having certain symmetry. Each of the left and right parts of the molecule has a structural unit of (6-fluoro-benzopyranyl)ethane-2-ol with different configurations. In the left part (part A), the hydroxyl group and the oxygen in the pyran ring is in cis-form, and in the right part (part B), they are in trans-form, and the units in the two parts are linked by a nitrogen atom.

In the prior art literatures, synthesis of Nebivolol is mainly based on the symmetry of its molecule, the parts A and B are synthesized respectively, and then coupled with benzylamine. After separation, purification and deprotection, Nebivolol is achieved.

Specifically, the existing methods for preparation of Nebivolol mainly include the following:

(1) Using the racemic intermediates as raw materials, the fragments in the left and right parts with the relative configurations in Nebivolol molecule are constructed respectively, and then subjected to cross-coupling reaction to prepare the desired product;

The key point of this method is how to prepare the two fragments A and B with high diastereomeric purity in the desired configuration, otherwise the mixture containing the above ten isomers will be obtained after coupling reaction.

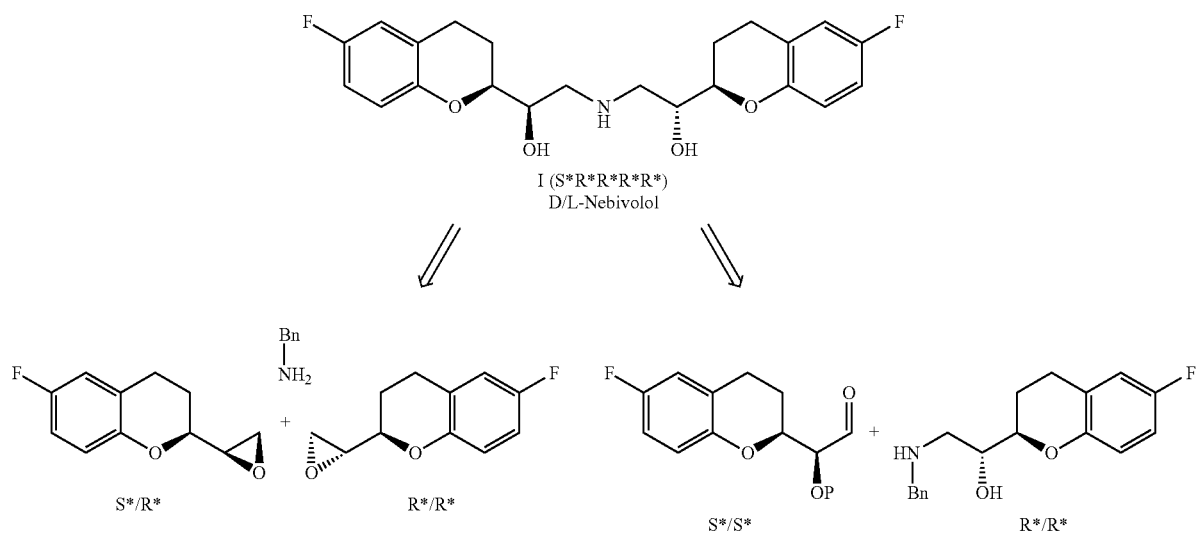

The intermediate compounds obtained by coupling two fragments A and B with the desired configurations contain two pairs of diastereoisomers and need to be isolated by recrystallization to give the intermediates with the desired configuration:

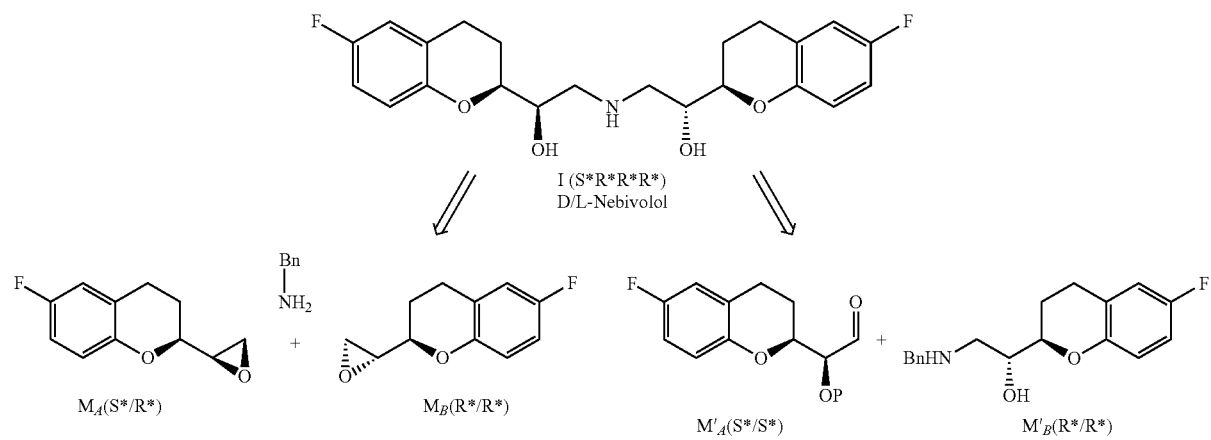

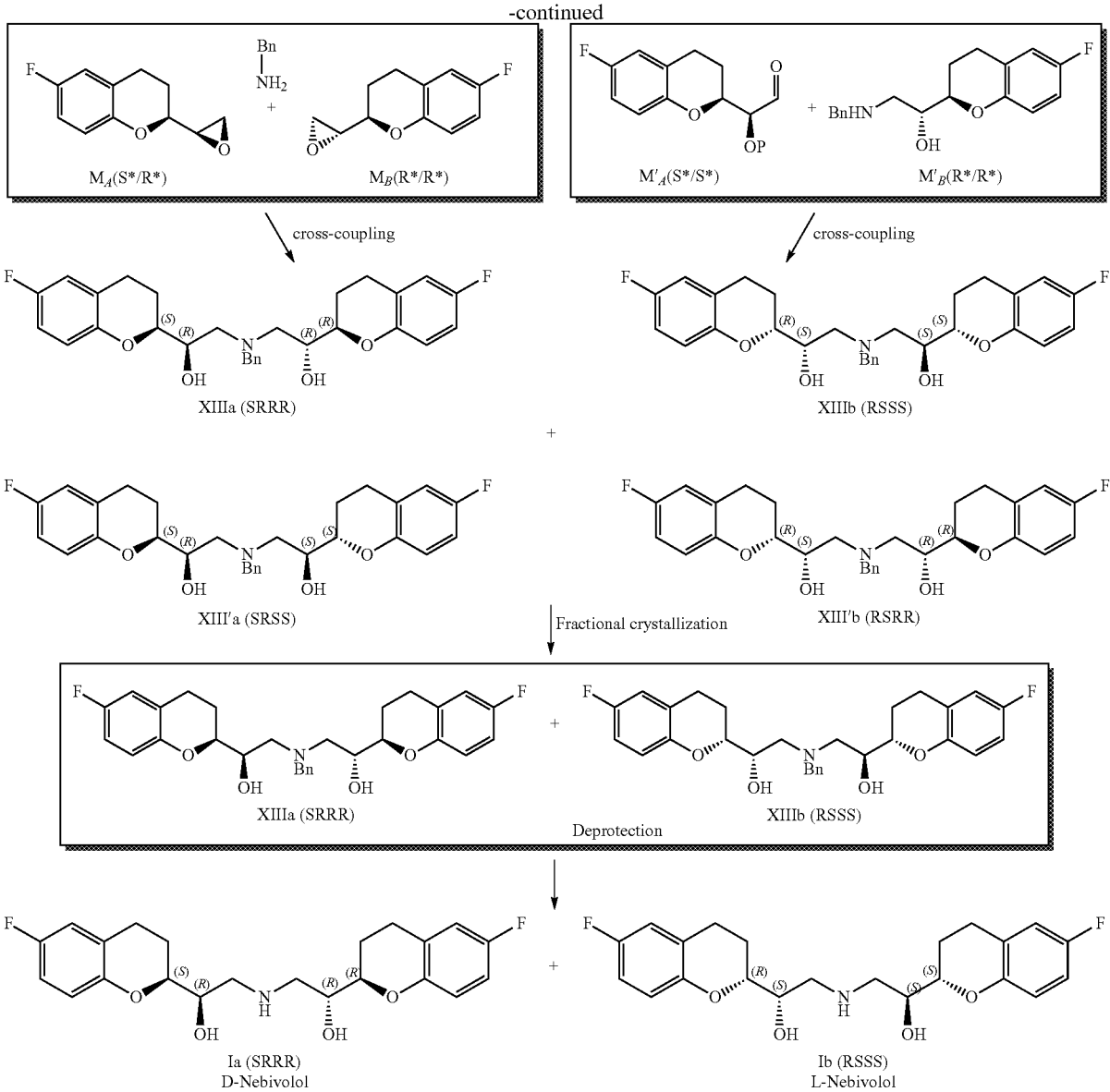

Janssen's patent EP 145067 discloses the following synthetic process, characterized in that the chroman aldehyde and trimethylsulfoxonium iodide are reacted in the presence of sodium hydride to give a pair of unequal amounts of diastereoisomers, i.e., the epoxide intermediates $M_A$ (S*R*) and $M_B$ (R*R*). Epoxide intermediates $M_A$ (S*R*) and $M_B$ (R*R*) can be separated by chromatography and then be the key intermediates for synthesis of Nebivolol, followed by cross-coupling reaction with benzylamine to give a mixture of SRRR/RSSS and SRSS/RSRR as follows:

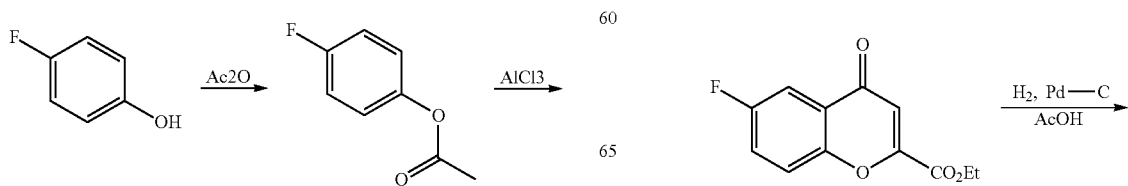

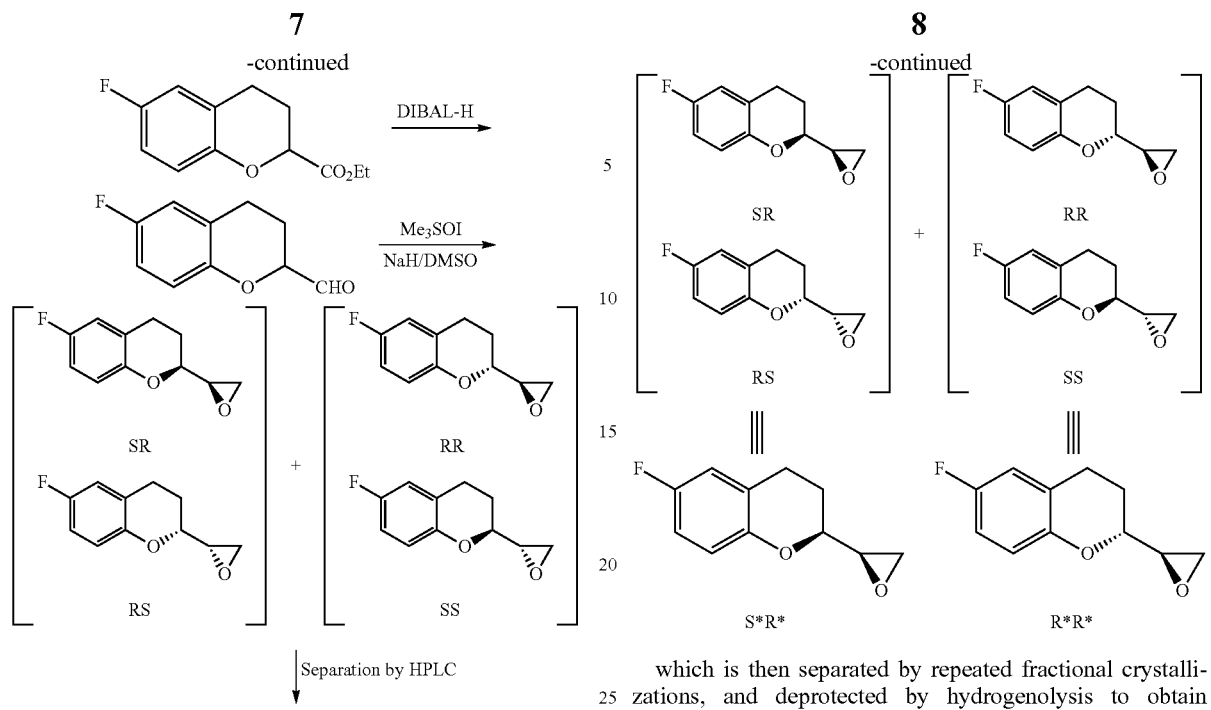
which is then separated by repeated fractional crystallizations, and deprotected by hydrogenolysis to obtain S*R*R*R*-Nebivolol, as follows:
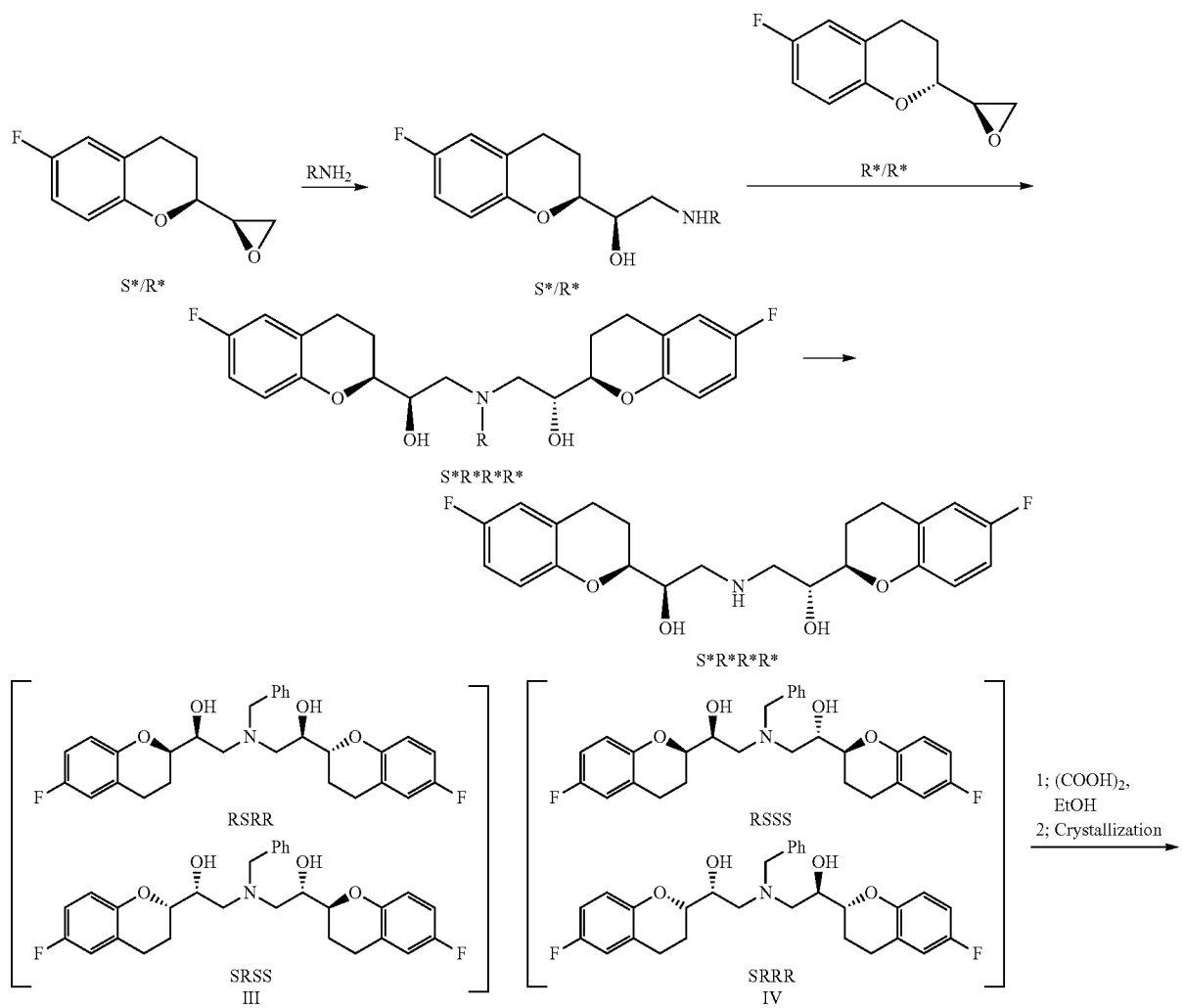

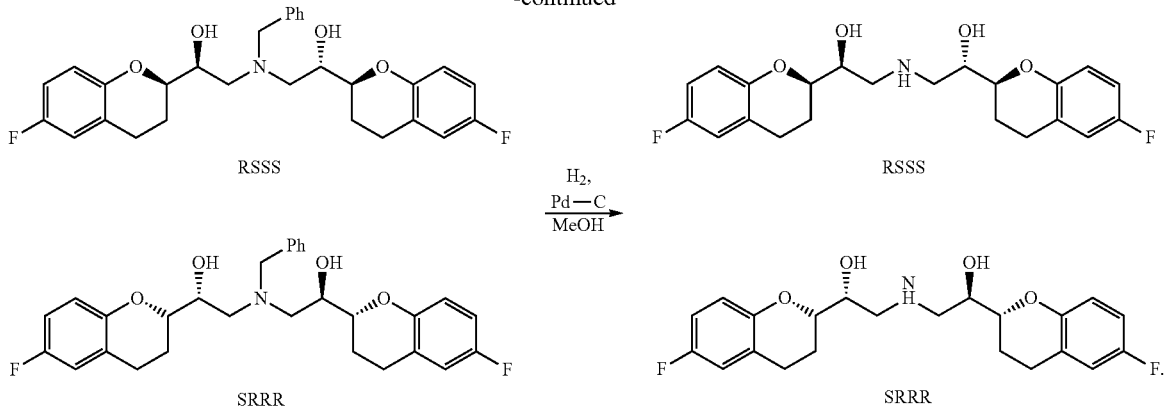

Although the above-mentioned preparation method is widely used in the industry now, the main problem of this method is that the key intermediates need to be separated by column chromatography, thus it is of high cost to use in large-scale production. In addition, the reaction conditions for preparing the epoxides from unstable chroman aldehyde are harsh, the yield is low and the reagents used are expensive.

(2) Cyanide Derivative Method of the Patent WO2007/009143 (CN101243062)

The method is carried out by reaction of racemic chroman aldehyde with sodium bisulfite and sodium cyanide to give nitrile alcohol intermediates, which are then separated by column chromatography to yield a pair of cis- and trans-nitrile alcohol diastereomers.

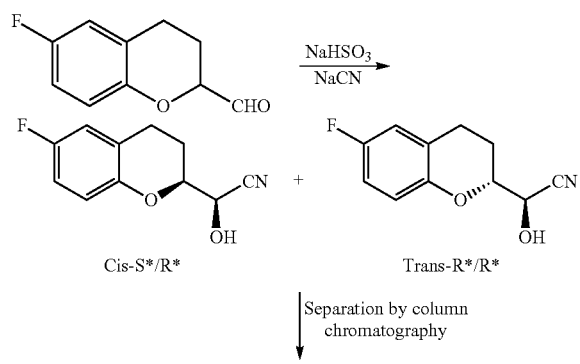

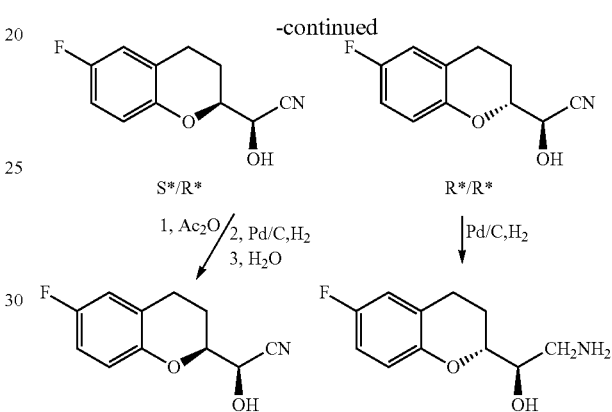

The cis-nitrile alcohol intermediate is acetylated and then subjected to catalytic hydrogenation to convert to the corresponding aldehyde, which is then hydrolyzed to give the corresponding aldol intermediate.

The trans-nitrile alcohol intermediate is then catalytically hydrogenated to the corresponding alcohol amine, which is reacted with benzoyl chloride to give the amide, followed by reduction to give the benzylamine intermediate, which is finally condensed with the aldol intermediate to give a pair of diastereoisomers (four isomers) as crude Nebivolol. The crude Nebivolol is then converted to the salt with hydrochloric acid. After recrystallizations from ethanol are repeated to remove another pair of isomers, racemic Nebivolol is obtained.

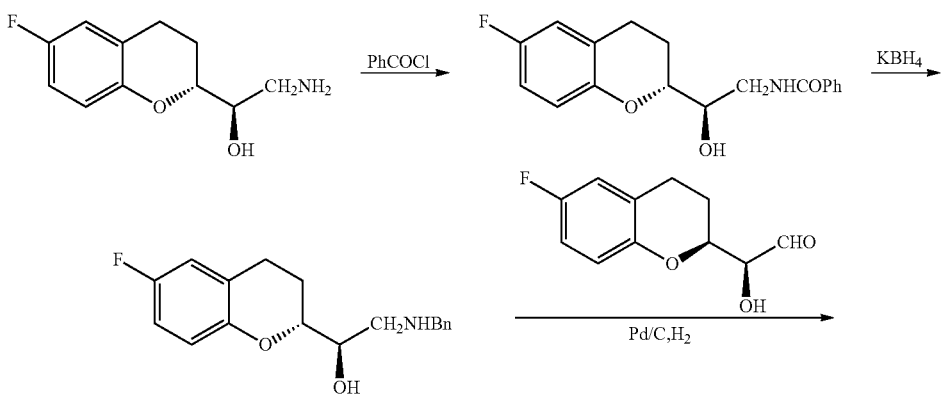

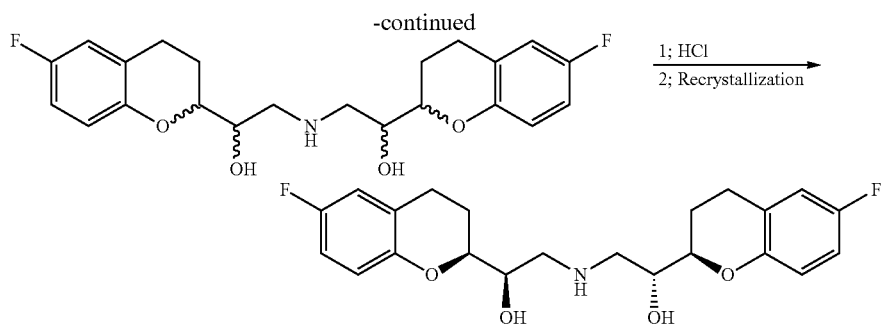

The problem of this method is similar to that of the previous method, that is, the reaction conditions are harsh, and the separation of the key intermediates needs column chromatography, thus it is difficult to apply this method to large-scale industrial production.

(3) D-Nebivolol and L-Nebivolol are Synthesized Respectively, and the D-Isomer and L-Isomer are Mixed in Equal Amounts to Give Racemic Nebivolol. The Methods for Synthesis of Optical Isomers of Nebivolol Mainly Include the Following:

Patents EP0334429 and U.S. Pat. No. 6,545,040 disclose the chroman carboxylic acid is resolved to the corresponding S-chroman carboxylic acid and R-chroman carboxylic acid, and the following procedure is used to synthesize L-Nebivolol,

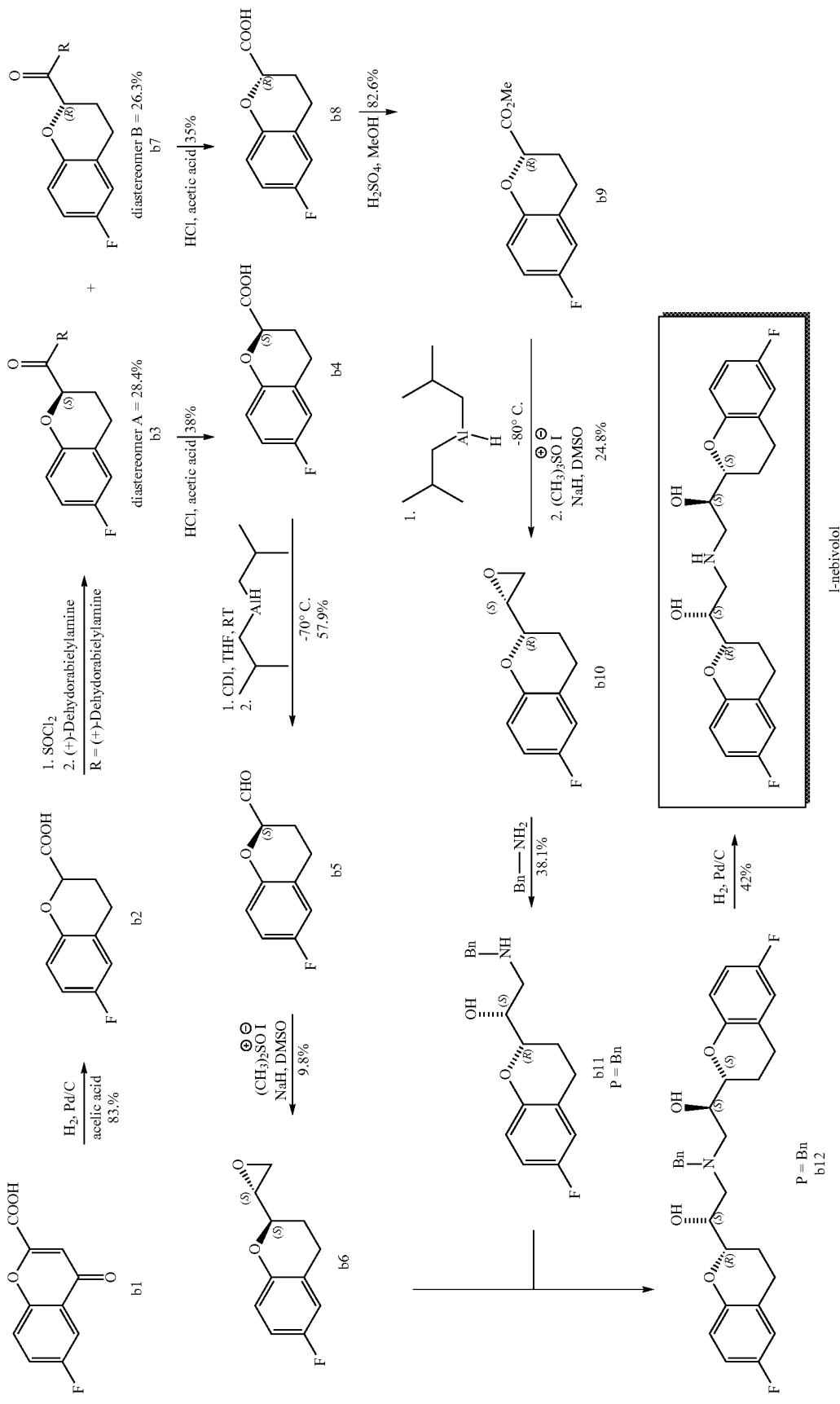

The above method is still a method derived from Janssen patent EP145067. Although an optically pure chroman carboxylic acid obtained by chiral separation is used, the subsequent step of forming an epoxide intermediate using trimethylsulfoxonium iodide in the presence of sodium hydride still produces two diastereoisomers in unequal amounts, thus chromatographic separation is likewise required in order to obtain two optically pure epoxide intermediates.

The literatures (Tetrahedron, 56, 6339-6344, 2000 and Chinese Journal of Organic Chemistry 28, 511-514, 2008) have reported the synthesis using 1-(6-fluoro-benzopyranyl)ethane-1,2-diol as key intermediate, in which Sharpless asymmetric epoxidation reaction is utilized. The synthetic route is as follows

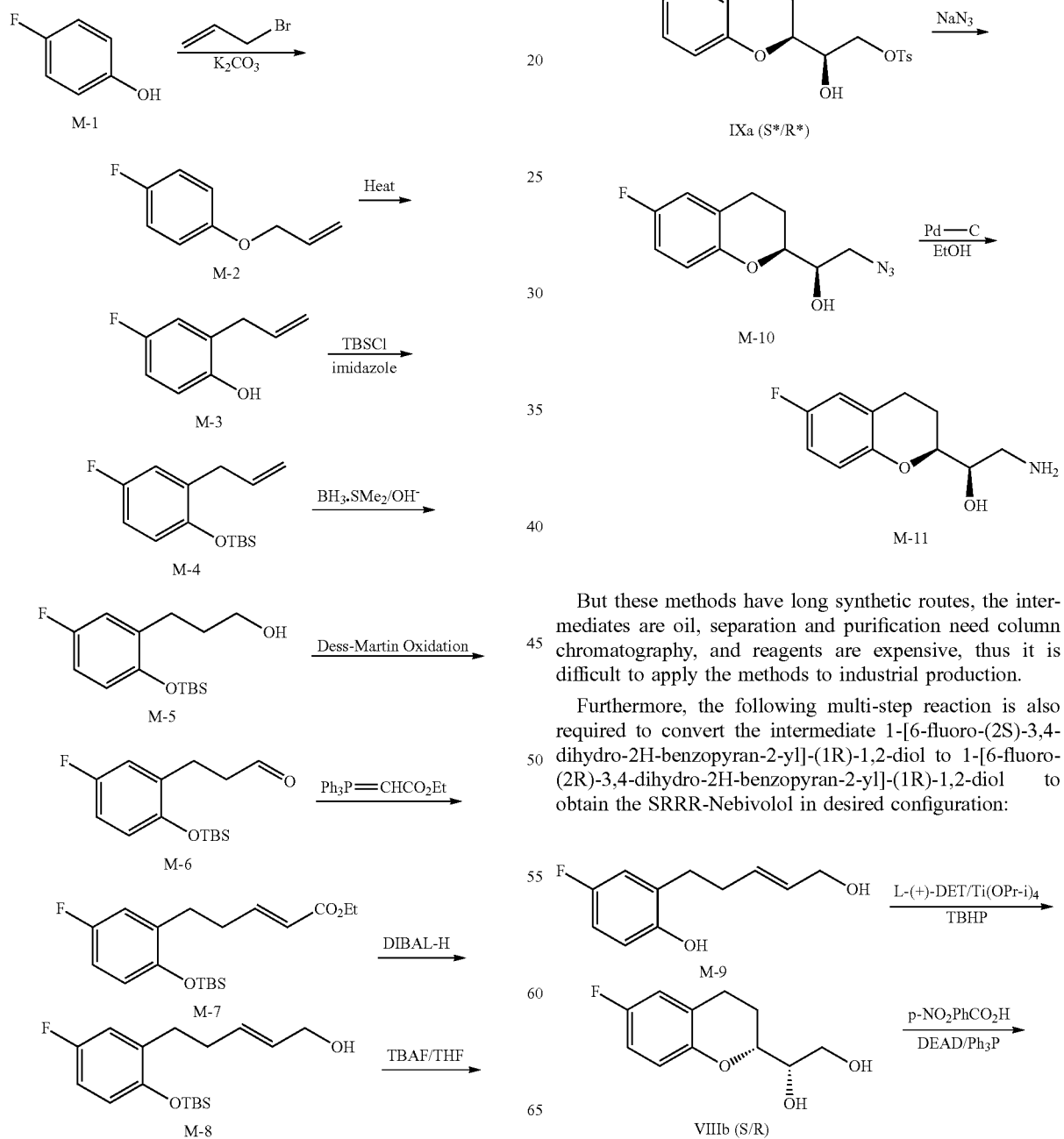

But these methods have long synthetic routes, the intermediates are oil, separation and purification need column chromatography, and reagents are expensive, thus it is difficult to apply the methods to industrial production.

Furthermore, the following multi-step reaction is also required to convert the intermediate 1-[6-fluoro-(2S)-3,4-dihydro-2H-benzopyran-2-yl]-(1R)-1,2-diol to 1-[6-fluoro-(2R)-3,4-dihydro-2H-benzopyran-2-yl]-(1R)-1,2-diol to obtain the SRRR-Nebivolol in desired configuration:

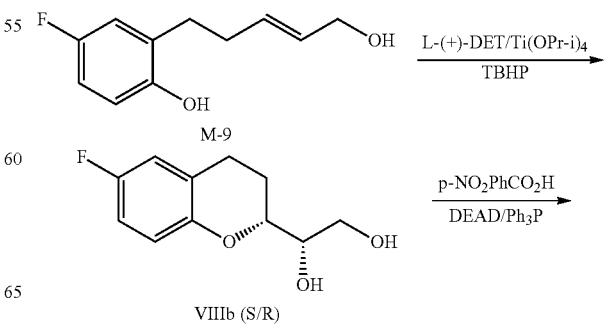

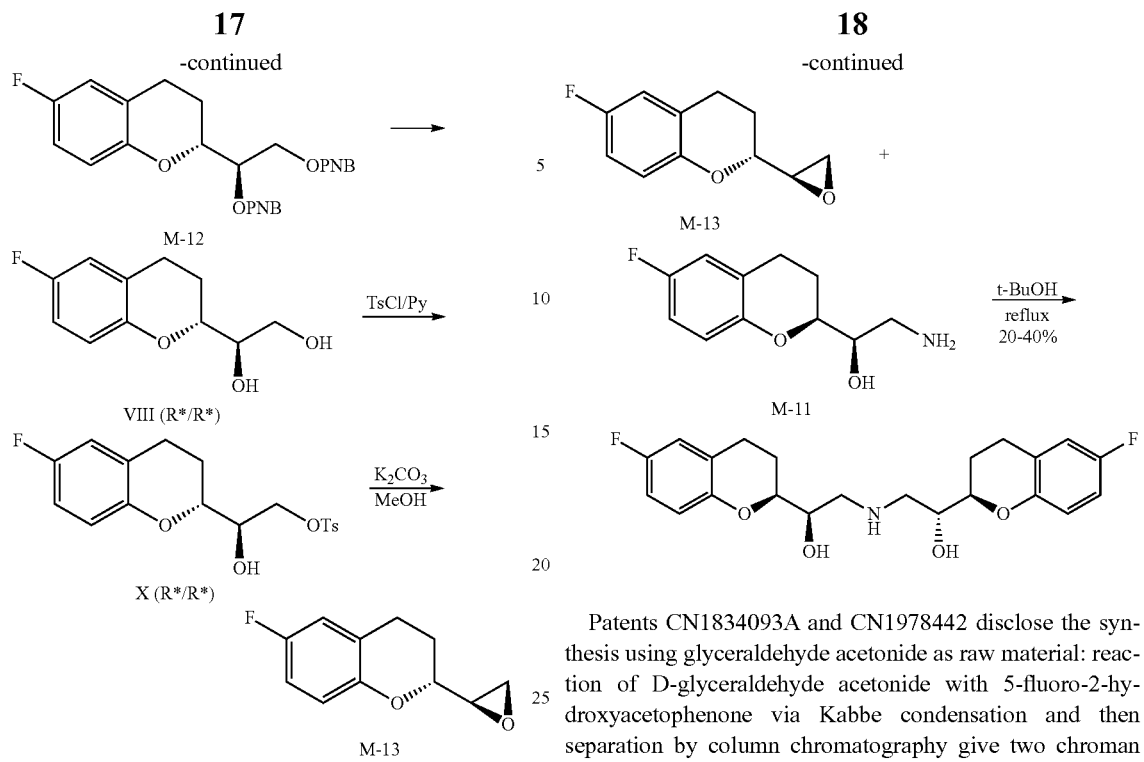
Patents CN1834093A and CN1978442 disclose the synthesis using glyceraldehyde acetonide as raw material: reaction of D-glyceraldehyde acetonide with 5-fluoro-2-hydroxyacetophenone via Kabbe condensation and then separation by column chromatography give two chroman diol isomers (S,R) and (R, R).
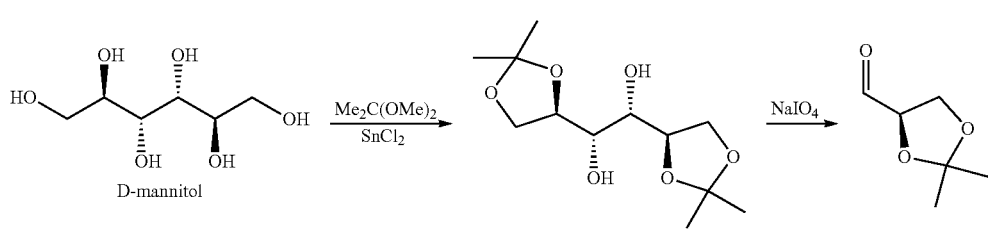
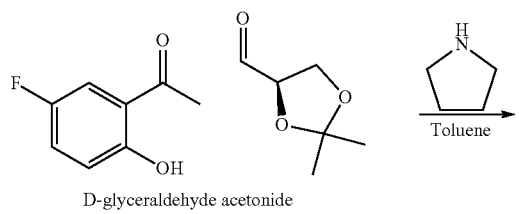
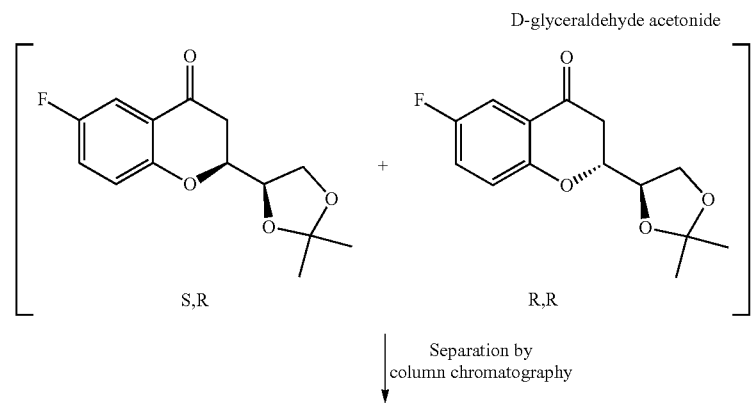

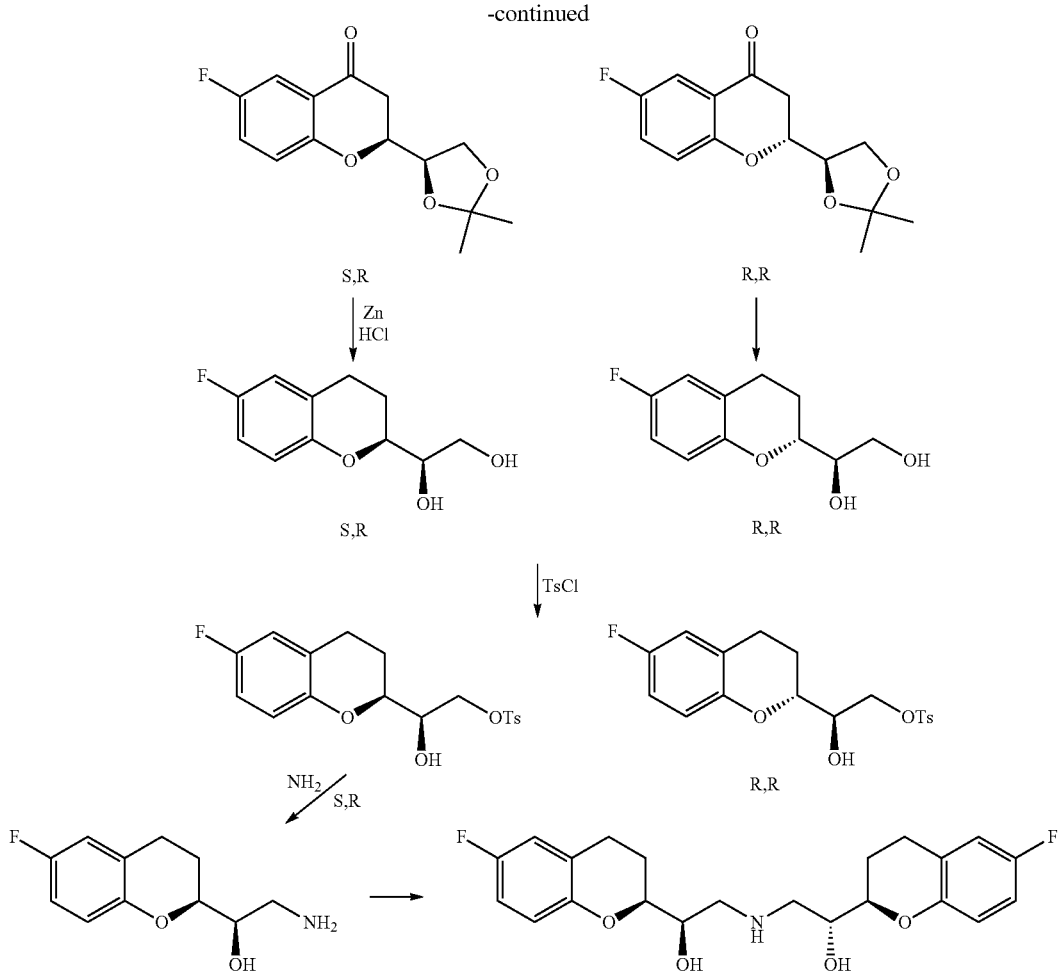

The optically active dextro-rotatory SRRR-Nebivolol can be obtained by selectively sulfonylating the two chroman diols (S,R) and (R,R) isomers with p-toluenesulfonyl chloride, respectively, followed by amination.

In summary, according to the prior art literature to date, it can be found that Nebivolol synthesis still has many technical defects. For example, Janssen's method, although has shorter synthetic route, requires separation of two diastereomeric epoxide intermediates by preparative HPLC, while other methods often face to more synthetic steps and the issue of separating isomers. Therefore, there is a need to develop a highly efficient, low-cost, new method for preparation of Nebivolol and its optical isomers, which is consistent with the requirements of industrialization.

Contents of the Invention

Throughout the invention, the following terms have the meanings as indicated below.

The term "alkyl", whether it is used alone or in combination with other groups, represents a straight or branched monovalent saturated hydrocarbon group consisting of carbon atom and hydrogen atom. "$C_{1-6}$ alkyl" represents straight or branched alkyl having 1-6 carbon atoms, such as methyl, ethyl, n-propyl, isopropyl, n-butyl, sec-butyl, tert-butyl, and n-hexyl.

The term "alkylene", whether it is used alone or in combination with other groups, represents a straight or branched divalent saturated hydrocarbon group consisting of carbon atom and hydrogen atom. "$C_{1-6}$ alkylene" represents straight or branched alkylene having 1-6 carbon atoms, such as methylene, ethylene, and the like.

The term "alkoxy", whether it is used alone or in combination with other groups, represents group $R^A$—O—, wherein $R^A$ represents alkyl as defined above. "$C_{1-6}$ alkoxy" represents group $R^A$—O—, wherein $R^A$ represents $C_{1-6}$ alkyl as defined above.

"Halo" or "Halogen" represents fluoro, chloro, bromo or iodo.

"Haloalkyl" represents alkyl as defined above which is substituted with one or more halogens, e.g., trifluoromethyl.

"Nitro" represents —$NO_2$.

"Aryl" represents monocyclic or fused bicyclic aromatic ring containing carbon atoms. "$C_{5-10}$ aryl" represents aryl having 5-10 carbon atoms. For example, $C_{5-10}$ aryl may be phenyl or naphthyl.

"Substituted aryl" represents aryl which is substituted with alkyl, alkoxy, halo, haloalkyl or nitro as defined above.

"Aralkyl" represents alkyl as defined above which is substituted with aryl as defined above.

"Substituted aralkyl" represents aralkyl which is substituted with alkyl, alkoxy, halo, haloalkyl or nitro as defined above.

"Aralkoxy" represents alkoxy as defined above which is substituted with aryl as defined above.

"Substituted aralkoxy" represents aralkoxy which is substituted with alkyl, alkoxy, halo, haloalkyl or nitro as defined above.

In an aspect, the present invention provides a process for preparation of formula III

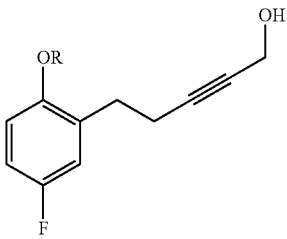

wherein R is hydroxy-protecting group, which is selected from alkyl, haloalkyl, aralkyl, alkoxyalkyl, allyl, or silyl protective group, such as t-BuMe$_2$Si, t-BuPh$_2$Si, (i-Pr)$_3$Si, Et$_3$Si, allyl, methoxymethyl, benzyl or —CH$_2$Ar, wherein Ar is unsubstituted or substituted aryl, such as p-methoxyphenyl or halogen-substituted phenyl, the process comprising the following steps:

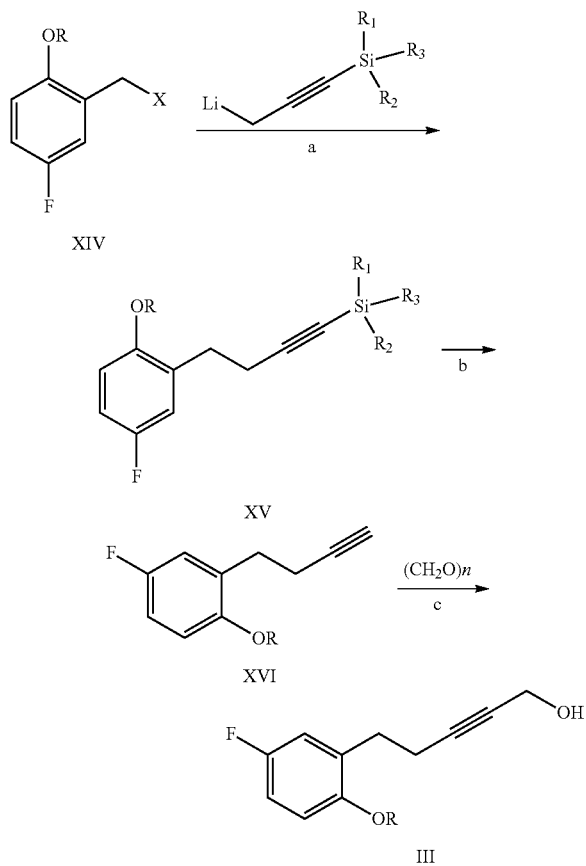

step a): reacting the compound of formula XIV, wherein R is hydroxy-protecting group as described above and X is halogen, with 3-(tri-substituted silyl)-prop-2-yne-1-lithium to give the compound of formula XV, wherein each of R$_1$, R$_2$ and R$_3$ is independently selected from alkyl or aryl, such as methyl, tert-butyl or phenyl;

step b): removing the silyl protective group at the terminal of alkynyl in the compound of formula XV to give the compound of formula XVI, wherein R is defined as above;

step c): reacting the compound of formula XVI with paraformaldehyde in the presence of base or organometallic reagent to give the compound of formula III, wherein R is defined as above; and optionally step d): to the compound of formula III obtained by step c), adding non-polar organic solvent, such as n-hexane, n-heptane, petroleum ether, diethyl ether, isopropyl ether or tert-butyl methyl ether, or a mixture of any two or more of them, stirring at low temperature such as 0° C. to −20° C., followed by crystallization and filtration, to yield the compound of formula III as solid.

In a preferred embodiment, the reaction of step a) is carried out in organic aprotic solvent, such as methyltetrahydrofuran, tetrahydrofuran, dioxane, diethyl ether, tert-butyl methyl ether or toluene, and the reaction temperature is −100° C. to 60° C.

In another preferred embodiment, the reaction of step b) is carried out in the presence of base, acid, or a salt containing fluorine, preferably in the presence of base, said base is selected from alkali metal or alkali earth metal hydroxide or carbonate, such as NaOH, KOH, Na$_2$CO$_3$, K$_2$CO$_3$, the solvent used in the reaction is selected from protic solvent, such as water, methanol, ethanol, or a mixture of any two or more of them, and the reaction temperature is −100° C. to 80° C.

In another preferred embodiment, the base in step c) is selected from metal hydride or organic base, such as NaNH$_2$ or KNH$_2$, the organometallic reagent is selected from BuLi, t-BuLi, s-BuLi, LDA or Grignard reagent, such as MeMgX, EtMgX, BuMgX, i-PrMgX, wherein X is Br, I or Cl, the solvent used in the reaction is organic aprotic solvent, such as tetrahydrofuran, methyltetrahydrofuran, toluene, dioxane, diethyl ether, isopropyl ether, tert-butyl methyl ether, toluene, or a mixture of any two or more of them, and the reaction temperature is −100° C. to 100° C.

In another preferred embodiment, the organic solvent in step d) is organic aprotic solvent, such as n-heptane, n-hexane, petroleum ether, diethyl ether, isopropyl ether, tert-butyl methyl ether, or a mixture of any two or more of them.

In a further preferred embodiment, the reaction of step a) is carried out in organic aprotic solvent, such as methyltetrahydrofuran, tetrahydrofuran, dioxane, diethyl ether, tert-butyl methyl ether or toluene;

the reaction of step b) is carried out in the presence of base, acid, or a salt containing fluorine, preferably in the presence of base, said base is selected from alkali metal or alkali earth metal hydroxide or carbonate, such as NaOH, KOH, Na$_2$CO$_3$, K$_2$CO$_3$, the solvent used in the reaction is selected from protic solvent, such as water, methanol, ethanol, or a mixture of any two or more of them; and the base in step c) is selected from metal hydride or organic base, such as NaNH$_2$ or KNH$_2$, the organometallic reagent is selected from BuLi, t-BuLi, s-BuLi, LDA or Grignard reagent, such as MeMgX, EtMgX, BuMgX, i-PrMgX, wherein X is Br, I or Cl, the solvent used in the reaction is organic aprotic solvent, such as tetrahydrofuran, methyltetrahydrofuran, toluene, dioxane, diethyl ether, isopropyl ether, tert-butyl methyl ether, toluene, or a mixture of any two or more of them.

A skilled person in the art will understand that, in above process for preparation of the compound of formula III, the reaction product of any one of step a) to step c) or d) can be used as starting material to perform subsequent steps described above to prepare the compound of formula III. For example, the compounds of formula (XV) can be used as starting material to perform steps b) to c) or d) described above to prepare the compound of formula III, or the compounds of formula (XVI) can be used as starting material to perform step c) or d) described above to prepare the compound of formula III.

In another aspect, the present invention provides the compound of formula III,

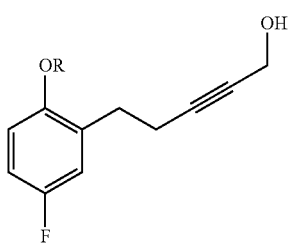

wherein R is hydroxy-protecting group, which is selected from alkyl, haloalkyl, aralkyl, alkoxyalkyl, allyl, or silyl protective group, such as t-BuMe$_2$Si, t-BuPh$_2$Si, (i-Pr)$_3$Si, Et$_3$Si, allyl, methoxymethyl, benzyl or —CH$_2$Ar, wherein Ar is unsubstituted or substituted aryl, such as p-methoxyphenyl or halogen-substituted phenyl.

In another aspect, the present invention provides a process for preparation of racemic Nebivolol of formula I,

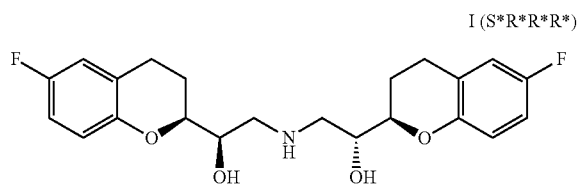 [SMILES: O[C@H](CNC[C@@H](O)[C@H]1CCc2cc(F)ccc2O1)[C@@H]1CCc2cc(F)ccc2O1]

wherein I (S*R*R*R*) represents racemate, which is a racemic mixture consisting of equimolar amounts of D-Nebivolol Ia (SRRR) and the enantiomer thereof L-Nebivolol Ib (RSSS) having the following configurations;

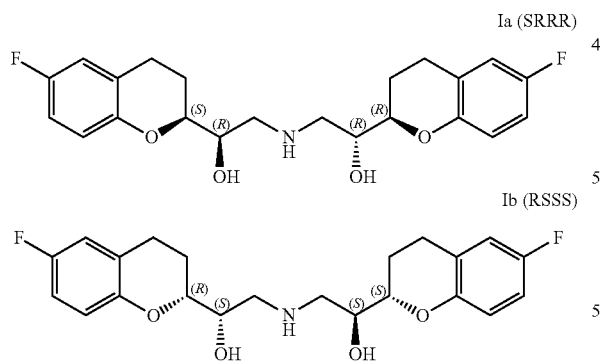

the process comprising the following steps:
1) reducing the compound of formula III with metal composite hydride to give the compound of formula IV1 in trans-configuration;
and optionally the following step: to the resulting compound of formula IV1, adding non-polar organic solvent, such as n-hexane, n-heptane, petroleum ether, diethyl ether, isopropyl ether or tert-butyl methyl ether, or a mixture of any two or more of them, stirring at low temperature such as 0° C. to –20° C., followed by crystallization and filtration, to yield the compound of formula IV1 as solid,

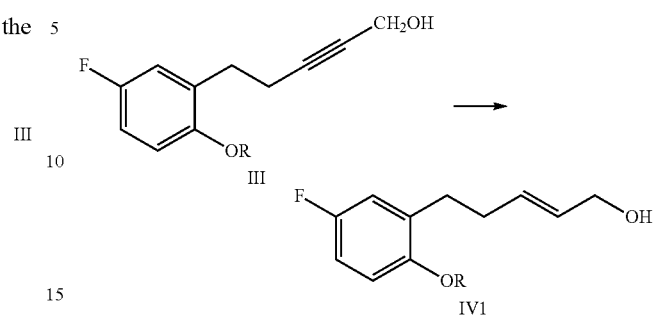

wherein R is hydroxy-protecting group, which is selected from alkyl, haloalkyl, aralkyl, alkoxyalkyl, allyl, or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, 2) reducing the compound of formula III via selective catalytic hydrogenation to give the compound of formula IV2 in cis-configuration
and optionally the following step: to the resulting compound of formula IV2, adding non-polar organic solvent, such as n-hexane, n-heptane, petroleum ether, diethyl ether, isopropyl ether or tert-butyl methyl ether, or a mixture of any two or more of them, stirring at low temperature such as 0° C. to –20° C., followed by crystallization and filtration, to yield the compound of formula IV2 as solid,

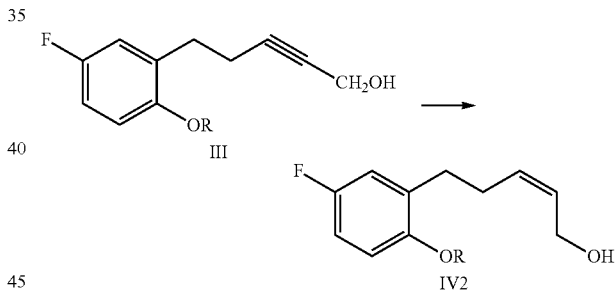

wherein R is defined as above 1),
3) epoxidation of the compound of formula IV1 in trans-configuration and the compound of formula IV2 in cis-configuration in the presence of epoxidating reagent to give epoxide intermediates V and VI, respectively, wherein R is defined as above,

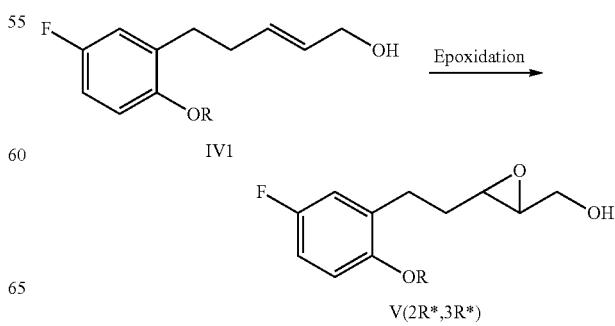

wherein the compound V is racemate, which is a racemic mixture consisting of equimolar amounts of the compound of formula Va and the enantiomer Vb, the relative configuration of which is represented as V (2R*,3R*),

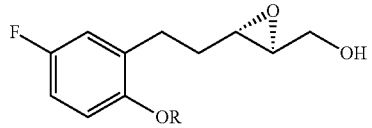

Va(2R,3R)

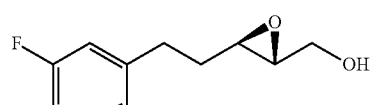

Vb(2S,3S)

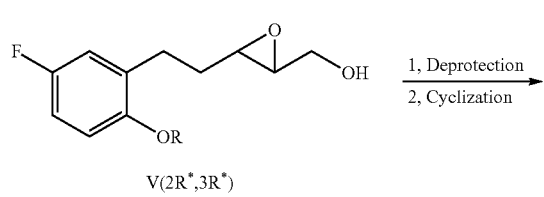

wherein the compound VI is racemate, which is a racemic mixture consisting of equimolar amounts of the compound of formula VIa and the enantiomer VIb, the relative configuration of which is represented as VI (2R*,3S*),

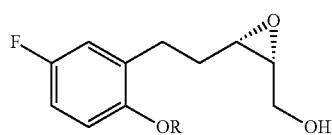

VIa(2R,3S)

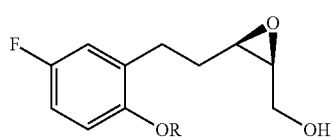

VIb(2S,3R)

4) deprotecting the compound of formula V and the compound of formula VI, followed by cyclization reaction, to give the intermediate compounds of formula VII (S*/R*) and formula VIII (R*/R*), respectively, wherein R is defined as above,

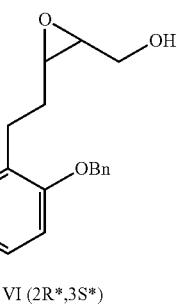

V(2R*,3R*)

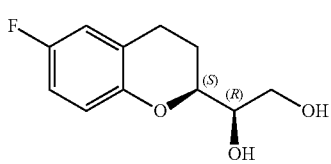

VII(S*/R*)

wherein VII (S*/R*) is racemate, which is a racemic mixture consisting of equimolar amounts of the compound of formula VIIa (S/R) and the enantiomer VIIb (R/S),

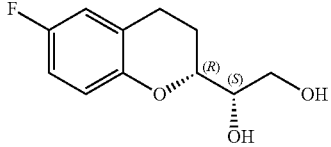

VIIa (S/R)

VIIb (R/S)

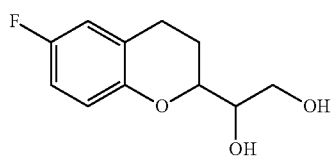

VI (2R*,3S*)

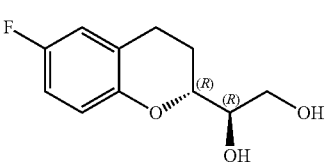

VIII (R*/R*)

wherein VIII (R*/R*) is racemate, which is a racemic mixture consisting of equimolar amounts of the compound of formula VIIIa (R/R) and the enantiomer VIIIb (S/S),

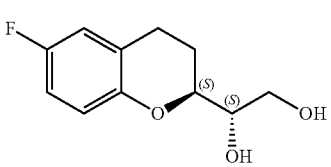

VIIIa (R/R)

VIIIb (S/S)

5) sulfonylating the compounds of formula VII and formula VIII with sulfonyl halide of formula M-SO$_2$X (wherein M is alkyl or substituted or unsubstituted aryl, X is halogen) in the presence of catalyst and base, to give the compounds IX (S*/R*) and X (R*/R*), respectively,

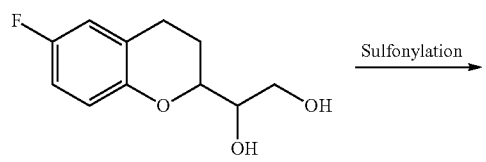

VII(S*/R*)

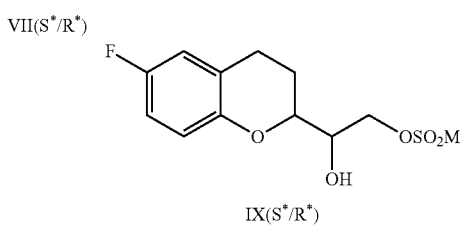

IX(S*/R*)

wherein IX (S*/R*) is racemate, which is a racemic mixture consisting of equimolar amounts of the compound of formula IXa (S/R) and the enantiomer IXb (R/S),

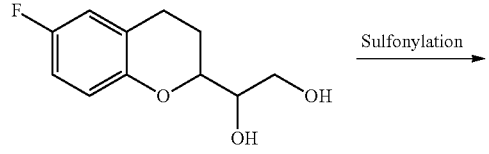

IXa(S/R)

IXb(R/S)

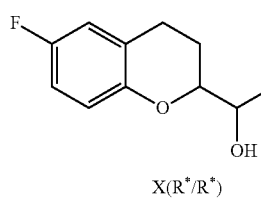

VIII(R*/R*)

X(R*/R*)

wherein X (R*/R*) is racemate, which is a racemic mixture consisting of equimolar amounts of the compound of formula Xa (R/R) and the enantiomer Xb (S/S),

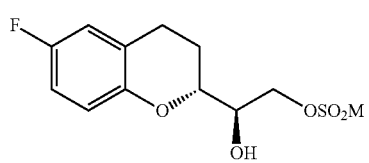

Xa(R/R)

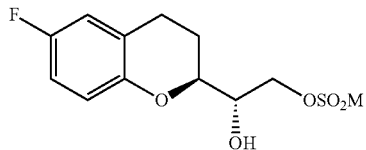

Xb(S/S)

6) reacting the compound of formula IX or X with benzyl amine to perform alkylation of amine, to give the corresponding compound XI or XII;

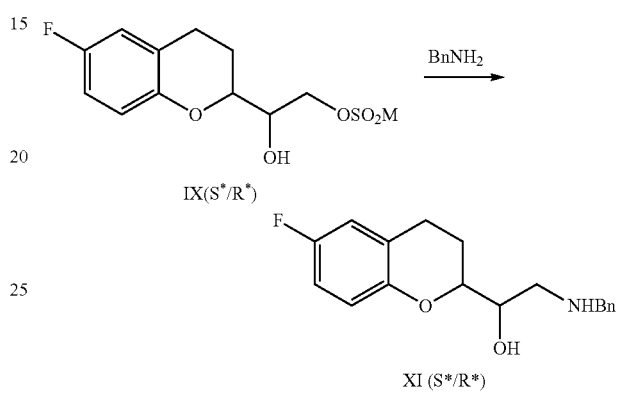

IX(S*/R*)

XI (S*/R*)

wherein XI (S*/R*) is racemate, which is a racemic mixture consisting of equimolar amounts of the compound of formula XIa (S/R) and the enantiomer XIb (R/S),

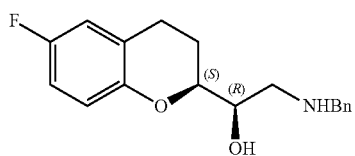

XIa (S/R)

XIb (R/S)

X(R*/R*)

XII(R*/R*)

wherein XII (R*/R*) is racemate, which is a racemic mixture consisting of equimolar amounts of the compound of formula XIIa (R/R) and the enantiomer XIIb (S/S),

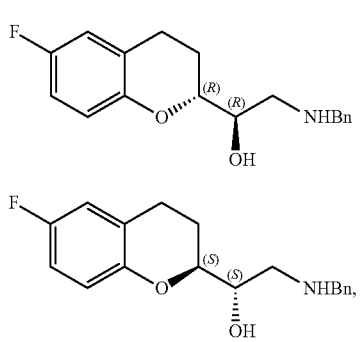

XIIa (R/R)

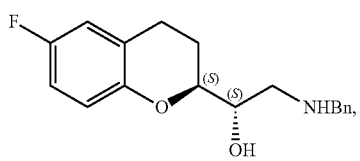

XIIb (S/S)

7) cross-coupling reaction of the intermediate compounds IX (S*/R*) and XII (R*/R*) or the intermediate compounds X (R*/R*) and XI (S*/R*) under basic condition, to give the compounds XIII (S*R*R*R*) and XIII' (S*R*S*S*), wherein the definition of R" is the same as the above definition of M,

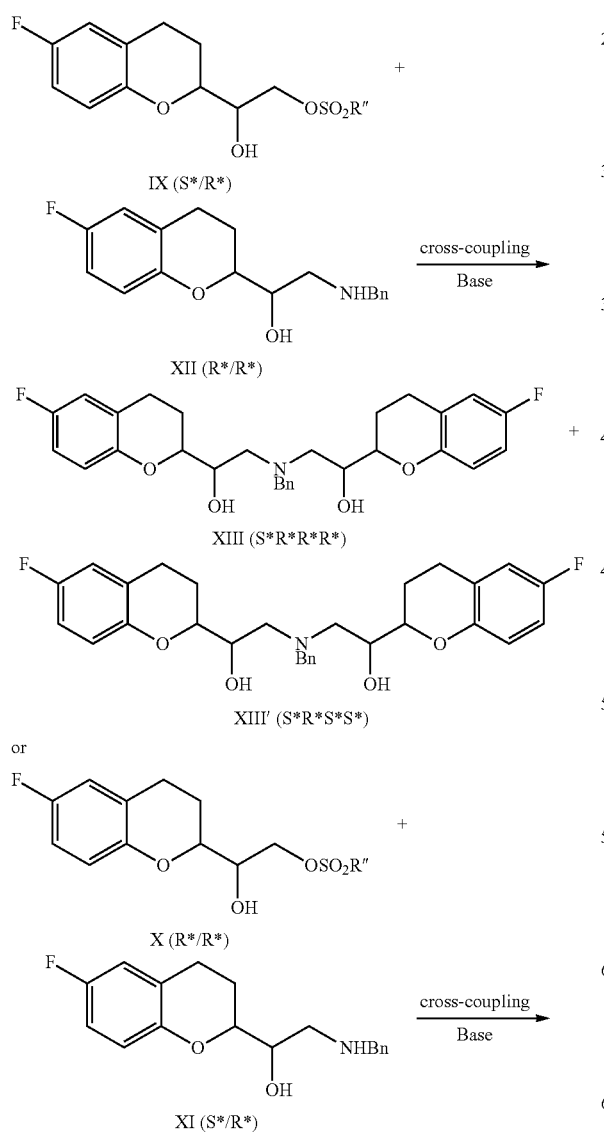

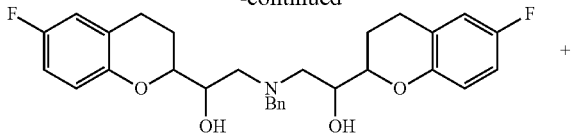

XIII (S*R*R*R*)

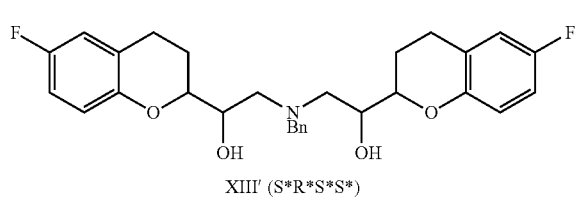

XIII' (S*R*S*S*)

wherein XIII (S*R*R*R*) is racemate, which is a racemic mixture consisting of equimolar amounts of the compound of formula XIIIa (SRRR) and the enantiomer XIIIb (RSSS),

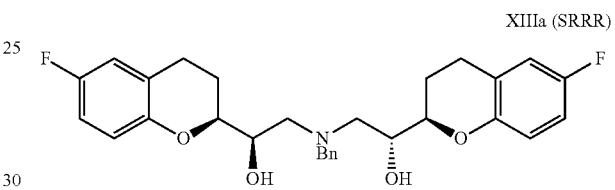

XIIIa (SRRR)

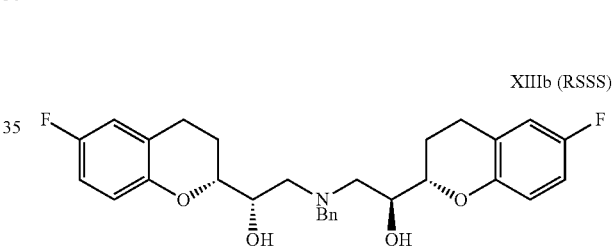

XIIIb (RSSS)

XIII' (S*R*S*S*) is racemate, which is a racemic mixture consisting of equimolar amounts of the compound of formula XIII'a (SRSS) and the enantiomer XIII'b (RSRR),

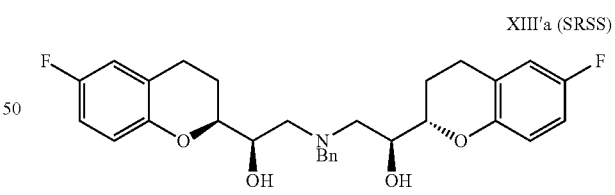

XIII'a (SRSS)

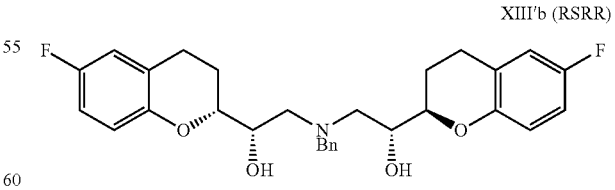

XIII'b (RSRR)

8) Forming salt of a mixture of the compounds of formula XIII and formula XIII', and purifying by recrystallization to remove the isomer XIII' (S*R*S*S*), to give the intermediate compound XIII (S*R*R*R*), 9) deprotecting the intermediate compound XIII (S*R*R*R*) to yield racemic Nebivolol of formula I

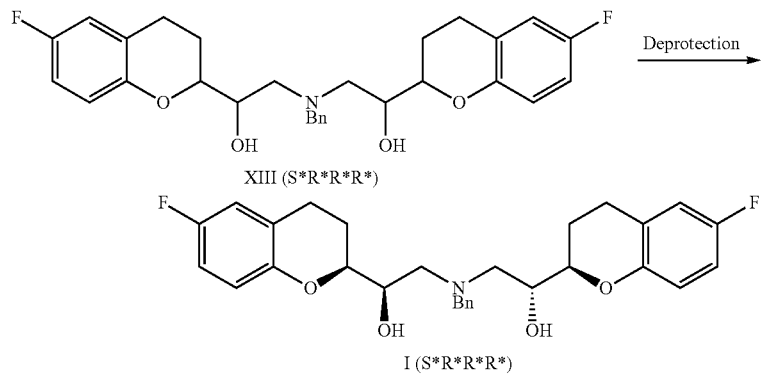

wherein I (S*R*R*R*) is racemate, which is a racemic mixture consisting of equimolar amounts of the compound of formula Ia (SRRR) and the enantiomer Ib (RSSS).

In an embodiment, in step 1), the metal composite hydride used as reducing agent is LiAlH$_4$ or sodium bis(2-methoxyethoxy)aluminum dihydride, the solvent used in the reaction is organic aprotic solvent, such as tetrahydrofuran, methyltetrahydrofuran, toluene, dioxane, diethyl ether, isopropyl ether, tert-butyl methyl ether, toluene, or a mixture of any two or more of them, and the reaction temperature is −100° C. to 60° C.

In an embodiment, in step 2), the catalyst used in the selective catalytic hydrogenation is selected from Lindlar catalyst or P-2 nickel boride/ethylenediamine catalyst.

In an embodiment, in step 3), epoxidation of the compound of formula IV1 in trans-configuration or the compound of formula IV2 in cis-configuration can be carried out by using the epoxidation methods commonly used in the art, for example, the epoxidating reagent which can be used in the reaction is selected from organic peroxy-acid, such as MCPBA, trifluoroperacetic acid, dimethyldioxirane (DMDO), a mixture of hydrogen peroxide and acetic acid, and a mixture of VO(acac)$_2$ and tert-butyl hydroperoxide, and the system of pyridine-H$_2$O$_2$ in the presence of catalytic amount of methylrhenium trioxide (MTO), the solvent in the reaction is organic aprotic solvent, such as methylene dichloride, chloroform, tetrahydrofuran, toluene, or a mixture of any two or more of them, and the reaction temperature is −50° C. to 50° C.

In an embodiment, in step 4), the deprotection can be carried out by the conventional methods in the field of organic chemistry to remove the hydroxy-protecting group, for example, by hydrogenolysis in the presence of catalyst to remove benzyl protective group, and cyclization is carried out in the presence of base; the catalyst used in the hydrogenolysis is Pd catalyst, such as Pd/C, Pd(OH)$_2$, Pd(OAc)$_2$, PdCl$_2$, Pd; the base used in the cyclization is selected from alkali metal and alkaline earth metal hydroxide or carbonate, alkoxide, or organic base, such as NaOH, KOH, K$_2$CO$_3$, NaOMe, DBU; or the deprotection and the cyclization are carried out by hydrogenolysis using Pd/C as catalyst under basic condition to simultaneously remove benzyl protective group and perform cyclization, to directly give the cyclization product.

In an embodiment, in step 5), the sulfonyl halide used in the sulfonylation can be arylsulfonyl chloride or substituted arylsulfonyl chloride or alkylsulfonyl chloride, such as p-toluenesulfonyl chloride, phenylsulfonyl chloride, p-halophenylsulfonyl chloride, p-nitrophenylsulfonyl chloride, o-nitrophenylsulfonyl chloride or methylsulfonyl chloride; no catalyst is used or an appropriate amount of acylation catalyst is used in the reaction, and the catalyst can be dialkyltin oxides, DMAP, such as dibutyltin oxide and 2,2-dibutyl-1,3,2-dioxastannolane; the base used in the reaction can be conventional organic base, such as pyridine, organic tertiary amine, such as triethylamine or diisopropylethylamine, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them, and the reaction temperature is −50° C. to 50° C.

In an embodiment, in step 6), alkylation of amine is carried out by reaction of benzyl amine with corresponding sulfonate, and the molar ratio of the benzyl amine used and the corresponding sulfonate substrate is 1/1 to 10/1, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them, and the reaction temperature is −25° C. to 150° C.

In an embodiment, in step 7), the base used in the cross-coupling reaction can be selected from inorganic base, such as K$_2$CO$_3$, Na$_2$CO$_3$, or organic tertiary amine, such as triethylamine or diisopropylethylamine, the solvent in the reaction is organic protic solvent, such as ethanol, propanol, isopropanol, or organic polar aprotic solvent, such as acetone, butanone, toluene, tetrahydrofuran, dimethylformamide, or a mixture of any two or more of these solvents, and the reaction temperature is −25° C. to 150° C.

In an embodiment, in step 9), the catalyst used in the deprotection reaction is Pd catalyst, such as Pd/C, Pd(OH)$_2$, Pd(OAc)$_2$, PdCl$_2$, Pd; the solvent in the reaction is alcohol or ester or ether, or a mixture of any two or more of these solvents, such as methanol or ethanol.

In a preferred embodiment, in step 1), the metal composite hydride used as reducing agent is LiAlH$_4$ or sodium bis(2-methoxyethoxy)aluminum dihydride, the solvent used in the reaction is organic aprotic solvent, such as methyltetrahydrofuran, tetrahydrofuran, methyltetrahydrofuran, toluene, dioxane, diethyl ether, isopropyl ether, tert-butyl methyl ether, toluene, or a mixture of any two or more of them;

in step 2), the catalyst used in the selective catalytic hydrogenation is selected from Lindlar catalyst or P-2 nickel boride/ethylenediamine catalyst;

in step 3), epoxidation of the compound of formula IV1 in trans-configuration or the compound of formula IV2 in cis-configuration can be carried out by using the epoxidation methods commonly used in the art, for example, the epoxidating reagent which can be used in the reaction is selected from organic peroxy-acid, such as MCPBA, trifluoroperacetic acid, dimethyldioxirane (DMDO), a mixture of hydrogen peroxide and acetic acid, and a mixture of VO(acac)$_2$ and tert-butyl hydroperoxide, and the system of pyridine-H$_2$O$_2$ in the presence of catalytic amount of methylrhenium trioxide (MTO), and the solvent in the reaction is organic aprotic solvent, such as methylene dichloride, chloroform, methyltetrahydrofuran, tetrahydrofuran, toluene, or a mixture of any two or more of them;

in step 4), the deprotection can be carried out by the conventional methods in the field of organic chemistry to remove the hydroxy-protecting group, for example, by hydrogenolysis in the presence of catalyst to remove benzyl protective group, and cyclization is carried out in the presence of base; the catalyst used in the hydrogenolysis is Pd catalyst, such as Pd/C, Pd(OH)$_2$, Pd(OAc)$_2$, PdCl$_2$, Pd; the base used in the cyclization is selected from alkali metal and alkaline earth metal hydroxide or carbonate, alkoxide, or organic base, such as NaOH, KOH, K$_2$CO$_3$, NaOMe, DBU; or the deprotection and the cyclization are carried out by hydrogenolysis using Pd/C as catalyst under basic condition to simultaneously remove benzyl protective group and perform cyclization, to directly give the cyclization product;

in step 5), the sulfonyl halide used in the sulfonylation can be arylsulfonyl chloride or substituted arylsulfonyl chloride or alkylsulfonyl chloride, such as p-toluenesulfonyl chloride, phenylsulfonyl chloride, p-halophenylsulfonyl chloride, p-nitrophenylsulfonyl chloride or o-nitrophenylsulfonyl chloride or methylsulfonyl chloride; no catalyst is used or an appropriate amount of acylation catalyst is used in the reaction, and the catalyst can be dialkyltin oxides, DMAP, such as dibutyltin oxide and 2,2-dibutyl-1,3,2-dioxastannolane; the base used in the reaction can be conventional organic base, such as pyridine, organic tertiary amine, such as triethylamine or diisopropylethylamine, the solvent in the reaction is organic aprotic solvent, such as methylene dichloride, chloroform, tetrahydrofuran, methyltetrahydrofuran, pyridine, toluene, acetonitrile, ethyl acetate, DMF, DMA, or a mixture of any two or more of them;

in step 6), alkylation of amine is carried out by reaction of benzyl amine with corresponding sulfonate, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them;

in step 7), the base used in the cross-coupling reaction can be selected from inorganic base, such as K$_2$CO$_3$, Na$_2$CO$_3$, or organic tertiary amine, such as triethylamine or diisopropylethylamine, the solvent in the reaction is organic protic solvent, such as ethanol, propanol, isopropanol, or organic polar aprotic solvent, such as acetone, butanone, toluene, tetrahydrofuran, dimethylformamide, or a mixture of any two or more of these solvents; and in step 9), the catalyst used in the deprotection reaction is Pd catalyst, such as Pd/C, Pd(OH)$_2$, Pd(OAc)$_2$, PdCl$_2$, Pd, the solvent in the reaction is alcohol, ester or ether, or a mixture of any two or more of these solvents, such as methanol or ethanol.

A skilled person in the art will understand that, in above process for preparation of the compound of formula I, the reaction product of any one of step 1) to step 9) can be used as starting material to perform subsequent steps described above to prepare the compound of formula I. For example, the compounds of formula IV1 and formula IV2 can be used as starting materials to perform steps 2) to 9) described above to obtain racemic Nebivolol of formula I, or the compounds of formula IX and formula XII can be used as starting materials to perform steps 7) to 9) described above to obtain racemic Nebivolol of formula I.

In another aspect, the present invention provides a process for preparation of formula IV1,

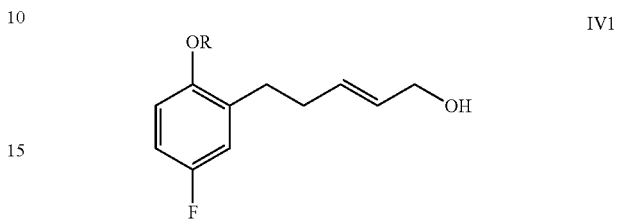

wherein R is hydroxy-protecting group, which is selected from aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, the process comprising the following steps:

reducing the compound of formula III with metal composite hydride to give the compound of formula IV1, and optionally the following step: to the resulting compound of formula IV1, adding non-polar organic solvent, such as n-hexane, n-heptane, petroleum ether, diethyl ether, isopropyl ether or tert-butyl methyl ether, or a mixture of any two or more of them, stirring at low temperature such as 0° C. to −20° C., followed by crystallization and filtration, to yield the compound of formula IV1 as solid,

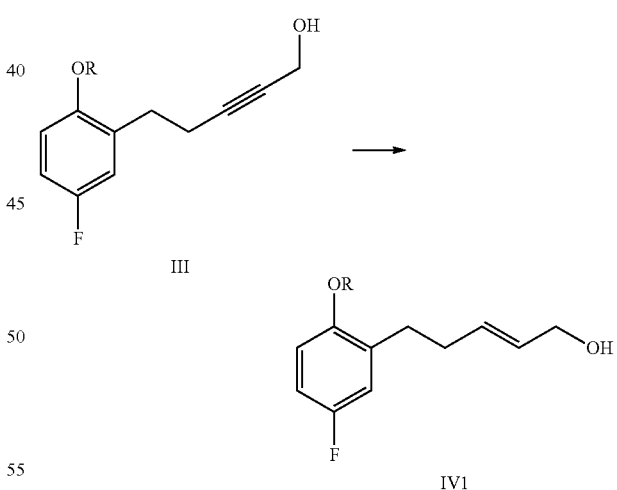

wherein R is defined as above.

In a preferred embodiment, in the above process, the metal composite hydride used as reducing agent is LiAlH$_4$ or sodium bis(2-methoxyethoxy)aluminum dihydride, the solvent used in the reaction is organic aprotic solvent, such as tetrahydrofuran, methyltetrahydrofuran, toluene, dioxane, diethyl ether, isopropyl ether, tert-butyl methyl ether, toluene, or a mixture of any two or more of them.

In another aspect, the present invention provides a process for preparation of formula IV2,

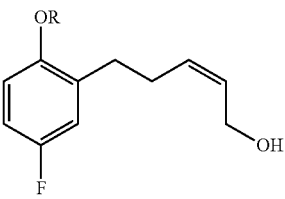

IV2

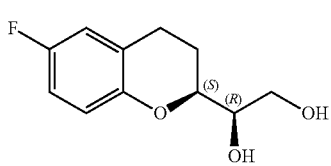

VIIa (S/R)

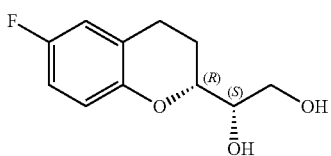

VIIb (R/S)

wherein R is hydroxy-protecting group, which is selected from aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, the process comprising the following steps:

reducing the compound of formula III via selective catalytic hydrogenation to give the compound of formula IV2 in cis-configuration, and optionally the following step: to the resulting compound of formula IV2, adding non-polar organic solvent, such as n-hexane, n-heptane, petroleum ether, diethyl ether, isopropyl ether or tert-butyl methyl ether, or a mixture of any two or more of them, stirring at low temperature such as 0° C. to −20° C., followed by crystallization and filtration, to yield the compound of formula IV2 as solid, the process comprising the following steps:

3) epoxidation of the compound of formula IV1 in trans-configuration in the presence of epoxidating reagent to give epoxide intermediate V

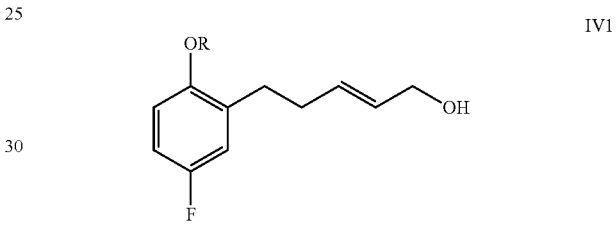

IV1

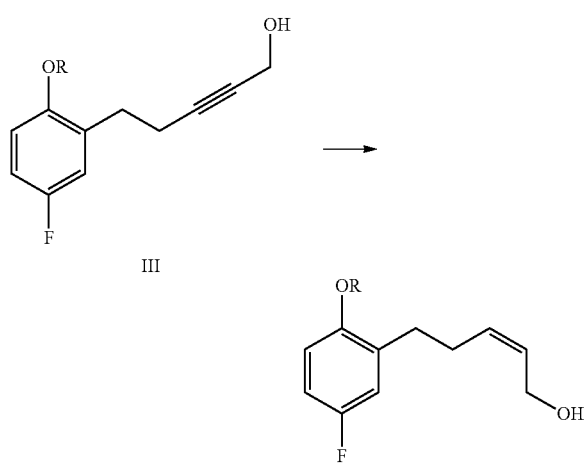

wherein R is defined as above.

In a preferred embodiment, in the above process, the catalyst used in the selective catalytic hydrogenation is selected from Lindlar catalyst or P-2 nickel boride/ethylenediamine catalyst.

In another aspect, the present invention provides a process for preparation of the compound of formula VII (S*/R*), wherein R is hydroxy-protecting group, which is selected from alkyl, haloalkyl, aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, but R shown in the follow formulae is represented by benzyl (Bn) as an example,

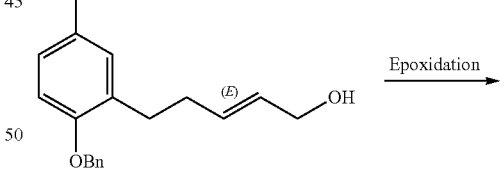

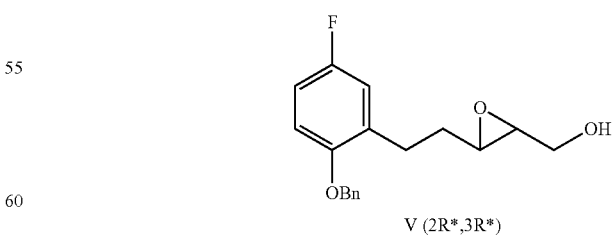

V (2R*,3R*)

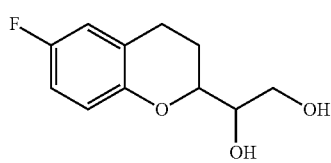

VII (S*/R*)

wherein VII (S*/R*) is racemate, which is a racemic mixture consisting of equimolar amounts of the compound of formula VIIa (S/R) and the enantiomer VIIb (R/S), wherein the compound V is racemate, which is a racemic mixture consisting of equimolar amounts of the compound of formula Va and the enantiomer Vb, the relative configuration of which is represented as V (2R*,3R*)

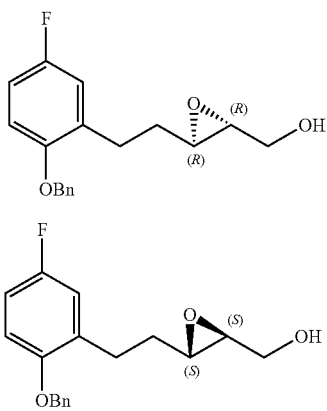

Va (2R,3R)

Vb (2S,3S)

4) deprotecting the compound of formula V (2R*,3R*), followed by cyclization reaction, to give the intermediate compounds of formula VII (S*/R*), wherein R is defined as above, but R shown in the follow formulae is represented by benzyl (Bn) as an example,

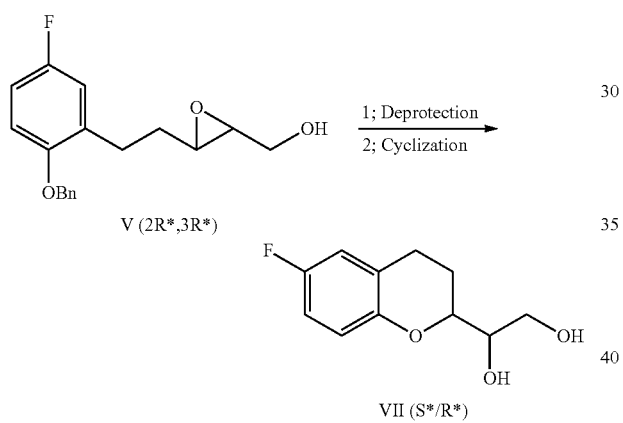

V (2R*,3R*)

1; Deprotection
2; Cyclization

VII (S*/R*)

wherein VII (S*/R*) is racemate, which is a racemic mixture consisting of equimolar amounts of the compound of formula VIIa (S/R) and the enantiomer VIIb (R/S),

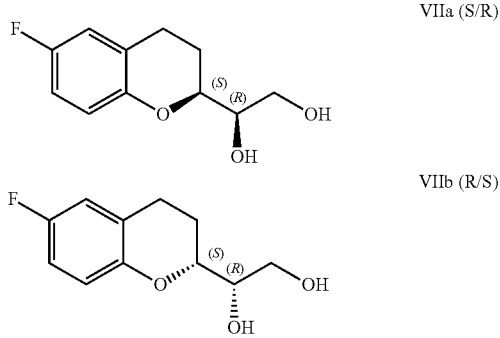

VIIa (S/R)

VIIb (R/S)

In a preferred embodiment, the reaction condition, solvent, and the like in the steps 3) and 4) are as described above.

In another aspect, the present invention provides a process for preparation of the compound of formula VIII (R*/R*),

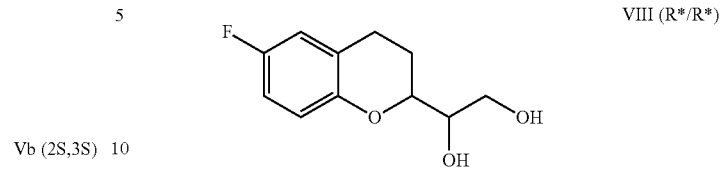

VIII (R*/R*)

wherein VIII (R*/R*) is racemate, which is a racemic mixture consisting of equimolar amounts of the compound of formula VIIIa (R/R) and the enantiomer VIIIb (S/S),

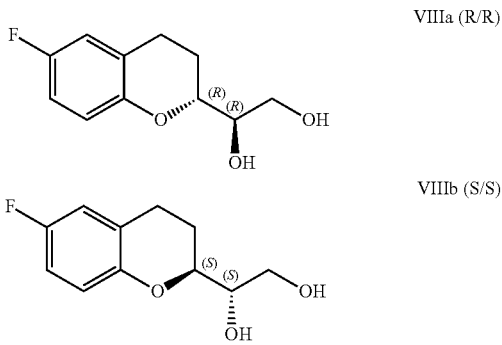

VIIIa (R/R)

VIIIb (S/S)

the process comprising the following steps:

3) epoxidation of the compound of formula IV2 in cis-configuration in the presence of epoxidating reagent to give epoxide intermediate VI,

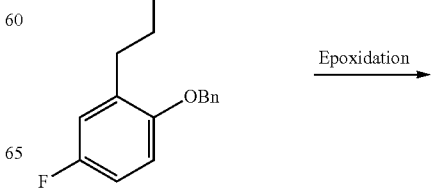

IV2 wherein R is hydroxy-protecting group, which is selected from alkyl, haloalkyl, aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, but R shown in the follow formulae is represented by benzyl (Bn) as an example, Epoxidation -continued

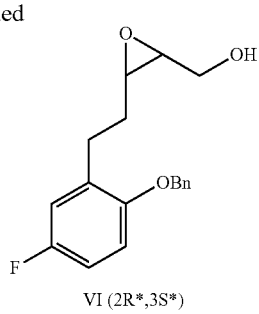

VI (2R*,3S*)

wherein the compound VI is racemate, which is a racemic mixture consisting of equimolar amounts of the compound of formula VIa and the enantiomer VIb, the relative configuration of which is represented as VI (2R*,3S*)

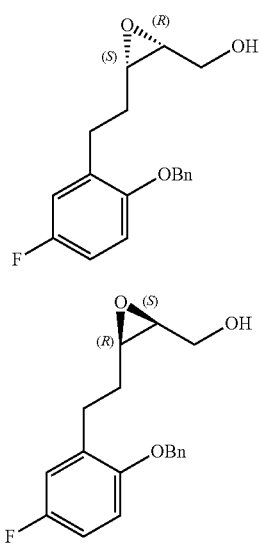

VIa (2R,3S)

VIb (2S,3R)

4) deprotecting the compound of formula VI (2R*,3S*), followed by cyclization reaction, to give the intermediate compounds of formula VIII (R*/R*), wherein R is defined as above, but R shown in the follow formulae is represented by benzyl (Bn) as an example,

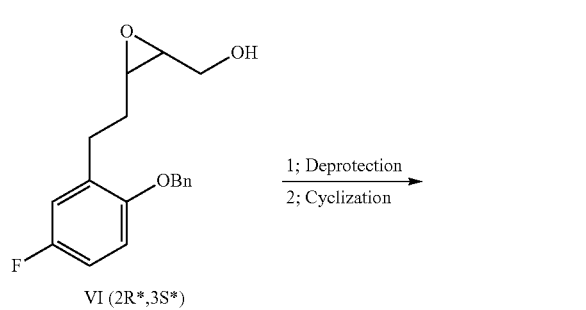

VI (2R*,3S*)

VIII (R*/R*)

wherein VIII (R*/R*) is racemate, which is a racemic mixture consisting of equimolar amounts of the compound of formula VIIIa (R/R) and the enantiomer VIIIb (S/S),

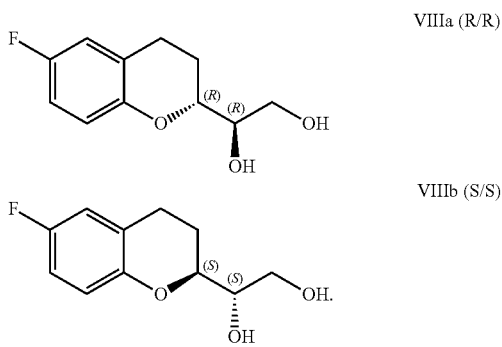

VIIIa (R/R)

VIIIb (S/S)

In a preferred embodiment, the reaction condition, solvent, and the like in the steps 3) and 4) are as described above.

In another aspect, the present invention provides a process for preparation of racemic Nebivolol of formula I,

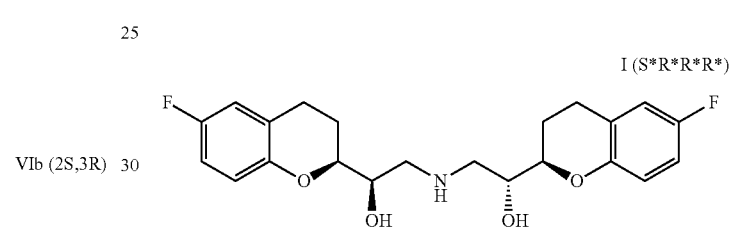

I (S*R*R*R*)

wherein I (S*R*R*R*) represents racemate, which is a racemic mixture consisting of equimolar amounts of D-Nebivolol Ia (SRRR) and the enantioner thereof L-Nebivolol Ib (RSSS) having the following configurations

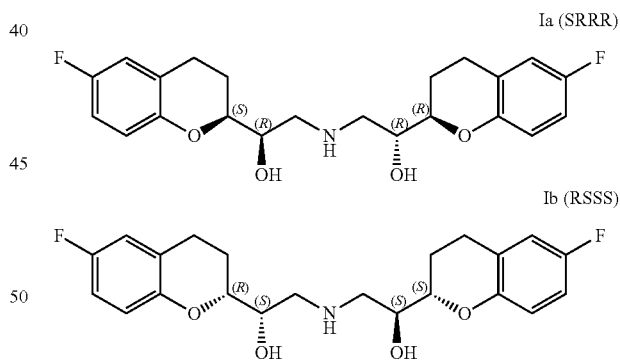

Ia (SRRR)

Ib (RSSS)

the process comprising the following steps a) to c) or d) and steps 1) to 9):

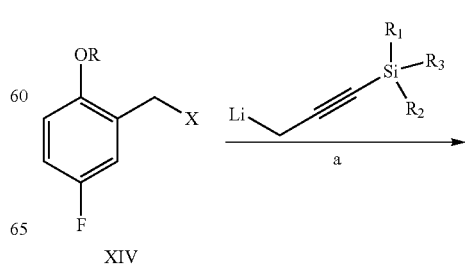

XIV

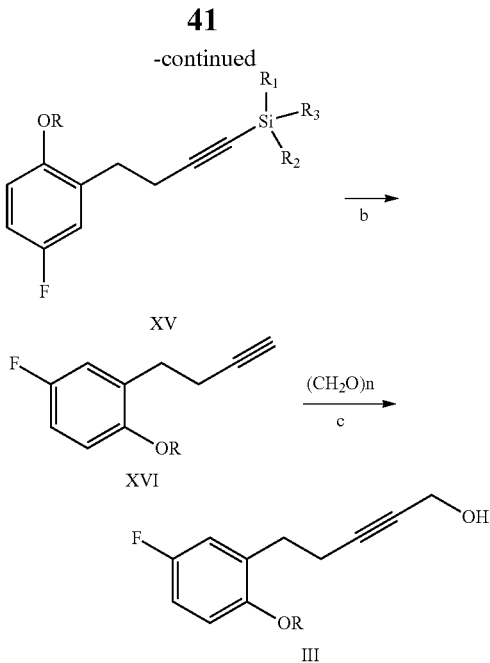

step a): reacting the compound of formula XIV with 3-(tri-substituted silyl)-prop-2-yne-1-lithium to give the compound of formula XV, wherein each of $R_1$, $R_2$ and $R_3$ is independently selected from alkyl or aryl, such as methyl, tert-butyl or phenyl; R is hydroxy-protecting group, which is selected from alkyl, haloalkyl, aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, and X is halogen;

step b): removing the silyl protective group at the terminal of alkynyl in the compound of formula XV to give the compound of formula XVI, wherein R is defined as above;

step c): reacting the compound of formula XVI with paraformaldehyde in the presence of base or organometallic reagent to give the compound of formula III, wherein R is defined as above; and optionally step d): to the compound of formula III obtained by step c), adding non-polar organic solvent, such as n-hexane, n-heptane, petroleum ether, diethyl ether, isopropyl ether or tert-butyl methyl ether, or a mixture of any two or more of them, stirring at low temperature such as 0° C. to −20° C., followed by crystallization and filtration, to yield the compound of formula III as solid;

step 1): reducing the compound of formula III with metal composite hydride to give the compound of formula IV1 in trans-configuration, and optionally the following step: to the resulting compound of formula IV1, adding non-polar organic solvent, such as n-hexane, n-heptane, petroleum ether, diethyl ether, isopropyl ether or tert-butyl methyl ether, or a mixture of any two or more of them, stirring at low temperature such as 0° C. to −20° C., followed by crystallization and filtration, to yield the compound of formula IV1 as solid,

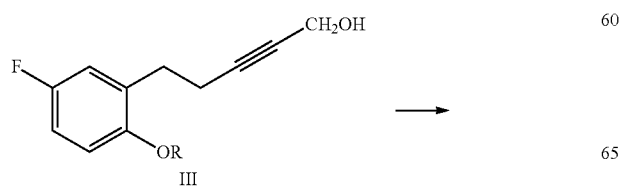

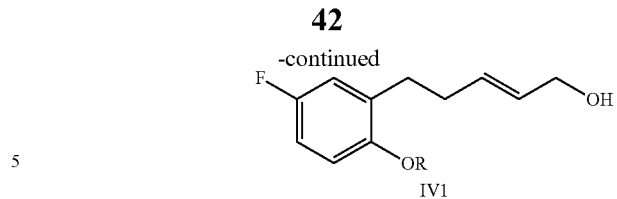

wherein R is defined as above, step 2): reducing the compound of formula III via selective catalytic hydrogenation to give the compound of formula IV2 in cis-configuration, and optionally the following step: to the resulting compound of formula IV2, adding non-polar organic solvent, such as n-hexane, n-heptane, petroleum ether, diethyl ether, isopropyl ether or tert-butyl methyl ether, or a mixture of any two or more of them, stirring at low temperature such as 0° C. to −20° C., followed by crystallization and filtration, to yield the compound of formula IV2 as solid,

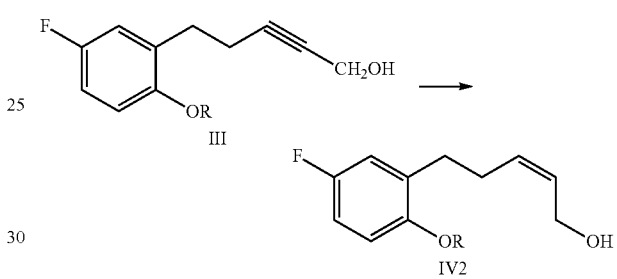

wherein R is defined as above, step 3): epoxidation of the compound of formula IV1 in trans-configuration and the compound of formula IV2 in cis-configuration in the presence of epoxidating reagent to give epoxide intermediates V and VI, respectively, wherein R is defined as above,

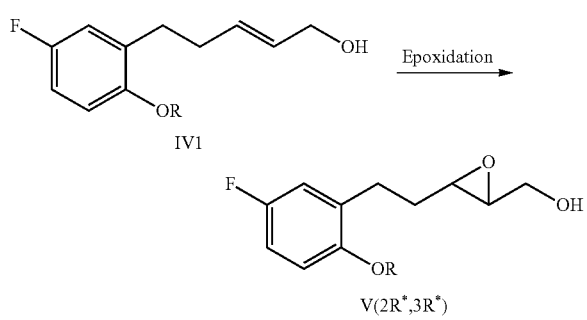

wherein the compound V is racemate, which is a racemic mixture consisting of equimolar amounts of the compound of formula Va and the enantiomer Vb, the relative configuration of which is represented as V (2R*,3R*)

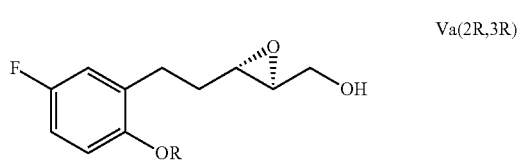

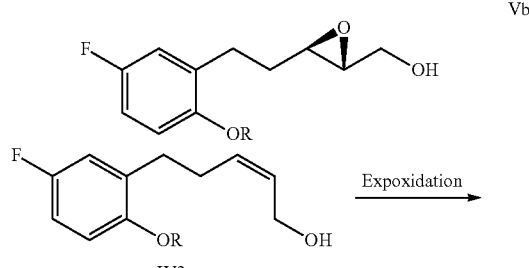

Vb(2S,3S)

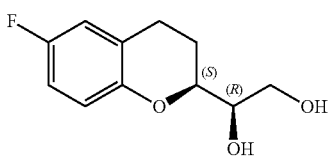

VIIa (S/R)

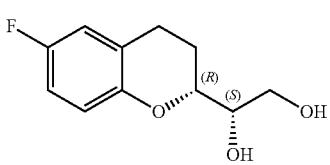

VIIb (R/S)

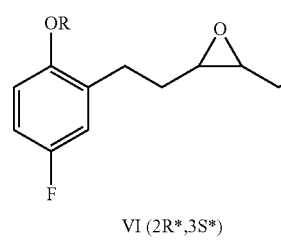

VI (2R*,3S*)

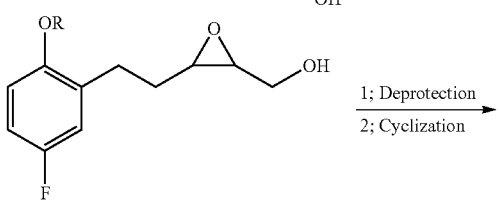

VI (2R*,3S*)

wherein the compound VI is racemate, which is a racemic mixture consisting of equimolar amounts of the compound of formula VIa and the enantiomer VIb, the relative configuration of which is represented as VI (2R*,3S*)

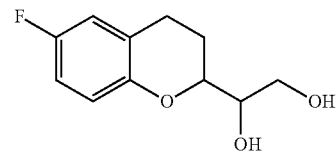

VIII (R*/R*)

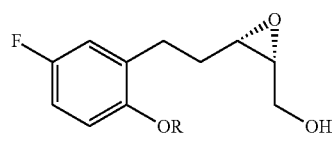

VIa(2R,3S)

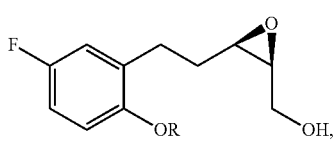

VIb(2S,3R)

wherein VIII (R*/R*) is racemate, which is a racemic mixture consisting of equimolar amounts of the compound of formula VIIIa (R/R) and the enantiomer VIIIb (S/S),

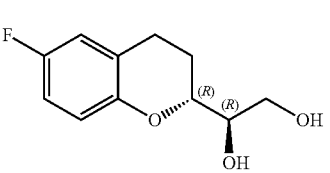

VIIIa (R/R)

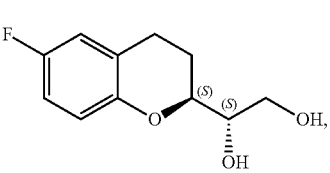

VIIIb (S/S)

step 4): deprotecting the compound of formula V and the compound of formula VI, followed by cyclization reaction, to give the intermediate compounds of formula VII (S*/R*) and formula VIII (R*/R*), respectively, wherein R is defined as above,

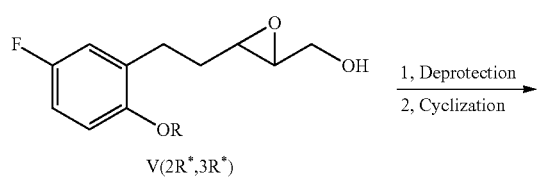

V(2R*,3R*)

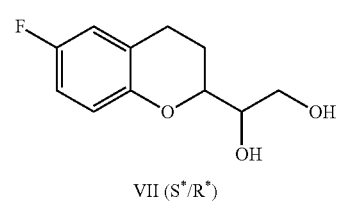

VII (S*/R*)

wherein VII (S*/R*) is racemate, which is a racemic mixture consisting of equimolar amounts of the compound of formula VIIa (S/R) and the enantiomer VIIb (R/S), step 5): sulfonylating the compounds of formula VII and formula VIII with sulfonyl halide of formula M-SO₂X (wherein M is alkyl or substituted or unsubstituted aryl, X is halogen) in the presence of catalyst and base, to give the compounds IX (S*/R*) and X (R*/R*), respectively,

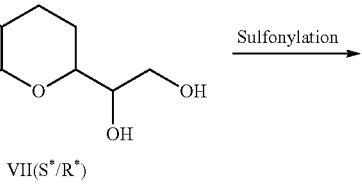

VII(S*/R*)

-continued

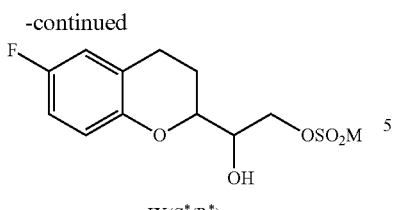

IX(S*/R*)

wherein IX (S*/R*) is racemate, which is a racemic mixture consisting of equimolar amounts of the compound of formula IXa (S/R) and the enantiomer IXb (R/S), IXa(S/R)

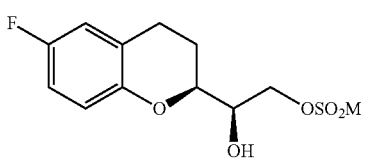

IXb(R/S)

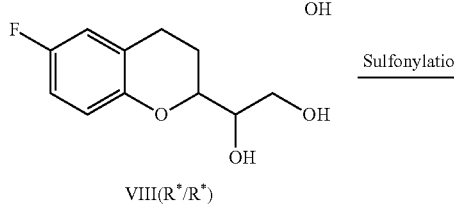

VIII(R*/R*) → Sulfonylation

X(R*/R*)

wherein X (R*/R*) is racemate, which is a racemic mixture consisting of equimolar amounts of the compound of formula Xa (R/R) and the enantiomer Xb (S/S), Xa(R/R)

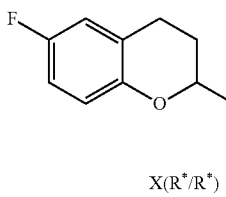

Xb(S/S)

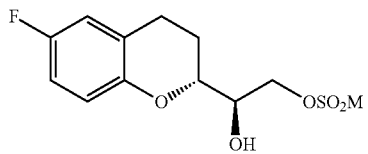

step 6): reacting the compound of formula IX or X with benzyl amine to perform alkylation of amine, to give the corresponding compound XI or XII;

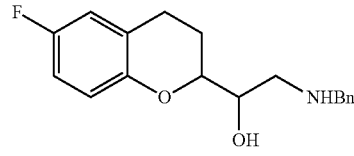

IX(S*/R*) → BnNH₂

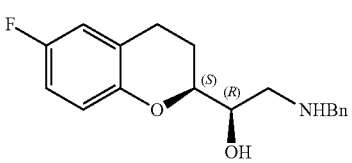

XI (S*/R*)

wherein XI (S*/R*) is racemate, which is a racemic mixture consisting of equimolar amounts of the compound of formula XIa (S/R) and the enantiomer XIb (R/S), XIa (S/R)

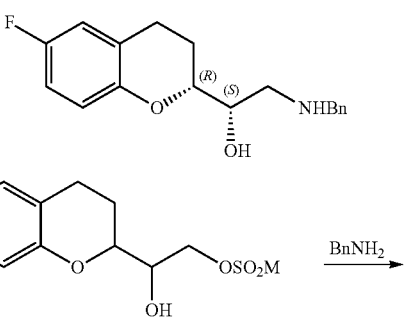

XIb (R/S)

X(R*/R*) → BnNH₂

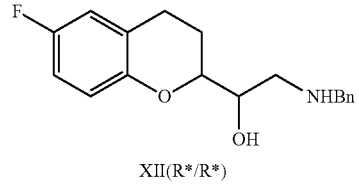

XII(R*/R*)

wherein XII (R*/R*) is racemate, which is a racemic mixture consisting of equimolar amounts of the compound of formula XIIa (R/R) and the enantiomer XIIb (S/S)

XIIa (R/R)

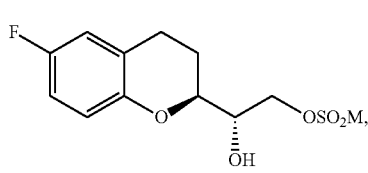

-continued

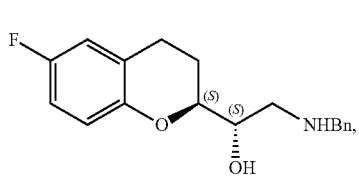
XIIb (S/S)

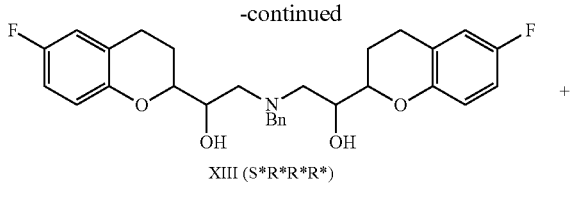
XIII (S*R*R*R*)

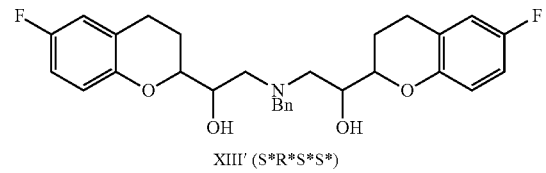
XIII' (S*R*S*S*)

step 7): cross-coupling reaction of the intermediate compounds IX (S*/R*) and XII (R*/R*) or the intermediate compounds X (R*/R*) and XI (S*/R*) under basic condition, to give the compounds XIII (S*R*R*R*) and XIII' (S*R*S*S*), wherein the definition of R" is the same as the above definition of

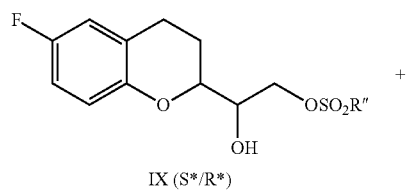
IX (S*/R*)

+

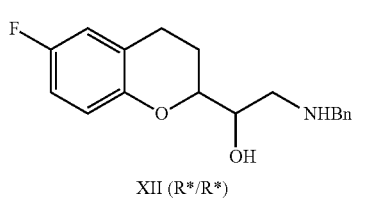
XII (R*/R*)

$\xrightarrow[\text{Base}]{\text{cross-coupling}}$

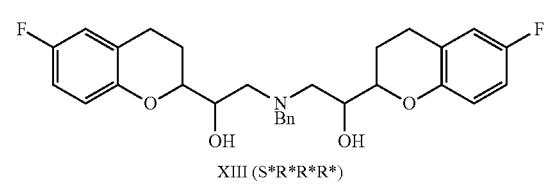
XIII (S*R*R*R*)

or

XIII' (S*R*R*R*)

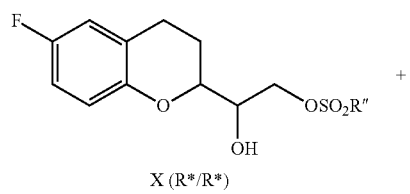
X (R*/R*)

+

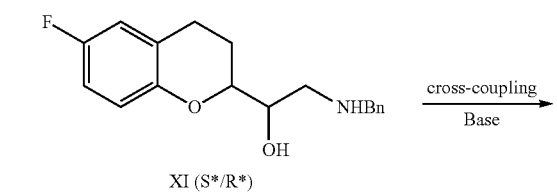
XI (S*/R*)

$\xrightarrow[\text{Base}]{\text{cross-coupling}}$ wherein XIII (S*R*R*R*) is racemate, which is a racemic mixture consisting of equimolar amounts of the compound of formula XIIIa (SRRR) and the enantiomer XIIIb (RSSS),

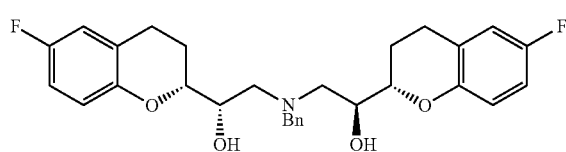
XIIIa (SRRR)

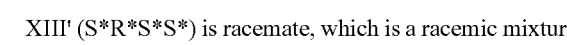
XIIIb (RSSS)

XIII' (S*R*S*S*) is racemate, which is a racemic mixture consisting of equimolar amounts of the compound of formula XIII'a (SRSS) and the enantiomer XIII'b (RSRR),

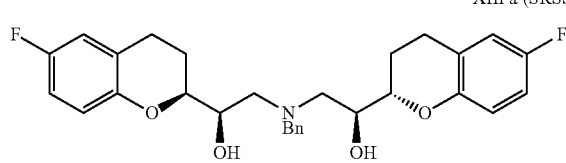
XIII'a (SRSS)

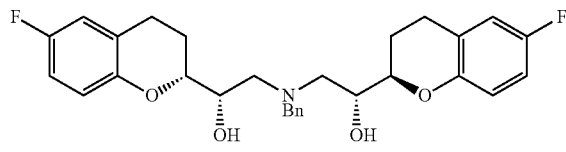
XIII'b (RSRR)

step 8): Forming salt of a mixture of the compounds of formula XIII and formula XIII', and purifying by recrystallization to remove the isomer XIII' (S*R*S*S*), to give the intermediate compound XIII (S*R*R*R*), step 9): deprotecting the intermediate compound XIII to yield racemic Nebivolol of formula I

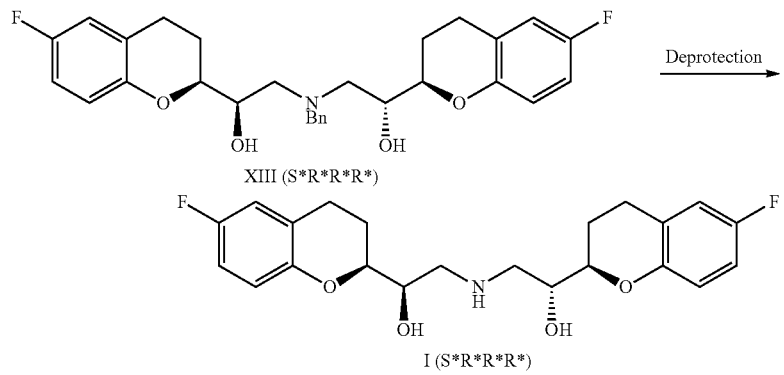

XIII (S*R*R*R*)

I (S*R*R*R*)

wherein I (S*R*R*R*) is racemate, which is a racemic mixture consisting of equimolar amounts of the compound of formula Ia (SRRR) and the enantiomer Ib (RSSS).

Regarding this process for preparation of the compound of formula I, the reaction conditions, solvents, reagents used in steps a) to c) and steps 1) to 9) are as described above.

In a further preferred embodiment, in step a), the reaction is carried out in organic aprotic solvent, such as methyltetrahydrofuran, tetrahydrofuran, dioxane, diethyl ether, tert-butyl methyl ether or toluene;

in step b), the reaction is carried out in the presence of base, acid, or a salt containing fluorine, preferably in the presence of base, said base is selected from alkali metal or alkali earth metal hydroxide or carbonate, such as NaOH, KOH, $Na_2CO_3$, $K_2CO_3$, the solvent used in the reaction is selected from protic solvent, such as water, methanol, ethanol, or a mixture of any two or more of them;

in step c), the base is selected from metal hydride or organic base, such as $NaNH_2$ or $KNH_2$, the organometallic reagent is selected from BuLi, t-BuLi, s-BuLi, LDA or Grignard reagent, such as MeMgX, EtMgX, BuMgX, i-PrMgX, wherein X is Br, I or Cl, the solvent used in the reaction is organic aprotic solvent, such as tetrahydrofuran, methyltetrahydrofuran, toluene, dioxane, diethyl ether, isopropyl ether, tert-butyl methyl ether, toluene, or a mixture of any two or more of them;

in step 1), the metal composite hydride used as reducing agent is $LiAlH_4$ or sodium bis(2-methoxyethoxy)aluminum dihydride, the solvent used in the reaction is organic aprotic solvent, such as tetrahydrofuran, methyltetrahydrofuran, toluene, dioxane, diethyl ether, isopropyl ether, tert-butyl methyl ether, toluene, or a mixture of any two or more of them;

in step 2), the catalyst used in the selective catalytic hydrogenation is selected from Lindlar catalyst or P-2 nickel boride/ethylenediamine catalyst;

in step 3), epoxidation of the compound of formula IV1 in trans-configuration or the compound of formula IV2 in cis-configuration can be carried out by using the epoxidation methods commonly used in the art, for example, the epoxidating reagent which can be used in the reaction is selected from organic peroxy-acid, such as MCPBA, trifluoroperacetic acid, dimethyldioxirane (DMDO), a mixture of hydrogen peroxide and acetic acid, and a mixture of $VO(acac)_2$ and tert-butyl hydroperoxide, and the system of pyridine-$H_2O_2$ in the presence of catalytic amount of methylrhenium trioxide (MTO), and the solvent in the reaction is organic aprotic solvent, such as methylene dichloride, chloroform, tetrahydrofuran, toluene, or a mixture of any two or more of them;

in step 4), the deprotection can be carried out by the conventional methods in the field of organic chemistry to remove the hydroxy-protecting group, for example, by hydrogenolysis in the presence of catalyst to remove benzyl protective group, and cyclization is carried out in the presence of base; the catalyst used in the hydrogenolysis is Pd catalyst, such as Pd/C, $Pd(OH)_2$, $Pd(OAc)_2$, $PdCl_2$, Pd; the base used in the cyclization is selected from alkali metal and alkaline earth metal hydroxide or carbonate, alkoxide, or organic base, such as NaOH, KOH, $K_2CO_3$, NaOMe, DBU; or the deprotection and the cyclization are carried out by hydrogenolysis using Pd/C as catalyst under basic condition to simultaneously remove benzyl protective group and perform cyclization, to directly give the cyclization product;

in step 5), the sulfonyl halide used in the sulfonylation can be arylsulfonyl chloride or substituted arylsulfonyl chloride or alkylsulfonyl chloride, such as p-toluenesulfonyl chloride, phenylsulfonyl chloride, p-halophenylsulfonyl chloride, p-nitrophenylsulfonyl chloride, o-nitrophenylsulfonyl chloride or methylsulfonyl chloride; no catalyst is used or an appropriate amount of acylation catalyst is used in the reaction, and the catalyst can be dialkyltin oxides, DMAP, such as dibutyltin oxide and 2,2-dibutyl-1,3,2-dioxastannolane; the base used in the reaction can be conventional organic base, such as pyridine, organic tertiary amine, such as triethylamine or diisopropylethylamine, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them;

in step 6), alkylation of amine is carried out by reaction of benzyl amine with corresponding sulfonate, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them;

in step 7), the base used in the cross-coupling reaction can be selected from inorganic base, such as $K_2CO_3$, $Na_2CO_3$, or organic tertiary amine, such as triethylamine or diisopropylethylamine, the solvent in the reaction is organic protic solvent, such as ethanol, propanol, isopropanol, or organic polar aprotic solvent, such as acetone, butanone, toluene, tetrahydrofuran, dimethylformamide, or a mixture of any two or more of these solvents; and in step 9), the catalyst used in the deprotection reaction is Pd catalyst, such as Pd/C, $Pd(OH)_2$, $Pd(OAc)_2$, $PdCl_2$, Pd, the solvent in the reaction is alcohol, ester or ether, or a mixture of any two or more of these solvents, such as methanol or ethanol.

A skilled person in the art will understand that, in above process for preparation of the compound of formula I, the reaction product of any one of step a) to step 9) can be used as starting material to perform subsequent steps described above to prepare the compound of formula I. For example, the compounds of formula XV can be used as starting material to perform steps b) to 9) described above, or the compounds of formula XVI can be used as starting material to perform steps c) to 9) described above, to obtain racemic Nebivolol of formula I.

In another aspect, the present invention provides a process for preparation of D-Nebivolol (formula Ia),

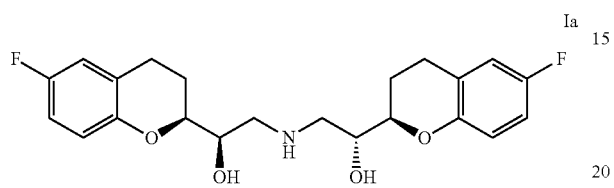

the process comprising the following steps:

3') asymmetric epoxidation of the compound of formula IV1 and the compound of formula IV2 to give intermediate compounds Va and VIa, respectively, wherein R is hydroxy-protecting group, which is selected from alkyl, haloalkyl, aralkyl, alkoxyalkyl, allyl, or silyl protective group, such as t-BuMe₂Si, t-BuPh₂Si, (i-Pr)₃Si, Et₃Si, methoxymethyl, benzyl or —CH₂Ar, wherein Ar is unsubstituted or substituted aryl, such as p-methoxyphenyl or halogen-substituted phenyl;

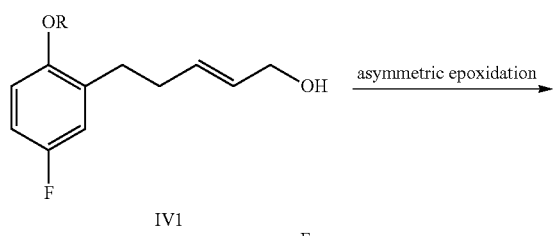

IV1

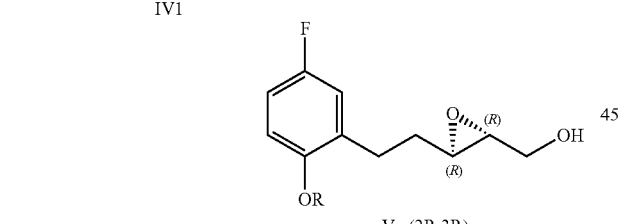

Va (2R,3R)

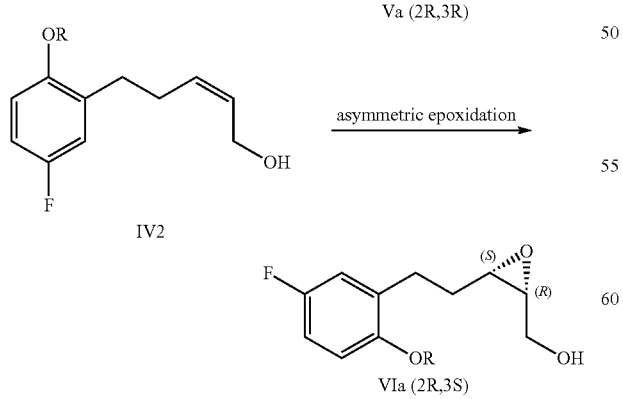

IV2

VIa (2R,3S)

4') deprotecting the intermediate compounds Va and VIa, followed by cyclization, to give the intermediate compounds VIIa and VIIIa, respectively, wherein R is defined as above,

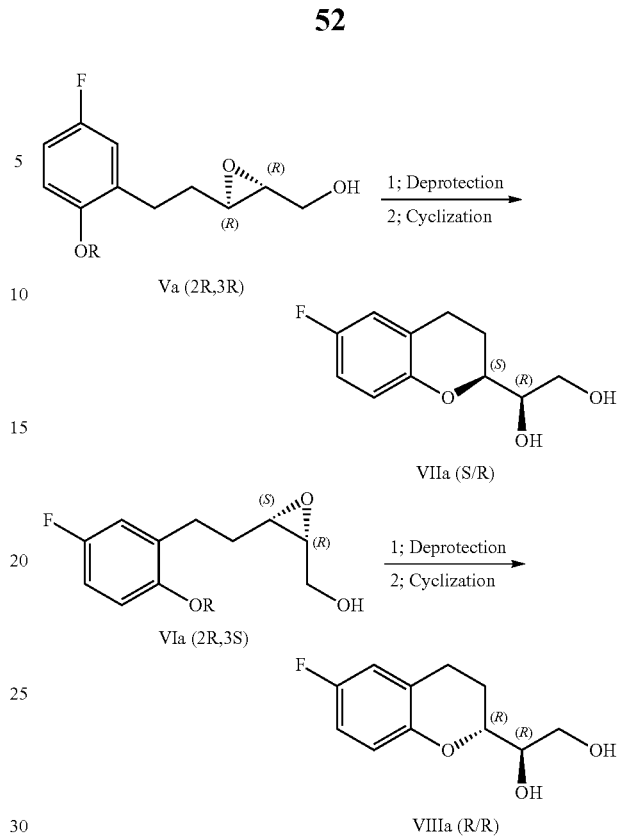

Va (2R,3R)

VIIa (S/R)

VIa (2R,3S)

VIIIa (R/R)

5') sulfonating the intermediate compounds VIIa and VIIIa with sulfonyl halide of formula M-SO₂X (wherein M is alkyl or substituted or unsubstituted aryl, X is halogen) in the presence of catalyst and base, to give the intermediate compounds IXa and Xa

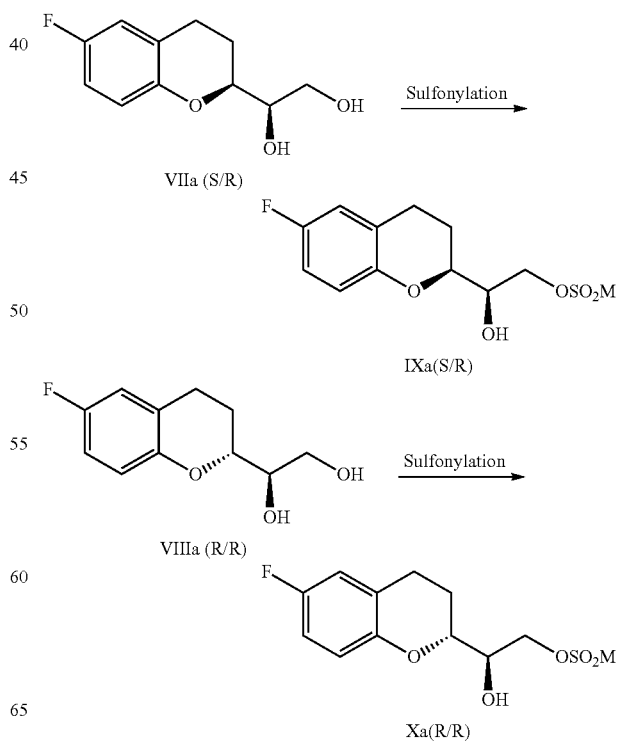

VIIa (S/R)

IXa(S/R)

VIIIa (R/R)

Xa(R/R)

6') reacting the intermediate compound IXa or the intermediate compound Xa with benzyl amine to perform alkylation of amine, to give the corresponding compound XIa or XIIa;

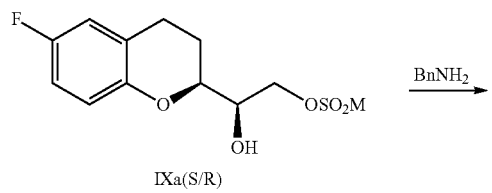

IXa (S/R)

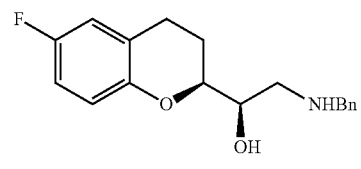

XIa (S/R)

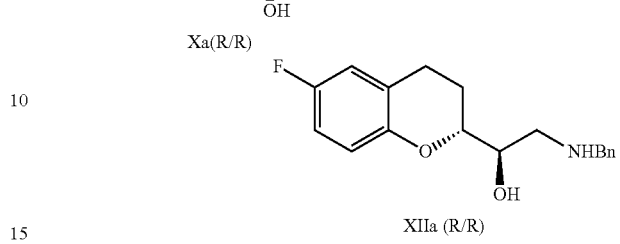

Xa (R/R)

XIIa (R/R)

7') cross-coupling reaction of the intermediate compounds IXa and XIIa or the intermediate compounds Xa and XIa under basic condition, to give the intermediate compounds XIIIa, wherein the definition of Ar' is the same as the above definition of M,

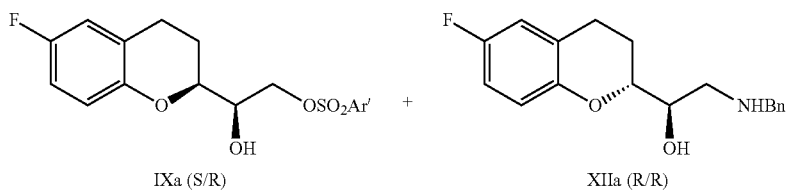

IXa (S/R)      XIIa (R/R)

cross-coupling | Base

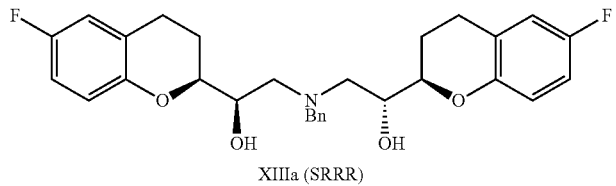

XIIIa (SRRR)

cross-coupling | Base

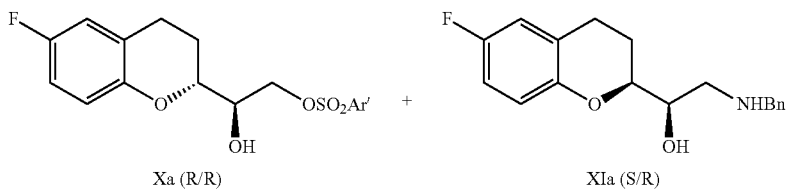

Xa (R/R)      XIa (S/R)

and optionally converting the intermediate compound XIIIa to the hydrochloride thereof, 8') deprotecting the intermediate compound XIIIa to give D-Nebivolol (formula Ia),

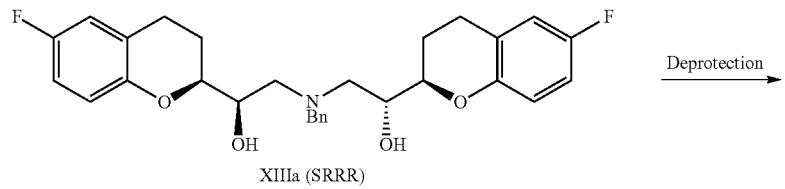

XIIIa (SRRR)

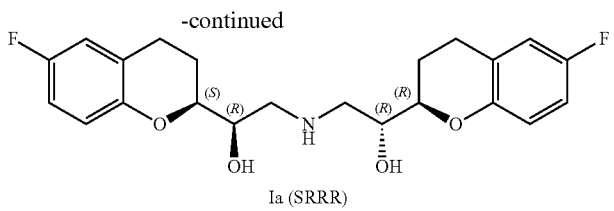

Ia (SRRR)

or converting the hydrochloride of the intermediate compound XIIIa to the intermediate compound XIIIa in free form by neutralization with base, followed by deprotection to give D-Nebivolol (formula Ia).

In another aspect, the present invention provides a process for preparation of L-Nebivolol (formula Ib),

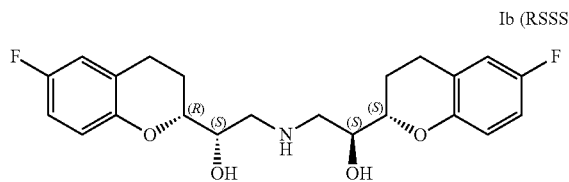

Ib (RSSS)

the process comprising the following steps:

3") asymmetric epoxidation of the compound of formula IV1 and the compound of formula IV2 to give intermediate compounds Vb and VIb, respectively, wherein R is hydroxy-protecting group, which is selected from alkyl, haloalkyl, aralkyl, alkoxyalkyl, allyl, or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl,

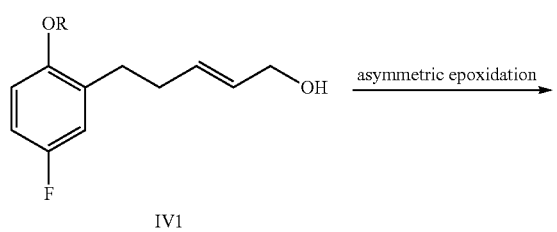

IV1

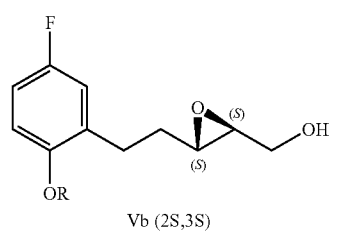

Vb (2S,3S)

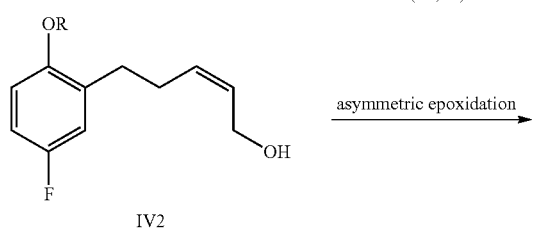

IV2

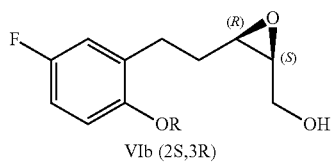

VIb (2S,3R)

4") deprotecting the intermediate compounds Vb and VIb, followed by cyclization, to give the intermediate compounds VIIb and VIIIb, wherein R is defined as above,

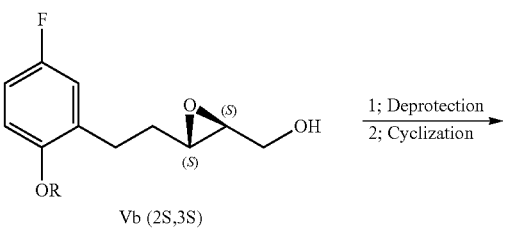

Vb (2S,3S)

VIIb (R/S)

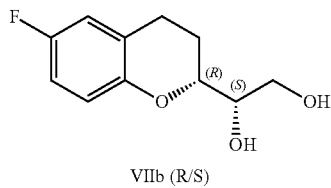

VIb (2S,3R)

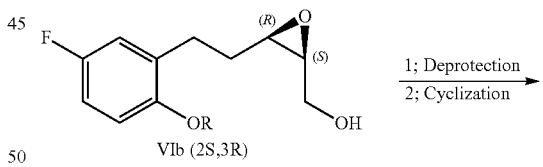

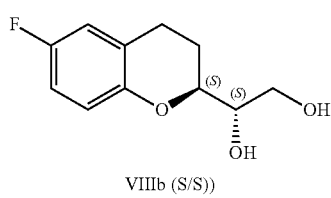

VIIIb (S/S)

5") sulfonating the intermediate compounds VIIb and VIIIb with sulfonyl halide of formula M-SO$_2$X (wherein M is alkyl or substituted or unsubstituted aryl, X is halogen) in the presence of catalyst and base, to give the intermediate compounds IXb and Xb,

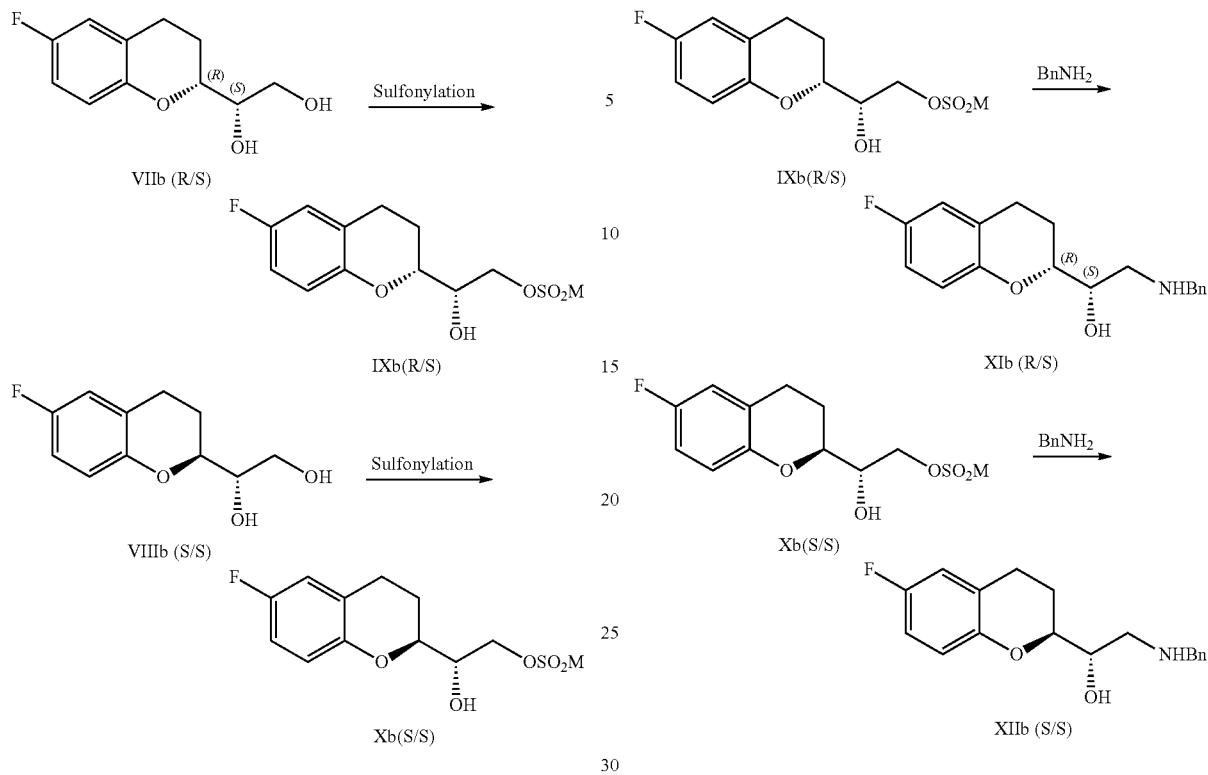

6") reacting the intermediate compound IXb or the intermediate compound Xb with benzyl amine to perform alkylation of amine, to give the intermediate compounds XIb or XIIb 7") cross-coupling reaction of the intermediate compounds IXb and XIIb or the intermediate compounds Xb and XIb under basic condition, to give the intermediate compounds XIIIb, wherein the definition of Ar' is the same as the above definition of M,

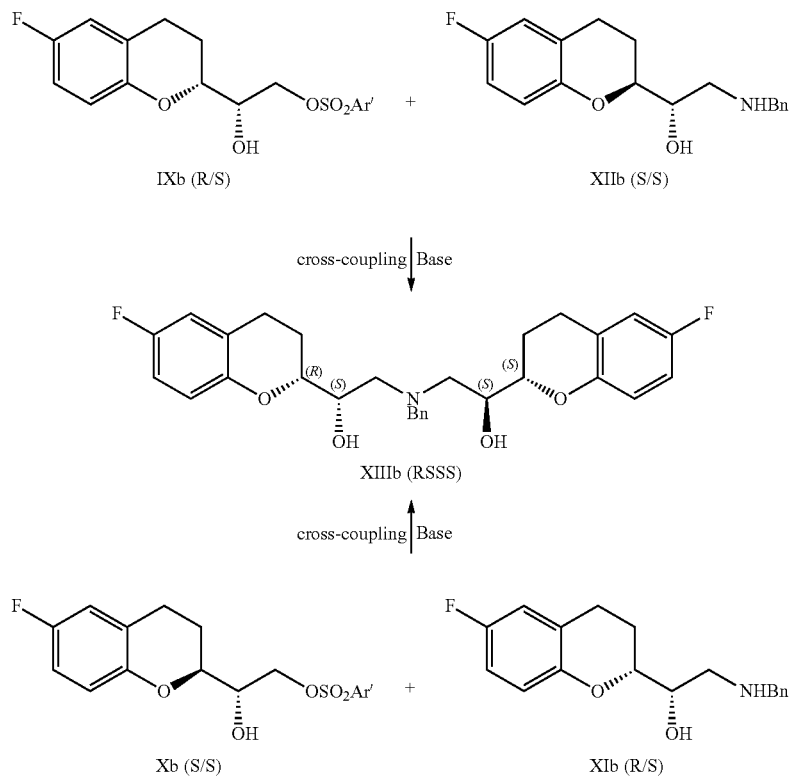

and optionally converting the intermediate compound XIIIb to the hydrochloride thereof, 8'') deprotecting the intermediate compound XIIIb to give L-Nebivolol (formula Ib),

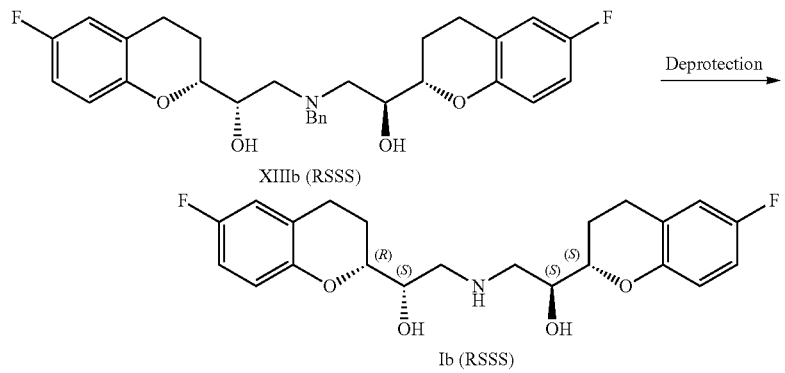

or converting the hydrochloride of the intermediate compound XIIIb to the intermediate compound XIIIb in free form by neutralization with base, followed by deprotection to give L-Nebivolol (formula Ib).

In an embodiment of preparing the compound of formula Ia, in step 3'), Sharpless asymmetric epoxidation is used, and the chiral catalyst used in the reaction is D-(−)-diethyl tartrate or D-(−)-diisopropyl tartrate, the reagent in the reaction is titanium tetraisopropoxide, tert-butyl hydroperoxide or cumene hydroperoxide, the solvent in the reaction is methylene dichloride, 3 A or 4 A molecular sieve is added into the reaction system, and the reaction temperature is −45° C. to 50° C.

In an embodiment of preparing the compound of formula Ib, in step 3''), Sharpless asymmetric epoxidation is used, and the chiral catalyst used in the reaction is L-(+)-diethyl tartrate or L-(+)-diisopropyl tartrate, the reagent in the reaction is titanium tetraisopropoxide, tert-butyl hydroperoxide or cumene hydroperoxide, the solvent in the reaction is methylene dichloride, 3 A or 4 A molecular sieve is added into the reaction system, and the reaction temperature is −45° C. to 50° C.

In the process for preparing the compound of formula Ia or Ib, in step 4') or step 4''), the deprotection can be carried out by the conventional methods in the field of organic chemistry to remove the hydroxy-protecting group, for example, by hydrogenolysis in the presence of catalyst to remove benzyl protective group, and cyclization is carried out in the presence of base; the catalyst used in the hydrogenolysis is Pd catalyst, such as Pd/C, Pd(OH)$_2$, Pd(OAc)$_2$, PdCl$_2$, Pd; the base used in the cyclization is selected from alkali metal and alkaline earth metal hydroxide or carbonate, alkoxide, or organic heterocyclic base, such as NaOH, KOH, K$_2$CO$_3$, NaOMe, DBU; or the deprotection and the cyclization are carried out by hydrogenolysis using Pd/C as catalyst under basic condition to simultaneously remove benzyl protective group and perform cyclization, to directly give the cyclization product.

In the process for preparing the compound of formula Ia or Ib, in step 5') or step 5''), the sulfonyl halide used in the sulfonylation can be arylsulfonyl chloride or substituted arylsulfonyl chloride or alkylsulfonyl chloride, such as p-toluenesulfonyl chloride, phenylsulfonyl chloride, p-halophenylsulfonyl chloride, p-nitrophenylsulfonyl chloride, o-nitrophenylsulfonyl chloride or methylsulfonyl chloride; no catalyst is used or an acylation catalyst is used in the reaction, and the catalyst used can be dialkyltin oxides, DMAP, such as dibutyltin oxide and 2,2-dibutyl-1,3,2-dioxastannolane; the base used in the reaction can be conventional organic base, such as pyridine, organic tertiary amine, such as triethylamine or diisopropylethylamine, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them, and the reaction temperature is −5 to 50° C.

In the process for preparing the compound of formula Ia or Ib, in step 6') or step 6''), alkylation of amine is carried out by reaction of benzyl amine with corresponding sulfonate, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them, and the reaction temperature is −25° C. to 150° C.

In the process for preparing the compound of formula Ia or Ib, in step 7') or step 7''), the base used in the cross-coupling reaction can be selected from inorganic base, such as K$_2$CO$_3$, Na$_2$CO$_3$, or organic tertiary amine, such as triethylamine or diisopropylethylamine, the solvent in the reaction is organic protic solvent, such as ethanol, propanol, isopropanol, or organic polar aprotic solvent, such as acetone, butanone, toluene, tetrahydrofuran, dimethylformamide, or a mixture of any two or more of these solvents, and the reaction temperature is −25° C. to 150° C.

In the process for preparing the compound of formula Ia or Ib, in step 8') or step 8''), the catalyst used in the deprotection reaction is Pd catalyst, such as Pd/C, Pd(OH)$_2$, Pd(OAc)$_2$, PdCl$_2$, Pd, the solvent in the reaction is alcohol, ester or ether, or a mixture of any two or more of these solvents, such as methanol or ethanol.

In an embodiment, the step of converting the intermediate compound XIIIa or the intermediate compound XIIIb to the hydrochloride thereof is carried out by adding hydrochloric acid to the intermediate compound, such as 1N hydrochloric acid, followed by crystallization and filtration to give the hydrochloride as solid.

In a preferred embodiment for preparing the compound of formula Ia or formula Ib, in step 4') or step 4''), the deprotection can be carried out by the conventional methods in the field of organic chemistry to remove the hydroxy-protecting group, for example, by hydrogenolysis in the presence of catalyst to remove benzyl protective group, and cyclization is carried out in the presence of base; the catalyst used in the hydrogenolysis is Pd catalyst, such as Pd/C, Pd(OH)$_2$, Pd(OAc)$_2$, PdCl$_2$, Pd; the base used in the cyclization is selected from alkali metal and alkaline earth metal hydroxide or carbonate, alkoxide, or organic heterocyclic base, such as NaOH, KOH, K$_2$CO$_3$, NaOMe, DBU; or the deprotection and the cyclization are carried out by hydrogenolysis using Pd/C as catalyst under basic condition to simultaneously remove benzyl protective group and perform cyclization, to directly give the cyclization product;

in step 5') or step 5"), the sulfonyl halide used in the sulfonylation can be arylsulfonyl chloride or substituted arylsulfonyl chloride or alkylsulfonyl chloride, such as p-toluenesulfonyl chloride, phenylsulfonyl chloride, p-halophenylsulfonyl chloride, p-nitrophenylsulfonyl chloride, o-nitrophenylsulfonyl chloride or methylsulfonyl chloride; and the catalyst used in the reaction can be dialkyltin oxides, DMAP, such as dibutyltin oxide and 2,2-dibutyl-1,3,2-dioxastannolane; the base used in the reaction can be conventional organic base, such as pyridine, organic tertiary amine, such as triethylamine or diisopropylethylamine, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them;

in step 6') or step 6"), alkylation of amine is carried out by reaction of benzyl amine with corresponding sulfonate, the solvent in the reaction is organic aprotic solvent, such as methylene dichloride, chloroform, methyltetrahydrofuran, tetrahydrofuran, pyridine, toluene, ethyl acetate, acetonitrile, DMF, DMA, or a mixture of any two or more of them;

in step 7') or step 7"), the base used in the cross-coupling reaction can be selected from inorganic base, such as K$_2$CO$_3$, Na$_2$CO$_3$, or organic tertiary amine, such as triethylamine or diisopropylethylamine, the solvent in the reaction is organic protic solvent, such as ethanol, propanol, isopropanol, or organic polar aprotic solvent, such as acetone, butanone, toluene, tetrahydrofuran, dimethylformamide, or a mixture of any two or more of these solvents;

in step 8') or step 8"), the catalyst used in the deprotection reaction is Pd catalyst, such as Pd/C, Pd(OH)$_2$, Pd(OAc)$_2$, PdCl$_2$, Pd, the solvent in the reaction is alcohol, ester or ether, or a mixture of any two or more of these solvents, such as methanol or ethanol.

In an embodiment, the step of converting the intermediate compound XIIIa or the intermediate compound XIIIb to the hydrochloride thereof is carried out by adding hydrochloric acid to the intermediate compound, such as 1N hydrochloric acid, followed by crystallization and filtration to give the hydrochloride as solid.

A skilled person in the art will understand that, in above process for preparation of the compound of formula Ia or formula Ib, the reaction product of any one of the above steps can be used as starting material to perform subsequent steps described above to prepare the compound of formula Ia or formula Ib. For example, the compounds of formula IXa and formula XIIa can be used as starting materials to perform steps 7') to 8') described above to obtain D-Nebivolol of formula Ia, or the compounds of formula IXb and formula XIIb can be used as starting materials to perform steps 7") to 8") described above to obtain L-Nebivolol of formula Ib.

In another aspect, the present invention also provides a mixture of D-Nebivolol (formula Ia) and L-Nebivolol (formula Ib) in any ratio,

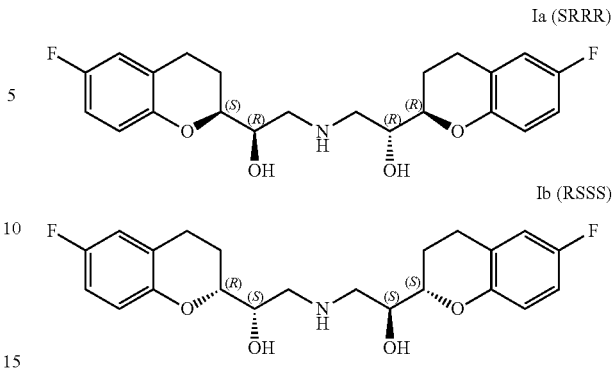

wherein D-Nebivolol (formula Ia) and L-Nebivolol (formula Ib) are prepared according to the above processes, respectively.

In another aspect, the present invention also provides a process for preparation of a mixture of D-Nebivolol (formula Ia) and L-Nebivolol (formula Ib) in any ratio, the process comprising:

(1) according to the processes described in the above steps 3') to 8') and steps 3") to 8"), preparing D-Nebivolol (formula Ia) and L-Nebivolol (formula Ib), respectively, and mixing them in any ratio; or (2) according to the processes described in the above steps 3') to 7') and steps 3") to 7"), preparing the hydrochloride of intermediate compound XIIIa and the hydrochloride of intermediate compound XIIIb, respectively, and mixing them in any ratio, neutralizing with base, and deprotecting the resulting mixture according to the method described in the step 8'); or (3) according to the processes described in the above steps 3') to 7') and steps 3") to 7"), preparing the hydrochloride of intermediate compound XIIIa and the hydrochloride of intermediate compound XIIIb, respectively, neutralizing them with base respectively to obtain free intermediate compound XIIIa and free intermediate compound XIIIb, mixing the two free intermediate compounds in any ratio, and deprotecting the resulting mixture according to the method described in the step 8').

In another aspect, the present invention provides the compound of formula IV1'

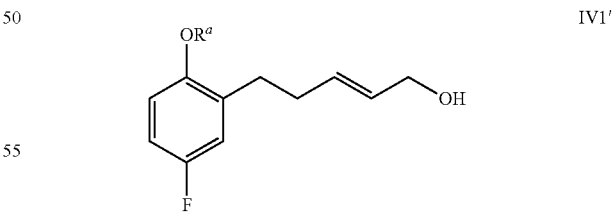

wherein $R^a$ is hydrogen or $R^a$ is hydroxy-protecting group, which is selected from aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl.

In another aspect, the present invention provides the compound of formula IV2'

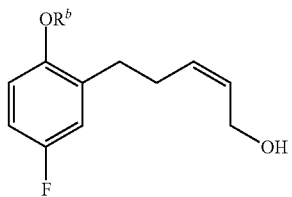

IV2' wherein $R^b$ is hydrogen or $R^b$ is hydroxy-protecting group, which is selected from aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl.

In another aspect, the present invention provides the compound of formula V' (2R*,3R*)

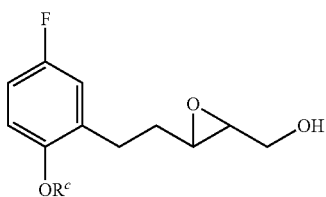

V' (2R*, 3R*)

wherein $R^c$ is hydrogen or $R^c$ is hydroxy-protecting group, which is selected from aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, wherein the compound V' is racemate, the relative configuration of which is represented by V' (2R*,3R*), which is a recemic mixture consisting of equimolar amounts of Va'(2R,3R) and the enantiomer Vb'(2S,3S), such as the compounds having the following formulae wherein R is benzyl:

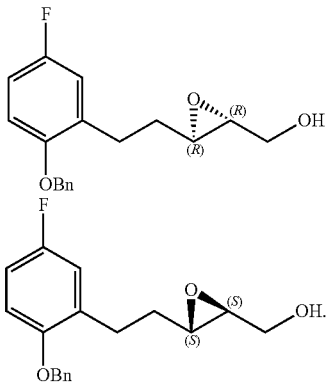

In another aspect, the present invention provides the compound of formula VI' (2R*,3S*)

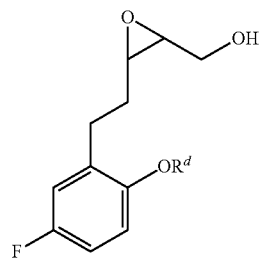

VI' (2R*, 3R*)

wherein $R^d$ is hydrogen or $R^d$ is hydroxy-protecting group, which is selected from aralkyl, alkoxyalkyl, allyl or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl, wherein the compound VI' is racemate, the relative configuration of which is represented by VI' (2R*,3S*), which is a recemic mixture consisting of equimolar amounts of VIa'(2R,3S) and the enantiomer VIb' (2S,3R), such as the compounds having the following formulae wherein $R^d$ is benzyl:

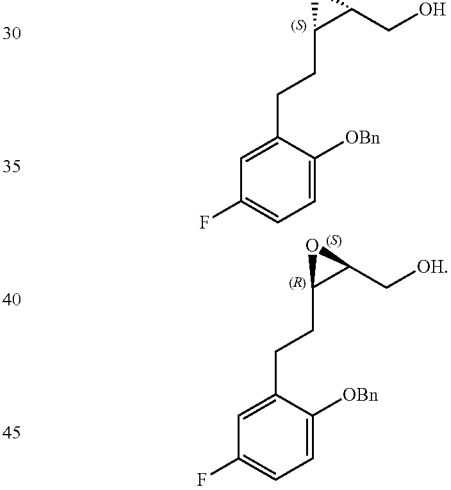

In another aspect, the present invention provides the compound of formula XI':

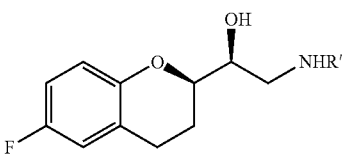

XI' wherein R' is substituted or unsubstituted aralkyl, C$_{1-6}$ alkoxycarbonyl or C$_{5-10}$ aralkoxycarbonyl, such as substituted or unsubstituted benzyl, tert-butyloxycarbonyl, benzyloxycarbonyl.

In another aspect, the present invention provides the compound of formula XII':

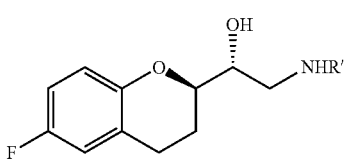

wherein R' is substituted or unsubstituted aralkyl, $C_{1-6}$ alkoxycarbonyl or $C_{5-10}$ aralkoxycarbonyl, such as substituted or unsubstituted benzyl, tert-butyloxycarbonyl, benzyloxycarbonyl.

In another aspect, the present invention provides the compound of formula XVI':

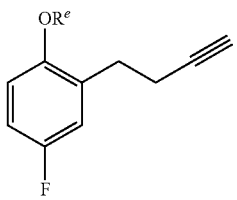

wherein $R^e$ is hydrogen or $R^e$ is hydroxy-protecting group, said hydroxy-protecting group being selected from alkyl, haloalkyl, aralkyl, alkoxyalkyl, benzoyl, benzoyl in which the phenyl ring has substituent(s), or silyl protective group, such as t-BuMe$_2$Si, t-BuPh$_2$Si, (i-Pr)$_3$Si, Et$_3$Si, methoxymethyl, benzyl or —CH$_2$Ar, wherein Ar is unsubstituted or substituted aryl, such as p-methoxyphenyl or halogen-substituted phenyl.

In an embodiment, the present invention also provides the following specific compounds for use in the synthesis of Nebivolol, selected from:
1-benzyloxy-2-bromomethyl-4-fluorobenzene,
4-[(2-benzyloxy-5-fluorophenyl)-butyn-1-yl]trimethylsilane,
1-(benzyloxy)-2-(butyn-3-yl)-4-fluorobenzene,
5-[2-(benzyloxy)-5-fluorophenyl]pent-2-yne-1-ol,
trans-5-[2-(benzyloxy)-5-fluorophenyl]pent-2-ene-1-ol,
(2R*,3R*)-3-[2-(benzyloxy)-5-fluorophenethyl]-2-hydroxymethyl-oxacyclopropane,
1-[6-fluoro-(2S*)-3,4-dihydro-2H-benzopyran-2-yl]-(1R*)-1,2-ethylene glycol,
cis-5-[2-(benzyloxy)-5-fluorophenyl]pent-2-ene-1-ol,
(2R*,3S*)-3-[2-(benzyloxy)-5-fluorophenethyl]-2-hydroxymethyl-oxacyclopropane,
1-[6-fluoro-(2R*)-3,4-dihydro-2H-benzopyran-2-yl]-(1R*)-1,2-ethylene glycol,
(S*,R*)-(+/−)-α-[(p-tolylsulfonyloxy)methyl]-(6-fluoro-2-chromanyl)-methanol,
(R*,R*)-(+/−)-α-[(p-tolylsulfonyloxy)methyl]-(6-fluoro-2-chromanyl)-methanol,
(S*,R*)-(+/−)-α-[(benzylamino)methyl]-(6-fluoro-2-chromanyl)-methanol,
(R*,R*)-(+/−)-α-[(benzylamino)methyl]-(6-fluoro-2-chromanyl)-methanol,
(2R,3R)-3-[2-(benzyloxy)-5-fluorophenethyl]-2-hydroxymethyl-oxacyclopropane,
(2S,3S)-3-[2-(benzyloxy)-5-fluorophenethyl]-2-hydroxymethyl-oxacyclopropane,
(2R,3S)-3-[2-(benzyloxy)-5-fluorophenethyl]-2-hydroxymethyl-oxacyclopropane,
(2S,3R)-3-[2-(benzyloxy)-5-fluorophenethyl]-2-hydroxymethyl-oxacyclopropane,
1-[6-fluoro-(2S)-3,4-dihydro-2H-benzopyran-2-yl]-(1R)-1,2-ethylene glycol,
1-[6-fluoro-(2R)-3,4-dihydro-2H-benzopyran-2-yl]-(1S)-1,2-ethylene glycol,
1-[6-fluoro-(2R)-3,4-dihydro-2H-benzopyran-2-yl]-(1R)-1,2-ethylene glycol,
1-[6-fluoro-(2S)-3,4-dihydro-2H-benzopyran-2-yl]-(1S)-1,2-ethylene glycol,
(S,R)-(+)-α-[(p-tolylsulfonyloxy)methyl]-(6-fluoro-2-chromanyl)-methanol,
(R,R)-(−)-α-[(p-tolylsulfonyloxy)methyl]-(6-fluoro-2-chromanyl)-methanol,
(R,S)-(−)-α-[(p-tolylsulfonyloxy)methyl]-(6-fluoro-2-chromanyl)-methanol,
(S,S)-(+)-α-[(p-tolylsulfonyloxy)methyl]-(6-fluoro-2-chromanyl)-methanol,
(S,R)-[(benzylamino)methyl]-(6-fluoro-2-chromanyl)-methanol, or
(R,S)-[(benzylamino)methyl]-(6-fluoro-2-chromanyl)-methanol.

EXAMPLES

The processes of the present invention will be further illustrated by the following examples. It should be understood that the following examples are provided to help further understand the present invention, not intended to limit the scope of the present invention in any manner.

The abbreviations used in the present application have the following meanings.

Abbreviations

Boc tert-butyloxycarbonyl
DEAD diethyl azodicarboxylate
DIPEA diisopropylethylamine
DMF dimethylformamide
DMA dimethylacetamide
EtOAc ethyl acetate
TBAF tetrabutylammonium fluoride
THF tetrahydrofuran
TLC thin layer chromatography
t-Bu(Me)$_2$Si tert-butyldimethylsilyl
TBS tert-butyldimethylsilyl
TBSCl tert-butyldimethylchlorosilane Example 1: Preparation of 1-benzyloxy-2-bromomethyl-4-fluorobenzene (Compound XIV, wherein R is Benzyl)

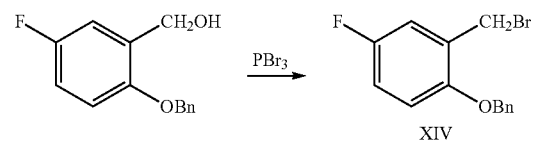

The starting material 2-benzyloxy-5-fluorobenzenemethanol used in this Example can be prepared from the known compound 2-hydroxy-5-fluorobenzenemethanol (Medicinal Chemistry Letters, 2010, vol. 1, #7, p. 321-325, References, Bioorganic & Medicinal Chemistry, 2006, vol. 14, #6, p. 2022-2031).

5.14 g (22 mmol) 2-benzyloxy-5-fluorobenzene-methanol was dissolved in 180 mL anhydrous diethyl ether, to which a solution of PBr₃ (2.3 mL, 24.4 mmol) in 20 mL anhydrous diethyl ether was added dropwise at 0° C. The temperature was warmed to room temperature and the reaction was carried out for 2 hours. TLC indicated the reaction was completed.

Work-up: 50 mL water was added. After different layers appear, organic layer was removed. Water layer was extracted with DCM (50 mL×3). Organic phases were combined, and washed with saturated sodium bicarbonate solution, water and saturated sodium chloride solution. The resulting organic phase was dried with anhydrous sodium sulfate, filtered, and concentrated, to give 6 g crude product. The crude product obtained was recrystallized from PE/Et₂O, to obtain 5.9 g of desired product as crystal. Total yield is 91.2%.

¹H-NMR (400 MHz, CDCl₃) δ 7.33~7.47 (m, 5H), 7.06~7.09 (dd, J=7.6, 2.8 Hz, 1H), 6.91~6.96 (m, 1H), 6.82~6.86 (dd, J=8.8, 4.4 Hz, 1H), 5.11 (s, 2H), 4.53 (s, 2H)

Example 2: Preparation of 4-[(2-benzyloxy-5-fluorophenyl)-butyn-1-yl]trimethylsilane Compound XV, Wherein R is Benzyl)

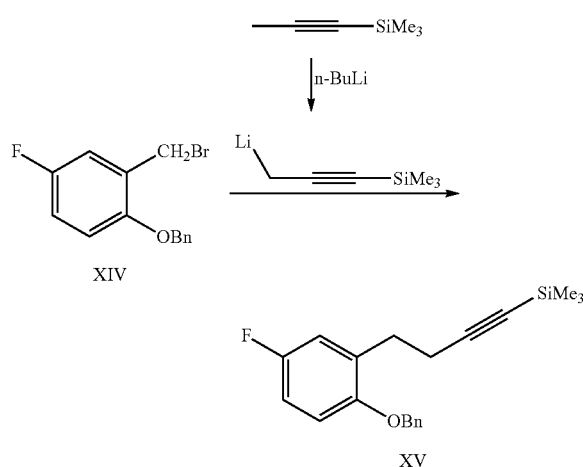

2.4 mL (16.1 mmol) trimethylsilylpropyne was added to 40 mL anhydrous THF. The mixture was cooled to −23° C., to which 2.5 M n-BuLi 7.7 mL (19.3 mmol) was added dropwise. After the addition, the solution was stirred at this temperature for 2 hours, until the reaction solution became orange red. Then the temperature was decreased to below −100° C. A solution of 3.5 g (11.9 mmol) compound XIV (wherein R is benzyl) in 5 mL anhydrous THF was added. After that, the reaction was carried out for 1 hour. TLC indicated the reaction was completed.

Work-up: The reaction was terminated with 10% saturated ammonium chloride solution. After different layers appear, water layer was extracted with diethyl ether (100 mL×2). Organic phases were combined, washed with saturated ammonium chloride solution, dried with anhydrous sodium sulfate, filtered, and concentrated. After column chromatography (PE/Et₂O=100:1), 3.79 g pure product was obtained. The yield is 97.6%.

¹H-NMR (400 MHz, CDCl₃) δ 7.38~7.42 (m, 5H), 6.93~6.96 (dd, J=8.8, 2.4 Hz, 1H), 6.78~6.85 (m, 2H), 5.05 (s, 2H), 2.86~2.90 (t, J=7.2 Hz, 2H), 2.50~2.53 (t, J=7.2 Hz, 2H), 1.96 (s, 1H), 0.15 (s, 9H)

Example 3: Preparation of 1-(benzyloxy)-2-(butyn-3-yl)-4-fluorobenzene (Compound XVI, wherein R is Benzyl)

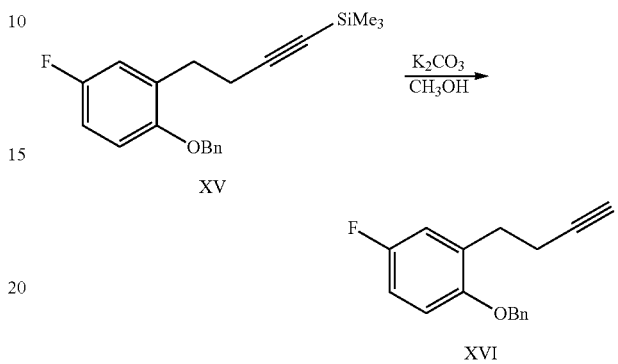

1.15 g (3.52 mmol) compound XV (wherein R is benzyl) was dissolved in 20 ml MeOH, to which 0.5 g (3.6 mmol) K₂CO₃ was added. The reaction mixture was stirred at room temperature for 3 hours. The solvent was evaporated under reduced pressure. The residue was extracted with EtOAc, washed with water and saturated NaCl solution, dried with anhydrous Na₂SO₄, and filtered. After the filtrate was evaporated to dryness, 0.87 g colorless oil was obtained. After filtration with short silica gel column and elution with PL/EtOAc (100/2), 0.85 g colorless oil was obtained.

¹H-NMR (400 MHz, CDCl₃) δ 7.33~7.42 (m, 5H), 6.93~6.96 (dd, J=9.6, 2.8 Hz, 1H), 6.81~6.86 (m, 2H), 5.05 (s, 2H), 2.86~2.90 (t, J=7.2 Hz, 2H), 2.47~2.51 (t, J=7.2 Hz, 2H), 1.96 (s, 1H)

Example 4: Preparation of 5-[2-(benzyloxy)-5-fluorophenyl]pent-2-yne-1-ol (Compound III, wherein R is Benzyl)

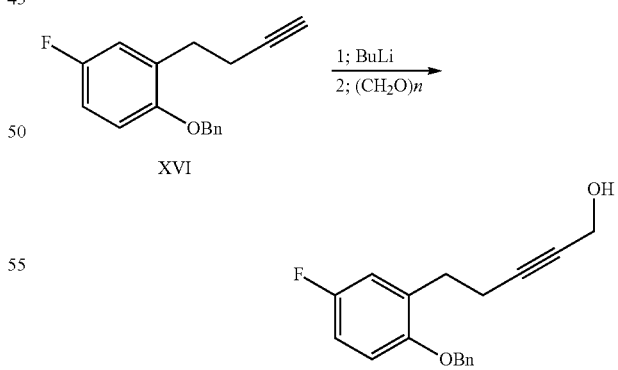

1.49 g (5.6 mmol) compound XVI (wherein R is benzyl) was dissolved in 20 ml THF, cooled to −100° C., to which 2.9 ml 2.4 M BuLi (6.9 mmol) was added dropwise. After the addition was completed, the mixture was stirred at −100° C. for 30 min, and warmed to 0° C., to which 0.6 g (20 mmol) (CH₂O)ₙ was added. After the addition was completed, the reaction mixture was stirred at 0° C. to room temperature for 2.5 hours. Saturated NH₄Cl solution was added to terminate the reaction. Organic phase was separated, and water layer was extracted with Et₂O twice. The extract solutions were combined, washed with water, washed with saturated NaCl solution, dried with anhydrous Na₂SO₄. The mixture was filtered and the resulting filtrate was evaporated to dryness. After purification on short silica gel column by eluting with petroleum ether/EtOAc (4/1), 1.51 g colorless oil was obtained.

¹H-NMR (400 MHz, CDCl₃) δ 7.33~7.42 (m, 5H), 6.93~6.96 (dd, J=9.6, 2.8 Hz, 1H), 6.81~6.86 (m, 2H), 5.05 (s, 2H), 2.86~2.90 (t, J=7.2 Hz, 2H), 2.47~2.51 (t, J=7.2 Hz, 2H), 1.96 (s, 1H)

HR-MS (ESI) calculated C18H18O2F (M+H)+: 285.1285, found 285.1290.

Example 4': Preparation of 5-[2-(benzyloxy)-5-fluorophenyl]pent-2-yne-1-ol (Compound III, Wherein R is Benzyl)

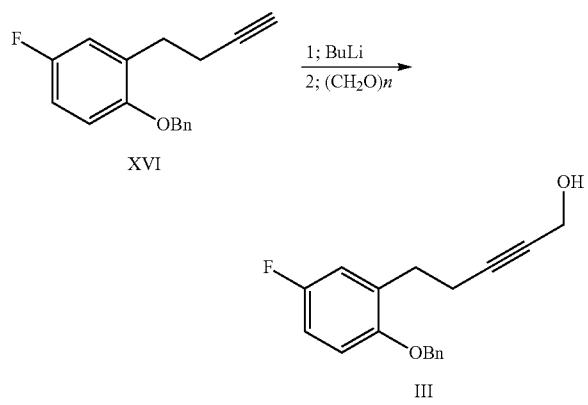

1.49 g (5.6 mmol) compound XVI (wherein R is benzyl) was dissolved in 20 ml THF, cooled to −100° C., to which 2.9 ml 2.4M BuLi (6.9 mmol) was added. After the addition was completed, the solution was stirred at −100° C. for 30 min, and then warmed to 0° C., to which 0.6 g (20 mmol) (CH₂O)ₙ was added. After the addition was completed, the reaction mixture was stirred at 0° C. to room temperature for 2.5 h. Saturated NH₄Cl solution was added to terminate the reaction. Organic phase was separated, and water layer was extracted with Et₂O twice. The extract solutions were combined, washed with water, washed with saturated NaCl solution, dried with anhydrous Na₂SO₄. The mixture was filtered, the resulting filtrate was evaporated to dryness and oil was obtained. 10 ml n-hexane was added to the oil. The resulting mixture was stirred, cooled to −20° C. Crystal precipitated. After filtration, 1.2 g white solid with purity of 98% was obtained.

¹H-NMR (400 MHz, CDCl₃) δ 7.33~7.42 (m, 5H), 6.93~6.96 (dd, J=9.6, 2.8 Hz, 1H), 6.81~6.86 (m, 2H), 5.05 (s, 2H), 2.86~2.90 (t, J=7.2 Hz, 2H), 2.47~2.51 (t, J=7.2 Hz, 2H), 1.96 (s, 1H)

HR-MS (ESI) calculated C18H18O2F (M+H)+: 285.1285, found 285.1290.

Example 5: Preparation of trans-5-[2-(benzyloxy)-5-fluorophenyl]pent-2-ene-1-ol (Compound IV-1, Wherein R is Benzyl)

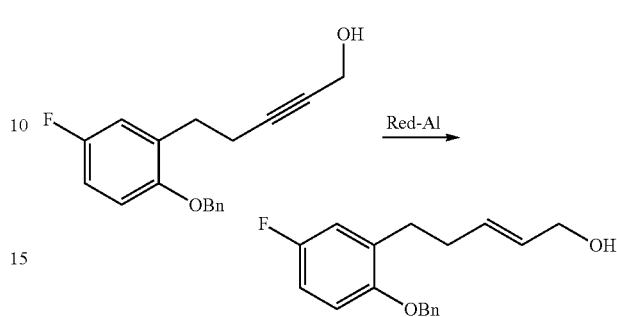

1.05 g (3.6 mmol) compound III (wherein R is benzyl) was dissolved in 25 ml THF, cooled in the ice bath, to which 2.1 ml 3.4 M (7.1 mmol) Red-Al was added. After the addition was completed, The reaction mixture was stirred at room temperature overnight (TLC indicated Rf value of the product is the same as the starting material under the condition of PL/EtOA=4/1). In the next day, saturated potassium sodium tartrate solution (about 20 ml) was added dropwise carefully to terminate the reaction. Organic phase was separated, and water layer was extracted with 20 ml x 2 EtOAc. The extract solutions were combined, washed with 1N HCl, washed with water, washed with saturated NaCl solution, dried with anhydrous Na₂SO₄. The mixture was filtered and the resulting filtrate was evaporated to dryness, yielding 1.0 g of product (light yellow oil).

¹H-NMR (400 MHz, CDCl₃) δ 7.32~7.42 (m, 5H), 6.85~6.87 (d, J=8.4 Hz, 1H), 6.81~6.83 (m, 2H), 5.61~5.74 (m, 2H), 5.04 (s, 2H), 4.05~4.07 (d, J=5.6 Hz, 2H), 2.71~2.75 (t, J=7.6 Hz, 2H), 2.33~2.38 (q, 2H), 1.39 (s, 2H).

HR-MS (ESI) calculated C18H20O2F (M+H)⁺: 287.1448, found 287.1441.

Example 5': Preparation of trans-5-[2-(benzyloxy)-5-fluorophenyl]pent-2-ene-1-ol (Compound IV-1, Wherein R is Benzyl)

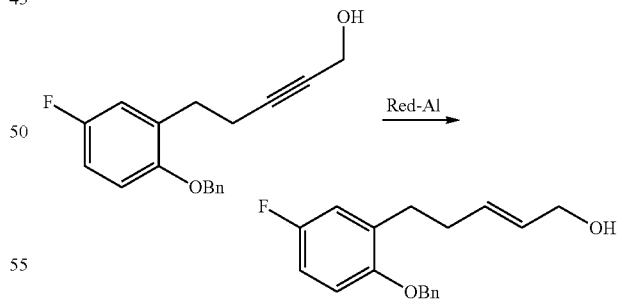

1.05 g (3.6 mmol) compound III (wherein R is benzyl) was dissolved in 25 ml THF, cooled in the ice bath, to which 2.1 ml 3.4 M (7.1 mmol) Red-Al was added. After the addition was completed, the reaction mixture was stirred at room temperature overnight (TLC indicated Rf value of the product is the same as the starting material under the condition of PL/EtOA=4/1). In the next day, saturated potassium sodium tartrate solution (about 20 ml) was added dropwise carefully to terminate the reaction. Organic phase was separated, and water layer was extracted with 20 ml x 2 EtOAc. The extract solutions were combined, washed with 1N HCl, washed with water, washed with saturated NaCl solution, dried with anhydrous $Na_2SO_4$. The mixture was filtered and the resulting filtrate was evaporated to dryness, yielding oil. To the oil, 8 ml n-hexane was added. The resulting mixture was stirred, cooled to −20° C. Crystal precipitated. After filtration, 0.7 g off-white solid with purity of 99% was obtained, melting point: 18-20° C.

$^1$H-NMR (400 MHz, $CDCl_3$) δ 7.32~7.42 (m, 5H), 6.85~6.87 (d, J=8.4 Hz, 1H), 6.81~6.83 (m, 2H), 5.61~5.74 (m, 2H), 5.04 (s, 2H), 4.05~4.07 (d, J=5.6 Hz, 2H), 2.71~2.75 (t, J=7.6 Hz, 2H), 2.33~2.38 (q, 2H), 1.39 (s, 2H).

HR-MS (ESI) calculated C18H20O2F (M+H)$^+$: 287.1448, found 287.1441.

Example 6: Preparation of (2R*,3R*)-3-[2-(benzyloxy)-5-fluorophenethyl]-2-hydroxymethyl-oxacyclopropane (Compound V, Wherein R is Benzyl)

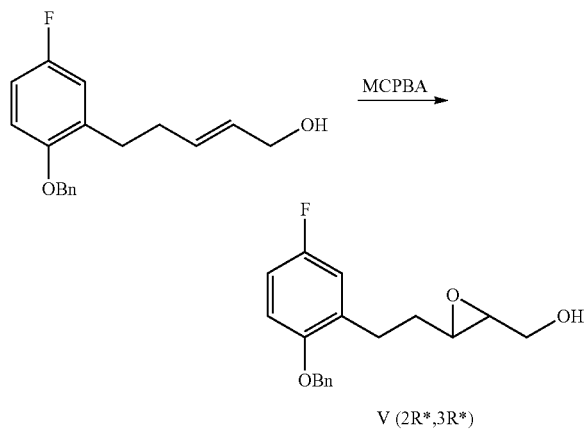

1.06 g (4 mmol) compound IV-1 (wherein R is benzyl) was dissolved in 20 ml DMC, and 1.01 g 75% MCPBA (4.4 mmol) was added with stirring. After the addition was completed, the reaction mixture was stirred at room temperature for 4 h. The reaction solution was diluted with DMC, sequentially washed with 5% NaOH twice, washed with water, dried with anhydrous $Na_2SO_4$. After filtration, the filtrate was evaporated to dryness, yielding 1.08 g light yellow oil (90%).

$^1$H-NMR (400 MHz, $CDCl_3$) δ 7.32~7.41 (m, 5H), 6.88~6.90 (d, J=8.4 Hz, 1H), 6.83~6.85 (m, 2H), 5.04 (s, 2H), 3.80~3.83 (d, J=12.5 Hz, 1H), 3.51~3.57 (m, 1H), 2.97~2.99 (t, J=5.6 Hz, 1H), 2.75~2.85 (m, 3H), 1.84~1.91 (m, 2H).

Example 7: Preparation of 1-[6-fluoro-(2S*)-3,4-dihydro-2H-benzopyran-2-yl]-(1R*)-1,2-ethylene glycol (Compound VII)

Method One:

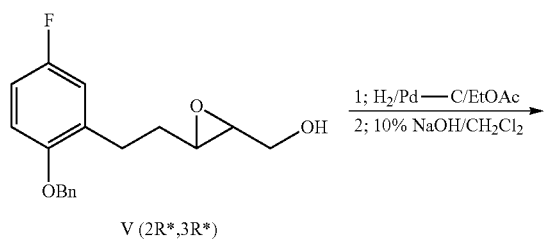

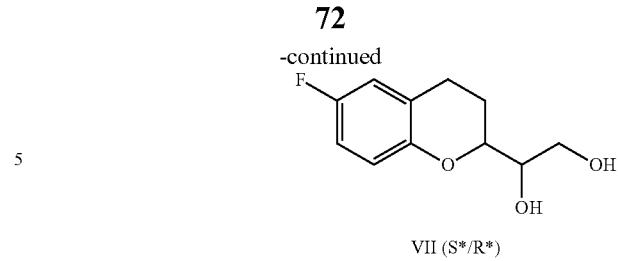

1.08 g compound V (wherein R is benzyl) was dissolved in 20 ml EtOAc, to which 0.2 g 10% Pd/C was added. The reaction mixture was subjected to hydrogenation under ordinary pressure at room temperature overnight. After filtration, the filtrate was evaporated to dryness, yielding 0.85 g oil. The oil was dissolved in 20 ml DMC, cooled in ice bath, to which 10 ml 10% NaOH—NaCl solution was added. The resulting solution was stirred in ice bath for 30 min. The reaction mixture was warmed to room temperature and stirred at room temperature for 3 h. Organic phase was separated, and water layer was extracted with 10 ml DMC. The extract solutions were combined, washed with water, dried with anhydrous $Na_2SO_4$. After purification on short silica gel column by eluting with PL/EtOAc (1/1), 0.71 g white solid was obtained (95%).

Method Two:

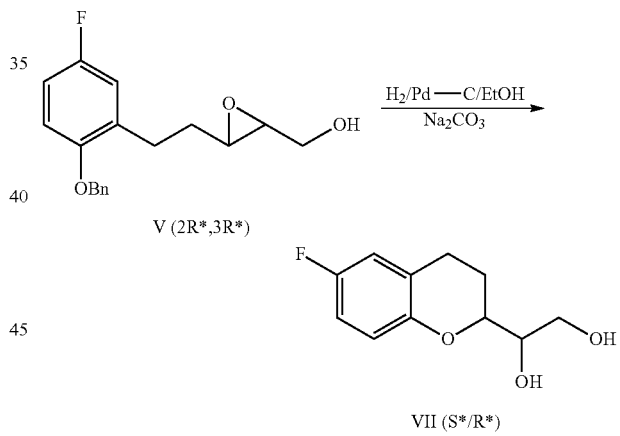

To 1.5 g compound V (wherein R is benzyl), 25 ml anhydrous ethanol, 200 mg 10%/Pd/C and 100 mg anhydrous $Na_2CO_3$ were added. The reaction mixture was subjected to hydrogenation under ordinary pressure until no hydrogen was absorbed (about 1.5 hours), and then was stirred with heating at 60° C. for 2.5 hours. The mixture was filtered and the resulting filtrate was evaporated to dryness, yielding 0.95 g white solid.

$^1$H-NMR (400 MHz, $CDCl_3$) δ 6.70~6.80 (m, 3H), 3.99~4.02 (dd, J=10.4, 3.6 Hz, 1H), 3.82~3.89 (m, 3H), 2.75~2.85 (m, 2H), 2.11~2.16 (m, 1H), 1.82~1.90 (m, 1H)

HR-MS (EI) calculated $C_{11}H_{13}O_3F$ (M)$^+$: calculated 212.0849, found 212.0851.

Example 8: Preparation of cis-5-[2-(benzyloxy)-5-fluorophenyl]pent-2-ene-1-ol (Compound IV-2, Wherein R is Benzyl)

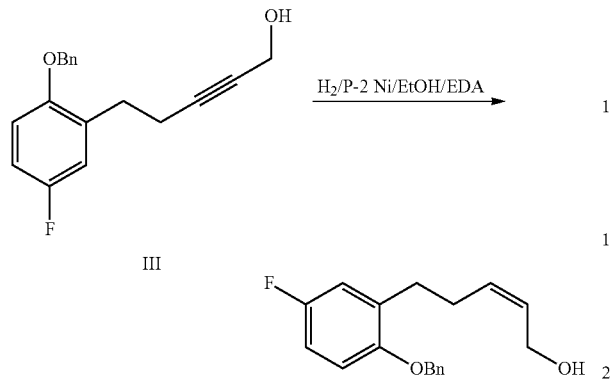

A 250 ml round bottom flask was charged with Ni (OAc)$_2$·4H$_2$O (42 0 mg, 1.7 mmol), evacuated to vacuum, and argon was introduced. 20 ml 95% ethanol which had been degassed was added. Sodium borohydride (100 mg, 2.6 mmol) was added to the reaction mixture with stirring under argon. The reaction mixture was stirred for 15 min, and the reaction mixture became black. Then ethylenediamine (0.5 ml, 7.5 mmol) was added. The reaction mixture was stirred for 5 min and NaOH solution (2 M, 6 0 μL, 0.1 mmol) which had been degassed was added. The compound III (wherein R is benzyl) (3.2 g, 11.3 mmol) was dissolved in 10 ml 95% ethanol, and the resulting solution was added dropwise to the reaction mixture. After that, argon used in the reaction was replaced with hydrogen and the reaction was carried out at room temperature for 18 h. TLC indicated the reaction was completed.

Work-up: hydrogen used in the reaction was replaced with argon. After removing hydrogen, the reaction mixture was filtered with Celite. The filter cake was washed with 100 ml ethyl acetate and water (3×20 ml). Organic phase was dried with anhydrous sodium sulfate. The mixture was filtered and the resulting filtrate was evaporated to dryness, yielding 3.15 g product. The yield is 97%.

$^1$HNMR (400 MHz, CDCl$_3$) δ 7.34~7.43 (m, 5H), 6.80~6.86 (m, 3H), 5.53~5.62 (m, 2H), 5.04 (s, 2H), 3.97~4.00 (d, J=12 Hz, 2H), 2.63~2.68 (t, J=8 Hz, 2H), 2.35~2.40 (q, 2H), 1.27 (bs, 1H).

HR-MS (ESI) calculated C18H20O2F (M+H)+: 287.1448, found 287.1441.

Example 8': Preparation of cis-5-[2-(benzyloxy)-5-fluorophenyl]pent-2-ene-1-ol (Compound IV-2, Wherein R is Benzyl)

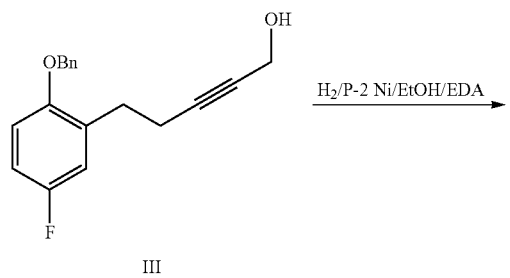

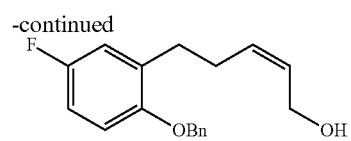

A 250 ml round bottom flask was charged with Ni (OAc)$_2$·4H$_2$O (42 0 mg, 1.7 mmol), evacuated to vacuum, and argon was introduced. 20 ml 95% ethanol which had been degassed was added. Sodium borohydride (100 mg, 2.6 mmol) was added to the reaction mixture with stirring under argon. The reaction mixture was stirred for 15 min, and the reaction mixture became black. Then ethylenediamine (0.5 ml, 7.5 mmol) was added. The reaction mixture was stirred for 5 min and NaOH solution (2 M, 6 0 μL, 0.1 mmol) which had been degassed was added. The compound III (wherein R is benzyl) (3.2 g, 11.3 mmol) was dissolved in 10 ml 95% ethanol, and the resulting solution was added dropwise to the reaction mixture. After that, argon used in the reaction was replaced with hydrogen and the reaction was carried out at room temperature for 18 h. TLC indicated the reaction was completed.

Work-up: hydrogen used in the reaction was replaced with argon. After removing hydrogen, the reaction mixture was filtered with Celite. The filter cake was washed with 100 ml ethyl acetate and water (3×20 ml). Organic phase was dried with anhydrous sodium sulfate. The mixture was filtered and the resulting filtrate was evaporated to dryness, yielding oil. To the oil, 30 ml n-hexane was added. The resulting mixture was stirred, cooled to −20° C. Crystal precipitated. After filtration, 2.7 g off-white solid with purity of 99% was obtained, melting point: 32-34° C.

$^1$HNMR (400 MHz, CDCl$_3$) δ 7.34~7.43 (m, 5H), 6.80~6.86 (m, 3H), 5.53~5.62 (m, 2H), 5.04 (s, 2H), 3.97~4.00 (d, J=12 Hz, 2H), 2.63~2.68 (t, J=8 Hz, 2H), 2.35~2.40 (q, 2H), 1.27 (bs, 1H).

HR-MS (ESI) calculated C18H20O2F (M+H)+: 287.1448, found 287.1441.

Example 9: Preparation of (2R*,3S*)-3-[2-(benzyloxy)-5-fluorophenethyl]-2-hydroxymethyl-oxacyclopropane (Compound VI, Wherein R is Benzyl)

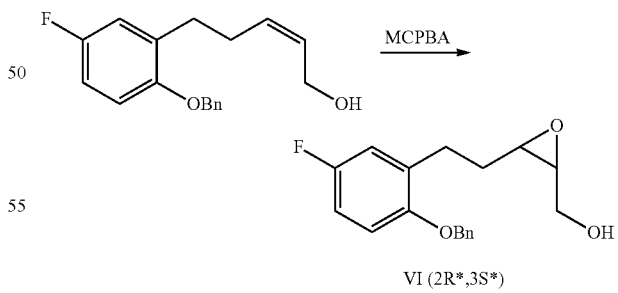

According to the method similar to Example 6, compound IV-2 (wherein R is benzyl) was used as starting material to obtain compound VI.

$^1$H-NMR (400 MHz, CDCl$_3$) δ 7.34~7.41 (m, 5H), 6.88~6.90 (d, J=8.4 Hz, 1H), 6.84~6.86 (m, 2H), 5.03 (s, 2H), 3.48~3.56 (m, 2H), 3.03~3.09 (m, 2H), 2.71~2.87 (m, 2H), 1.89~1.96 (m, 1H), 1.75~1.83 (m, 1H).

Example 10: Preparation of 1-[6-fluoro-(2R*)-3,4-dihydro-2H-benzopyran-2-yl]-(1R*)-1,2-ethylene glycol (Compound VIII)

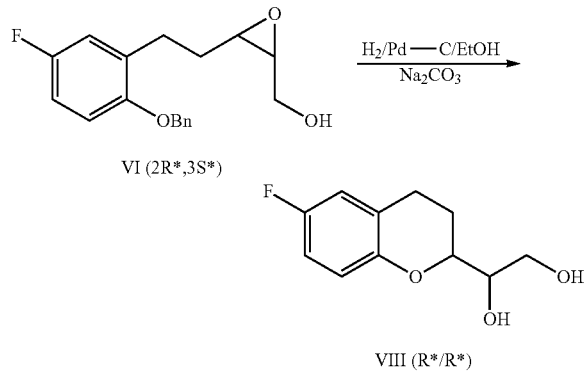

According to the methods which are the same as the two methods of Example 7, compound VI (wherein R is benzyl) was used as starting material to obtain compound VIII.

$^1$H-NMR (400 MHz, CDCl$_3$) δ 6.73~6.81 (m, 3H), 4.04~4.07 (m, 1H), 3.81~3.85 (m, 2H), 3.76~3.76 (m, 1H) 2.84~2.86 (m, 1H), 2.74~2.79 (m, 1H), 1.78~2.02 (m, 2H), 2.04 (bs, 2H)

HR-MS (EI) calculated C$_{11}$H$_{13}$O$_3$F (M)$^+$: calculated 212.0849, found 212.0844.

Example 11: Preparation of (S*,R*)-(+/−)-α-[(p-tolylsulfonyloxy)methyl]-(6-fluoro-2-chromanyl)-methanol (Compound IX)

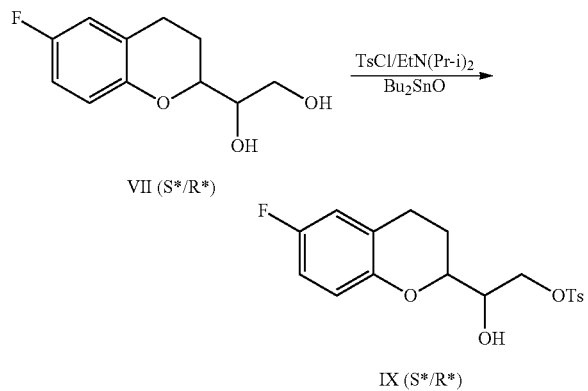

4.24 g (20 mmol) compound VII was suspended in 100 ml toluene, to which 0.5 g (2 mmol) dibutyltin oxide (Bu$_2$SnO) was added. The mixture was stirred at room temperature for 1 h, and then diisopropylethylamine (3.95 ml, 24 mmol) and 3.99 g (21 mmol) p-methylphenylsulfonyl chloride (TsCl) were added to the mixture. The reaction mixture was stirred at room temperature overnight. In the next day, the reaction mixture was washed with 2N HCl, washed with water, dried with anhydrous Na$_2$SO$_4$. After purification on short silica gel column by eluting with PL/EtOAc (3/1), 6.89 g white solid was obtained (94%).

$^1$H-NMR (400 MHz, CDCl$_3$) δ 7.80~7.82 (d, J=7.6 Hz, 2H), 7.34~7.35 (d, J=7.6 Hz, 2H), 6.7 (s, 2H), 6.58~6.61 (m, 1H), 4.36~4.39 (d, J=10.4 Hz, 1H), 4.21~4.23 (m, 1H), 3.91 (s, 2H), 2.75~2.8 (m, 2H), 2.45 (s, 3H), 2.16~2.19 (m, 1H), 1.75~1.79 (m, 1H)

HR-MS (ESI) calculated C$_{18}$H$_{19}$O$_5$FNaS(M+Na)$^+$: calculated 389.0829, found 389.0822.

Example 12: Preparation of (R*,R*)-(+/−)-α-[(p-tolylsulfonyloxy)methyl]-(6-fluoro-2-chromanyl)-methanol (Compound X)

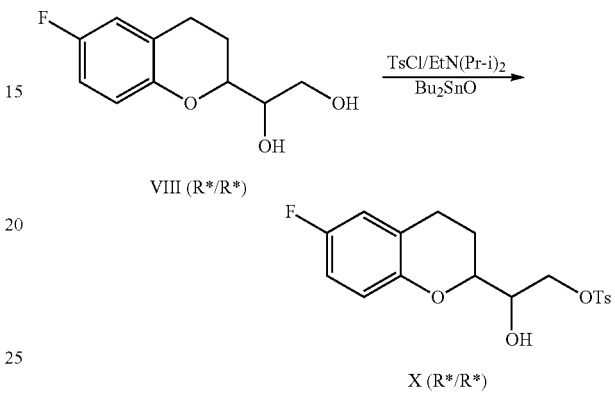

4.24 g (20 mmol) compound VIII was suspended in 100 ml toluene, to which 0.5 g (2 mmol) dibutyltin oxide (Bu$_2$SnO) was added. The mixture was stirred at room temperature for 1 h, and then diisopropylethylamine (3.95 ml, 24 mmol) and 3.99 g (21 mmol) p-methylphenylsulfonyl chloride (TsCl) were added to the mixture. The reaction mixture was stirred at room temperature overnight. The reaction mixture was washed with 2 N HCl, washed with water, dried with anhydrous Na$_2$SO$_4$. After purification on short silica gel column by eluting with PL/EtOAc (3/1), 7.07 g product was obtained as colorless syrup (98%).

$^1$H-NMR (400 MHz, CDCl$_3$) δ 7.80~7.82 (d, J=8.0 Hz, 2H), 7.33~7.35 (d, J=8.0 Hz, 2H), 6.73~6.79 (m, 2H), 6.64~6.67 (m, 1H), 4.21~4.22 (d, J=5.6 Hz, 2H), 4.0~4.02 (m, 1H), 3.91~3.95 (m, 1H), 2.72~2.87 (m, 2H), 2.44 (s, 3H), 1.93~1.95 (m, 2H)

HR-MS (ESI) calculated C$_{18}$H$_{19}$O$_5$FNaS(M+Na)$^+$: calculated 389.0829, found 389.0823.

Example 13: Preparation of (S*,R*)-(+/−)-α-[(benzylamino)methyl]-(6-fluoro-2-chromanyl)-methanol (Compound XI)

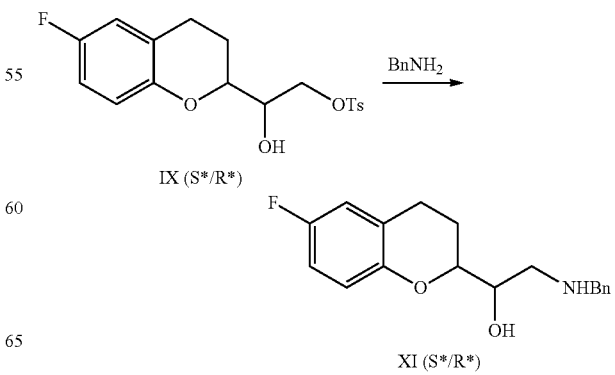

1.83 g (5 mmol) compound IX was dissolved in 20 ml THF, to which 2.72 ml benzyl amine was added. The reaction mixture was heated under reflux for 16 hours (TLC indicated the spot of starting material disappeared), and evaporated under reduced pressure to dryness. 10% $Na_2CO_3$ was added to the residue, and the resulting solution was extracted with EtOAc for three times. The extract solutions were combined, washed with 10% $Na_2CO_3$, washed with water, washed with saturated NaCl solution, and dried with anhydrous $Na_2SO_4$. After filtration, the filtrate was evaporated under reduced pressure to remove EtOAc. 20 ml cyclohexane was added to the residue and white crystal precipitated. After filtration, 1.25 g white solid was obtained.

$^1$H-NMR (400 MHz, CDCl$_3$) δ 7.28~7.36 (m, 5H), 6.6~6.8 (m, 3H), 3.85~3.89 (m, 3H), 3.74~3.81 (m, 1H), 2.98~3.02 (dd, J=4.12 Hz, 1H), 2.73~2.86 (m, 3H), 2.12~2.15 (m, 1H), 1.76~1.86 (m, 1H)

HR-MS (ESI) calculated $C_{18}H_{21}O_2FN$ (M+H)$^+$: calculated 302.1550, found 302.1546.

Example 14: Preparation of (R*,R*)-(+/−)-α-[(benzylamino)methyl]-(6-fluoro-2-chromanyl)-methanol (Compound XII)

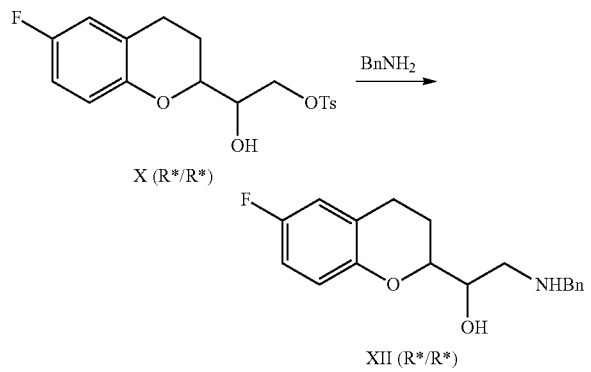

1.95 g (5.3 mmol) compound X was dissolved in 20 ml THF, to which 2.72 ml benzyl amine was added. The reaction mixture was heated under reflux for 16 hours (TLC indicated the spot of starting material disappeared), and evaporated under reduced pressure to dryness. 10% $Na_2CO_3$ was added to the residue, and the resulting solution was extracted with EtOAc for three times. The extract solutions were combined, washed with 10% $Na_2CO_3$, washed with water, washed with saturated NaCl solution, and dried with anhydrous $Na_2SO_4$. After filtration, the filtrate was evaporated under reduced pressure to remove EtOAc. 20 ml cyclohexane was added to the residue and 0.91 g white crystal precipitated.

$^1$H-NMR (400 MHz, CDCl$_3$) δ 7.28~7.38 (m, 5H), 6.7~6.8 (m, 3H), 3.86~3.95 (m, 4H), 2.91~2.92 (d, J=5.6 Hz, 2H), 2.75~2.84 (m, 2H), 1.91~1.94 (m, 2H)

Example 15: Preparation of N-benzyl-(+/−)-Nebivolol (Compound XIII)

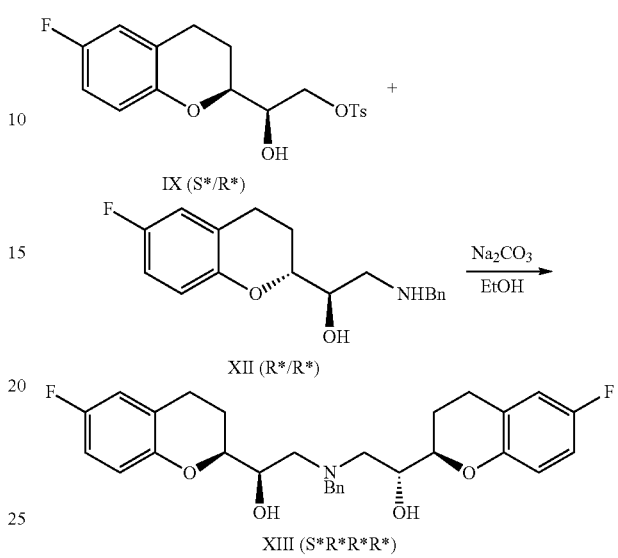

1.19 g (3.2 mmol) compound IX and 0.94 g (3.12 mmol) compound XII was dissolved in 15 ml EtOH, to which 0.5 g solid anhydrous sodium carbonate was added. The reaction mixture was heated under reflux with stirring for 16 hours, and evaporated under reduced pressure to dryness. 50 ml water was added to the residue and the resulting solution was extracted with EtOAc twice. The extract solutions were combined, washed with saturated NaCl solution, dried with anhydrous $Na_2SO_4$. After filtration, the filtrate was evaporated under reduced pressure to dryness, to give 1.59 g product as syrup. 25 ml isopropanol was added to the product and heated to dissolve it. 0.5 g oxalic acid (FW=126) was added. The resulting solution was heated with stirring for 20 min, cooled, placed at room temperature for 5 hours, filtered, dried by oven, to give 1.59 g white solid. The resulting product was recrystallized from ethanol twice to yield 0.69 g compound XIII as oxalate. The resulting product was suspended in 20 ml methylene dichloride, to which 10 ml 10% sodium carbonate was added. The mixture was stirred at room temperature for 25 minutes, organic phase was separated, washed with water, and dried with anhydrous $Na_2SO_4$. After filtration, the filtrate was evaporated under reduced pressure to dryness, to yield 0.58 g free base (compound XIII).

$^1$HNMR (500 MHz, CDCl$_3$) δ 7.27~7.34 (m, 5H), 6.67~6.78 (m, 6H), 3.94~3.97 (d, J=15 Hz, 1H), 3.82~3.86 (m, 4H), 3.69~3.71 (d, J=15 Hz, 1H), 2.98~3.01 (m, 1H), 2.90~2.92 (m, 1H), 2.68~2.83 (m, 7H), 2.11~2.14 (m, 1H), 1.78~1.86 (m, 3H)

HR-MS (ESI) calculated $C_{29}H_{31}O_4F_2N$ (M+H)$^+$: calculated 496.2293, found 496.2287.

Example 16: Preparation of (2R,3R)-3-[2-(benzyloxy)-5-fluorophenethyl]-2-hydroxymethyl-oxacyclopropane (Compound Va, Wherein R is Benzyl)

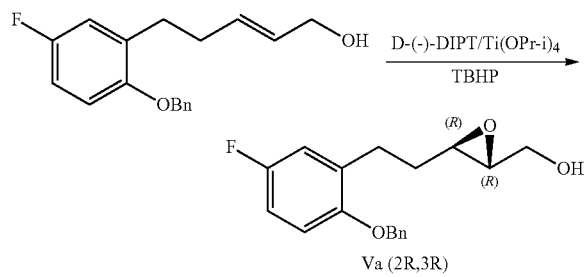

Va (2R,3R)

2 g powdered 4 Å molecular sieve in 25 ml anhydrous methylene dichloride was cooled to −25° C., to which 1.85 g D-(−)-DIPT (7.9 mmol) and 2.06 g (7.2 mmol) Ti(OPr-i)$_4$ were added sequentially. After the addition was completed, the mixture was stirred at −25° C. for 20 min, to which 6.7 ml 3.2 N TBHP (19.8 mmol) (a solution in toluene) was then added dropwise. After the addition was completed, the mixture was stirred at −25° C. for 20 min, to which a solution of 1.89 g (6.6 mmol) compound IV1 (wherein R is benzyl) in 20 ml methylene dichloride was then added dropwise (within about 15 min). After the addition was completed, the reaction mixture was stirred at −25 to −22° C. for 6 h (until the spot of starting material disappeared).

Work-up: the reaction mixture was poured into a fresh solution of FeSO$_4$/tartaric acid/H$_2$O (2.5 g FeSO$_4$+1.0 g tartaric acid+20 ml H$_2$O). The resulting mixture was stirred at room temperature for 1 h, and filtered with Celite. Organic layer was separated from the filtrate, and water layer was extracted with methylene dichloride twice. The extract solutions were combined, washed with water, dried with anhydrous Na$_2$SO$_4$, and evaporated under reduced pressure to dryness, yielding 4.0 g oil.

The oil was dissolved in 40 ml DCM, to which 20 ml of the solution of 30% NaOH in saturated NaCl solution was added dropwise with cooling in ice bath. After the addition was completed, the reaction mixture was stirred at room temperature for 1 h. Organic layer was separated, and water layer was extracted with DCM twice. The extract solutions were combined, washed with water, dried with anhydrous Na$_2$SO$_4$. The mixture was filtered and the resulting filtrate was evaporated to dryness. The residue was loaded on silica gel column and eluted with PL/EtOAc (3/1), to obtain 1.54 g colorless oil.

$^1$H-NMR (400 MHz, CDCl$_3$) δ 7.32~7.41 (m, 5H), 6.88~6.90 (d, J=8.4 Hz, 1H), 6.83~6.85 (m, 2H), 5.04 (s, 2H), 3.80~3.83 (d, J=12.5 Hz, 1H), 3.51~3.57 (m, 1H), 2.97~2.99 (t, J=5.6 Hz, 1H), 2.75~2.85 (m, 3H), 1.84~1.91 (m, 2H).

HR-MS (ESI) calculated C$_{18}$H$_{19}$O$_3$FNa (M+Na)$^+$: 325.1210, found 325.1201.

$[α]_D^{20}$; +22.9 (CHCl$_3$, C 1.0).

Example 17: Preparation of (2S,3S)-3-[2-(benzyloxy)-5-fluorophenethyl]-2-hydroxymethyl-oxacyclopropane (Compound Vb, Wherein R is Benzyl)

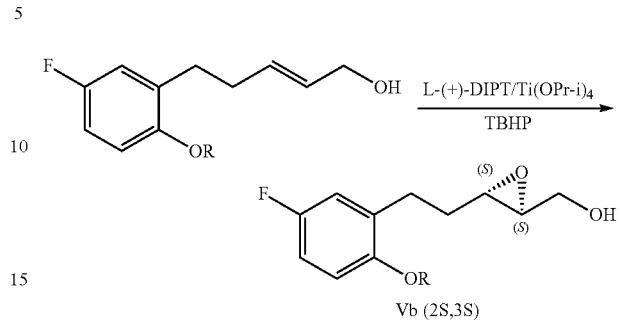

Vb (2S,3S)

According to the method similar to Example 16, compound IV1 was used as starting material and L-(+)-diisopropyl tartrate was used as chiral inducer, to obtain compound Vb.

$[α]_D^{20}$; −23.1 (CHCl$_3$, C 1.0)

Example 18: Preparation of (2R,3S)-3-[2-(benzyloxy)-5-fluorophenethyl]-2-hydroxymethyl-oxacyclopropane (Compound VIa, Wherein R is Benzyl)

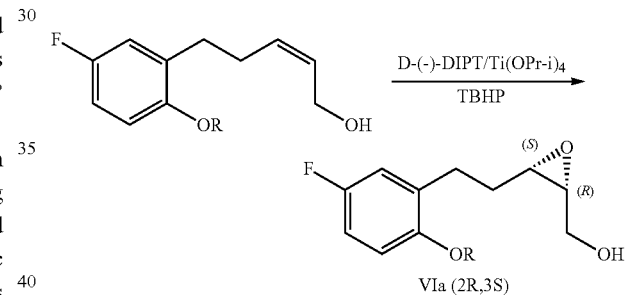

VIa (2R,3S)

2 g powdered 4 Å molecular sieve in 25 ml anhydrous methylene dichloride was cooled to −25° C., to which 1.85 g D-(−)-DIPT (7.9 mmol) and 2.06 g (7.2 mmol) Ti(OPr-i)$_4$ were added sequentially. After the addition was completed, the mixture was stirred at −25° C. for 20 min, to which 6.7 ml 3.2 N TBHP (19.8 mmol) (a solution in toluene) was then added dropwise. After the addition was completed, the mixture was stirred at −25° C. for 20 min, to which a solution of 1.92 g (6.7 mmol) compound IV2 (wherein R is benzyl) in 20 ml methylene dichloride was then added dropwise (within about 15 min). After the addition was completed, the reaction mixture was stirred at −25 to −22° C. for 6 h. The reaction mixture was poured into a fresh solution of FeSO$_4$/tartaric acid/H$_2$O (2.5 g FeSO$_4$+1.0 g tartaric acid+20 ml H$_2$O). The resulting mixture was stirred at room temperature for 1 h, and filtered with Celite. Organic layer was separated from the filtrate, and water layer was extracted with methylene dichloride twice. The extract solutions were combined, washed with water, dried with anhydrous Na$_2$SO$_4$, and evaporated under reduced pressure to dryness, yielding oil.

The oil was dissolved in 40 ml Et$_2$O, to which 20 ml of the solution of 30% NaOH in saturated NaCl solution was added dropwise with cooling in ice bath. After the addition was completed, the reaction mixture was stirred at room temperature for 1 h. Organic layer was separated, and water layer was extracted with DCM twice. The extract solutions were combined, washed with water, dried with anhydrous $Na_2SO_4$. The mixture was filtered and the resulting filtrate was evaporated to dryness. The residue was loaded on silica gel column and eluted with PL/EtOAc (3/1), to obtain 1.63 g colorless oil.

$^1$H-NMR (400 MHz, $CDCl_3$) δ 7.34~7.41 (m, 5H), 6.88~6.90 (d, J=8.4 Hz, 1H), 6.84~6.86 (m, 2H), 5.03 (s, 2H), 3.48~3.56 (m, 2H), 3.03~3.09 (m, 2H), 2.71~2.87 (m, 2H), 1.89~1.96 (m, 1H), 1.75~1.83 (m, 1H).

$[α]_D^{20}$; −1.5 ($CHCl_3$, c 1.0)

Example 19: Preparation of (2S,3R)-3-[2-(benzyloxy)-5-fluorophenethyl]-2-hydroxymethyl-oxacyclopropane (Compound VIb, Wherein R is Benzyl)

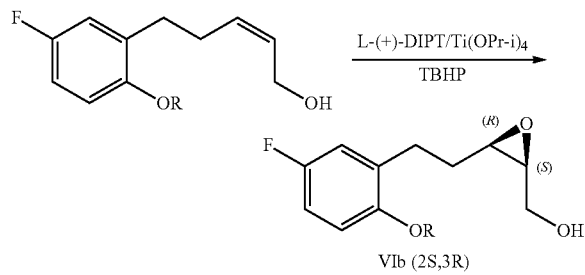

According to the method similar to Example 16, compound IV2 (wherein R is benzyl) was used as starting material and L-(+)-diisopropyl tartrate was used as chiral inducer, to obtain compound VIb.

$[α]_D^{20}$; +1.6 ($CHCl_3$, c 2.0)

Example 20: Preparation of 1-[6-fluoro-(2S)-3,4-dihydro-2H-benzopyran-2-yl]-(1R)-1,2-ethylene glycol (Compound VIIa)

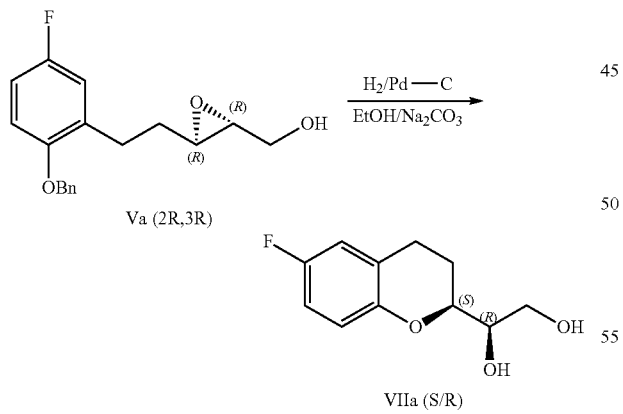

1.09 g compound Va (wherein R is benzyl) was dissolved in 25 ml EtOH, to which 0.25 g 10% Pd—C and 0.075 g anhydrous sodium carbonate was added, and hydrogenation was carried out under ordinary pressure (about 1 h). The hydrogenation was stopped. The reaction mixture was stirred at 60° C. in oil bath for 2 h, and filtered to remove Pd/C. The residue was washed with EtOH. The filtrate was evaporated to dryness, yielding 0.75 g white solid.

$^1$H-NMR (400 MHz, $CDCl_3$) δ 6.70~6.80 (m, 3H), 3.99~4.02 (dd, J=10.4, 3.6 Hz, 1H), 3.82~3.89 (m, 3H), 2.75~2.85 (m, 2H), 2.11~2.16 (m, 1H), 1.82~1.90 (m, 1H)

$[α]_D^{20}$; +89.6 ($CH_3OH$, c 1.0)

Example 21: Preparation of 1-[6-fluoro-(2R)-3,4-dihydro-2H-benzopyran-2-yl]-(1S)-1,2-ethylene glycol (Compound VIIb)

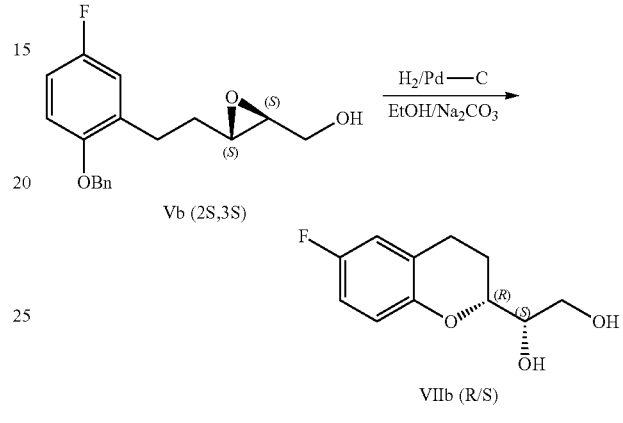

According to the method similar to Example 20, compound Vb (wherein R is benzyl) was used as starting material to obtain compound VIIb.

$[α]_D^{20}$; −87.9 ($CH_3OH$, c 1.0)

Example 22: Preparation of 1-[6-fluoro-(2R)-3,4-dihydro-2H-benzopyran-2-yl]-(1R)-1,2-ethylene glycol (Compound VIIIa)

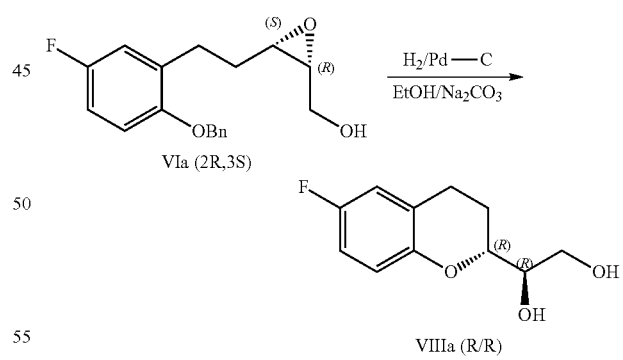

1.3 g compound VIa (wherein R is benzyl) was dissolved in 25 ml EtOH, to which 0.2 g 10% Pd—C and 0.1 g anhydrous sodium carbonate was added. Hydrogenation was carried out under ordinary pressure until no hydrogen was absorbed. The hydrogenation was stopped. The reaction mixture was stirred at 60° C. in oil bath for 2 h, and filtered to remove Pd/C. The residue was washed with EtOH. The filtrate was evaporated to dryness, yielding 0.88 g white solid.

¹H-NMR (400 MHz, CDCl₃) δ 6.73~6.81 (m, 3H), 4.04~4.07 (m, 1H), 3.81~3.85 (m, 2H), 3.76~3.76 (m, 1H) 2.84~2.86 (m, 1H), 2.74~2.79 (m, 1H), 1.78~2.02 (m, 2H), 2.04 (bs, 2H)

$[\alpha]_D^{20}$; −113.1 (CH₃OH, c 1.0), $[\alpha]_D^{20}$; −112.0 (CH₃Cl, c 0.1)

Example 23: Preparation of 1-[6-fluoro-(2S)-3,4-dihydro-2H-benzopyran-2-yl]-(1S)-1,2-ethylene glycol (Compound VIIIb)

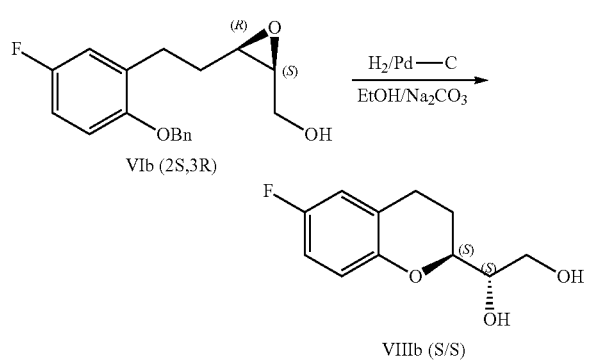

According to the method similar to Example 22, compound VIb (wherein R is benzyl) was used as starting material to obtain compound VIIIb as white solid; $[\alpha]_D^{20}$; +95.6 (CH₃Cl, c 0.045).

Example 24: Preparation of (S,R)-(+)-α-[(p-tolylsulfonyloxy)methyl]-(6-fluoro-2-chromanyl)-methanol (Compound IXa)

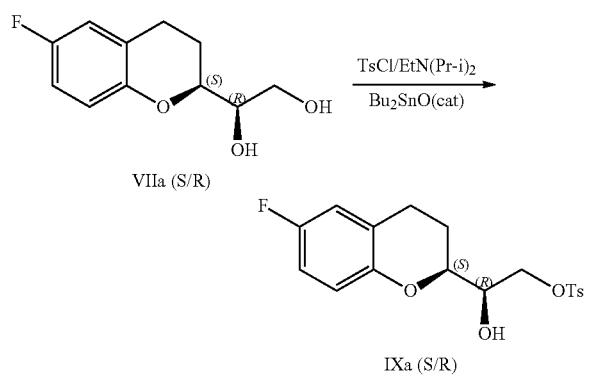

According to the method similar to Example 11, compound VIIa was used as starting material to obtain compound IXa.

¹H-NMR (400 MHz, CDCl₃) δ 7.80~7.82 (d, J=7.6 Hz, 2H), 7.34~7.35 (d, J=7.6 Hz, 2H), 6.7 (s, 2H), 6.58~6.61 (m, 1H), 4.36~4.39 (d, J=10.4 Hz, 1H), 4.21~4.23 (m, 1H), 3.91 (s, 2H), 2.75~2.8 (m, 2H), 2.45 (s, 3H), 2.16~2.19 (m, 1H), 1.75~1.79 (m, 1H)

$[\alpha]_D^{20}$; +82.1 (CHCl₃, c 0.56)

Example 25: Preparation of (R,R)-(−)-α-[(p-tolylsulfonyloxy)methyl]-(6-fluoro-2-chromanyl)-methanol (Compound Xa)

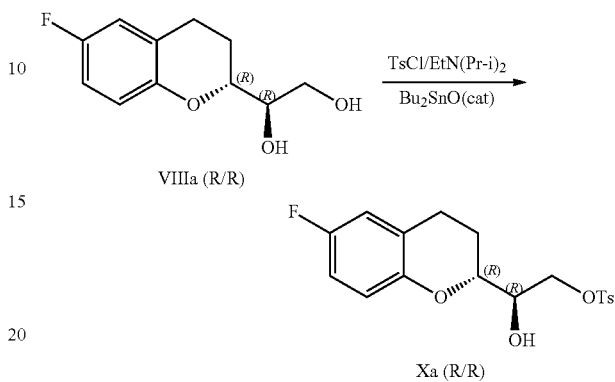

According to the method similar to Example 11, compound VIIIa was used as starting material to obtain compound Xa.

¹H-NMR (400 MHz, CDCl₃) δ 7.80~7.82 (d, J=8.0 Hz, 2H), 7.33~7.35 (d, J=8.0 Hz, 2H), 6.73~6.79 (m, 2H), 6.64~6.67 (m, 1H), 4.21~4.22 (d, J=5.6 Hz, 2H), 4.0~4.02 (m, 1H), 3.91~3.95 (m, 1H), 2.72~2.87 (m, 2H), 2.44 (s, 3H), 1.93~1.95 (m, 2H)

HR-MS (ESI) calculated C₁₈H₁₉O₅FNaS(M+Na)⁺: calculated 389.0829, found 389.0823.

$[\alpha]_D^{20}$; −48.4 (CH₃Cl, c 0.68)

Example 26: Preparation of (R,S)-(−)-α-[(p-tolylsulfonyloxy)methyl]-(6-fluoro-2-chromanyl)-methanol (Compound IXb)

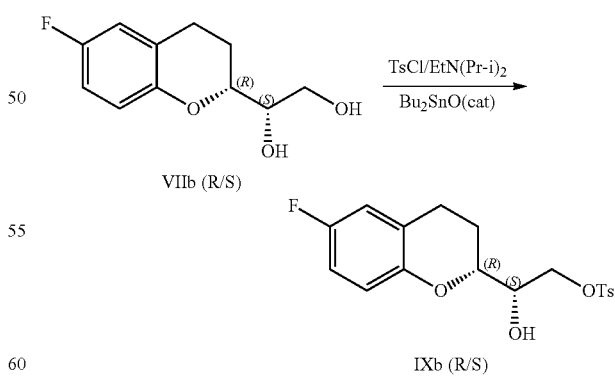

According to the method similar to Example 11, compound VIIb was used as starting material to obtain compound IXb.

$[\alpha]_D^{20}$; −80.3 (CHCl₃, c 0.85)

Example 27: Preparation of (S,S)-(+)-α-[(p-tolylsulfonyloxy)methyl]-(6-fluoro-2-chromanyl)-methanol (Compound Xb)

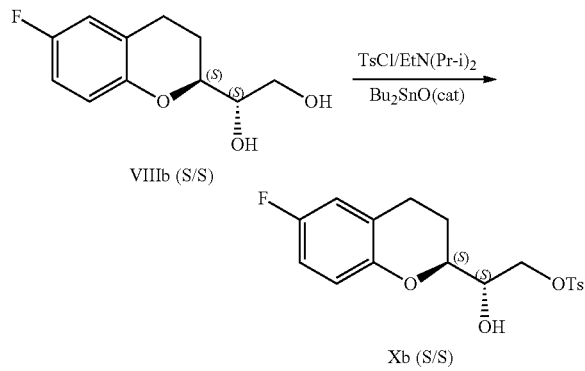

According to the method similar to Example 11, compound VIIIb was used as starting material to obtain compound Xb.

$[\alpha]_D^{20}$; +50.3 (CH$_3$Cl, c 0.50)

Example 28: Preparation of (S,R)-[(benzylamino)methyl]-(6-fluoro-2-chromanyl)-methanol (Compound XIa)

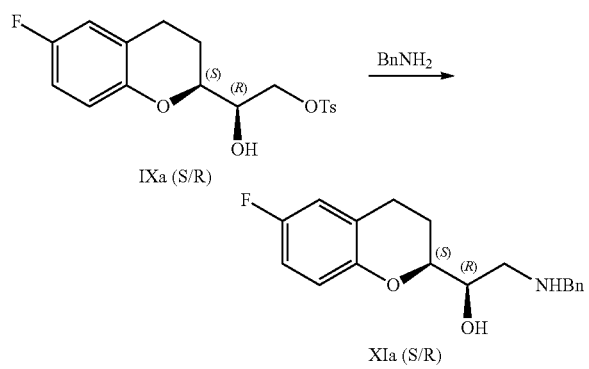

According to the method similar to Example 13, compound IXa was used as starting material to obtain compound XIa.

Compound XIa is a white solid, $[\alpha]_D^{20}$; +82.1 (CHCl$_3$, c 0.56)

Example 29: Preparation of (R,S)-[(benzylamino)methyl]-(6-fluoro-2-chromanyl)-methanol compound XIb)

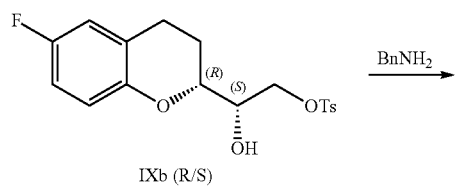

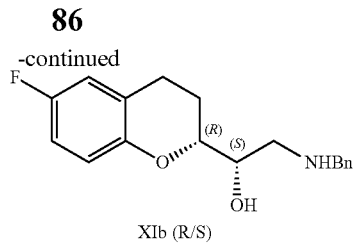

According to the method similar to Example 13, compound IXb was used as starting material to obtain compound XIb.

$[\alpha]_D^{20}$; −79.3 (CHCl$_3$, c 0.45)

Example 30: Preparation of N-benzyl-D-Nebivolol (Compound XIIIa)

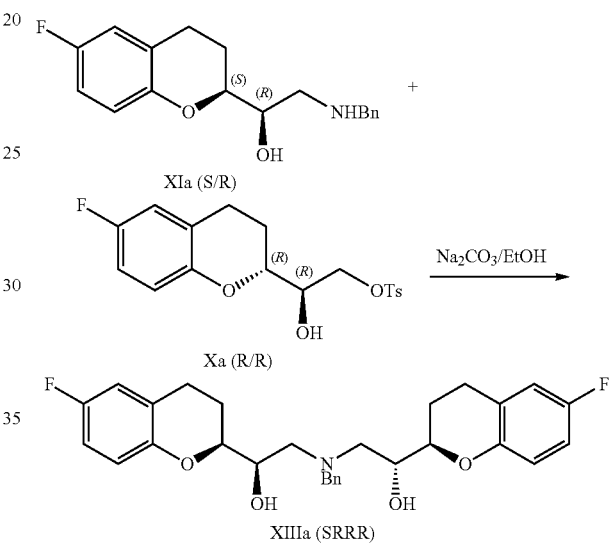

287 mg (0.95 mmol) compound XIa and 350 mg (0.95 mmol) compound Xa was dissolved in 5 ml ethanol, to which 150 mg anhydrous Na$_2$CO$_3$ was added. The reaction mixture was heated under reflux with stirring for 16 h.

The reaction mixture was evaporated under reduced pressure to dryness. 10 ml water was added to the residue, and the resulting mixture was extracted with EtOAc twice. The extract solutions were combined, washed with saturated NaCl solution, dried with anhydrous Na$_2$SO$_4$. After filtration, the filtrate was evaporated under reduced pressure to dryness, and 453 mg product was obtained as syrup, which was then recrystallized from ethanol/water, yielding 373 mg white solid (79%).

Example 30': Preparation of N-benzyl-D-Nebivolol hydrochloride (Compound XIIIa Hydrochloride)

287 mg (0.95 mmol) compound XIa and 350 mg (0.95 mmol) compound Xa was dissolved in 5 ml ethanol, to which 150 mg anhydrous Na$_2$CO$_3$ was added. The reaction mixture was heated under reflux with stirring for 16 h.

The reaction mixture was evaporated under reduced pressure to dryness. 10 ml water was added to the residue, and the resulting mixture was extracted with EtOAc twice. The extract solutions were combined, to which 2 ml 1 N hydrochloric acid was added. The resulting mixture was stirred and crystal precipitated. After filtration, 390 mg white solid with purity of 99.5% was obtained.

Example 30": Preparation of N-benzyl-D-Nebivolol (Compound XIIIa)

390 mg compound XIIIa hydrochloride was added to 10 ml methylene dichloride. The resulting mixture was stirred, and was neutralized by adding aqueous sodium bicarbonate solution. Different layers appeared. Organic layer was dried and concentrated to give 355 mg white solid with purity of 99.7%.

Example 31: Preparation of N-benzyl-L-Nebivolol (Compound XIIIb)

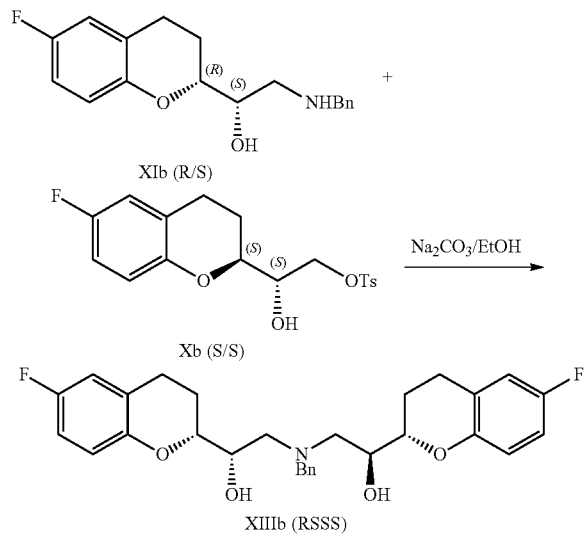

According to the method similar to Example 30, compounds XIb and Xb were used as starting materials to obtain compound XIIIb.

Example 31': Preparation of N-benzyl-L-Nebivolol hydrochloride (Compound XIIIb Hydrochloride)

According to the method similar to Example 30', compounds XIb and Xb were used as starting materials to obtain compound XIIIb hydrochloride with purity of 99.6%.

Example 31": Preparation of N-benzyl-L-Nebivolol (Compound XIIIb)

According to the method similar to Example 30", compound XIIIb was obtained with purity of 99.8%.

Example 32: Preparation of DL-Nebivolol (Compound I) Hydrochloride 200 mg (0.4 mmol) compound I was dissolved in 5 ml ethanol, to which 50 mg 10% Pd—C was added. Hydrogenation was carried out under ordinary pressure at room temperature for 18 hours. After filtration, the residue was washed with ethanol. Hydrogen chloride gas was introduced into the filtrate. Then the solution was evaporated under reduced pressure to remove ethanol, and white solid was obtained, to which anhydrous diethyl ether was added. The resulting mixture was stirred and filtered, yielding 160 mg product (89%).

$^1$H-NMR (500 MHz, DMSO-$d_6$) δ 8.81 (bs, 2H), 6.90~6.94 (m, 4H), 6.75~6.76 (dd, 2H), 5.99 (bs, 1H), 5.80 (bs, 1H), 4.11 (m, 1H), 3.98~4.02 (m, 2H), 3.89~3.91 (m, 1H), 3.17~3.22 (m, 2H), 3.05~3.07 (m, 1H), 2.74~2.82 (m, 4H), 2.10~2.13 (m, 1H), 1.92~1.94 (m, 1H), 1.75~1.80 (m, 1H), 1.67~1.71 (m, 1H)

HR-MS (FAB$^+$) calculated $C_{22}H_{26}F_2NO_4S$ (M+1-HCl)$^+$: calculated 406.1829, found 406.1825.

Example 32': Preparation of DL-Nebivolol (Compound I) Hydrochloride 100 mg compound XIIIa' and 100 mg compound XIIIb' was added to 15 ml methylene dichloride. The resulting solution was neutralized by adding aqueous sodium bicarbonate solution. Different layers appeared. Organic layer was concentrated to dryness. 50 ml methanol and 50 mg 10% Pd—C were added to the residue. Hydrogenation was carried out under ordinary pressure at room temperature for 18 hours. After filtration, the residue was washed with methanol. 2 ml 1 N hydrochloric acid was added to the filtrate. Crystal precipitated. The mixture was filtered. The resulting solid was washed and dried to give 100 mg white solid with purity of 99.9%.

$^1$H-NMR (500 MHz, DMSO-$d_6$) δ 8.81 (bs, 2H), 6.90~6.94 (m, 4H), 6.75~6.76 (dd, 2H), 5.99 (bs, 1H), 5.80 (bs, 1H), 4.11 (m, 1H), 3.98~4.02 (m, 2H), 3.89~3.91 (m, 1H), 3.17~3.22 (m, 2H), 3.05~3.07 (m, 1H), 2.74~2.82 (m, 4H), 2.10~2.13 (m, 1H), 1.92~1.94 (m, 1H), 1.75~1.80 (m, 1H), 1.67~1.71 (m, 1H)

HR-MS (FAB$^+$) calculated $C_{22}H_{26}F_2NO_4S$(M+1-HCl)$^+$: calculated 406.1829, found 406.1825.

Example 32": Preparation of DL-Nebivolol (Compound I) Hydrochloride 100 mg compound XIIIa obtained according to Example 30" and 100 mg compound XIIIb obtained according to Example 31" were added to 50 ml methanol, to which 50 mg 10% Pd—C was added. Hydrogenation was carried out under ordinary pressure at room temperature for 18 hours. After filtration, the residue was washed with methanol. 2 ml 1 N hydrochloric acid was added to the filtrate. Crystal precipitated. The mixture was filtered. The resulting solid was washed and dried to give 105 mg white solid with purity of 99.9%.

$^1$H-NMR (500 MHz, DMSO-$d_6$) δ 8.81 (bs, 2H), 6.90~6.94 (m, 4H), 6.75~6.76 (dd, 2H), 5.99 (bs, 1H), 5.80 (bs, 1H), 4.11 (m, 1H), 3.98~4.02 (m, 2H), 3.89~3.91 (m, 1H), 3.17~3.22 (m, 2H), 3.05~3.07 (m, 1H), 2.74~2.82 (m, 4H), 2.10~2.13 (m, 1H), 1.92~1.94 (m, 1H), 1.75~1.80 (m, 1H), 1.67~1.71 (m, 1H)

HR-MS (FAB$^+$) calculated $C_{22}H_{26}F_2NO_4S$ (M+1-HCl)$^+$: calculated 406.1829, found 406.1825.

Example 33a: Preparation of D-Nebivolol (Compound Ia) Hydrochloride

According to the method similar to Example 32, compound XIIIa was used as starting material to obtain compound Ia as hydrochloride. $[α]_D^{20}$: +22.0 (CH$_3$OH, C 0.5)

Example 33b: Preparation of L-Nebivolol (Compound Ib) Hydrochloride

According to the method similar to Example 32, compound XIIIb was used as starting material to obtain compound Ib as hydrochloride. $[\alpha]_D^{20}$; −21.2 (CH$_3$OH, C 0.4).

In view of the above, the novel processes provided by the present invention have high stereoselectivity, the preparation of the key intermediates can avoid separation with the column chromatography, and the reaction conditions are mild and do not require special reagents. Compared with the prior art, the processes for preparation of Nebivolol according to the present invention have greatly reduced cost and are very suitable for industrial production. Especially the purification by crystallization of intermediate compounds of formulae III, IV1 and IV2 greatly improves the quality of intermediate compounds and products, resulting in that the quality of products is controllable, the yield is improved and the production cost is remarkably reduced. Moreover, the compounds of formulae XIIIa and XIIIb are purified by formation of salt and crystallization, which greatly improves the product quality and enables the purity of the final product can be 99.9% or more.

While some embodiments and specific examples of the present invention are provided herein, it will be understood by those skilled in the art that these embodiments and examples are merely illustrative examples of the present invention and that other modifications and changes can be made without departing from the spirit of the present invention.

The invention claimed is:

1. A process for the preparation of the compound of formula IV1,

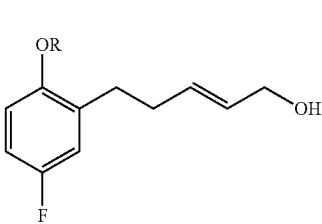
IV1 wherein R is a hydroxy-protecting group, which is selected from an aralkyl, alkoxyalkyl, allyl or silyl protecting group,
the process comprising the following steps:
reducing the compound of formula III with a metal hydride to give the compound of formula IV1,

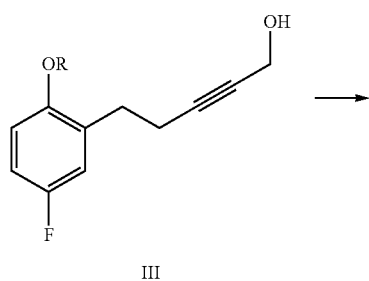
III

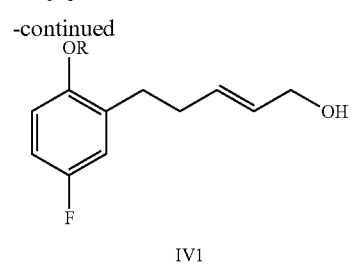
IV1 wherein R is defined as above;
and optionally the following step: to the resulting compound of formula IV1, adding a non-polar organic solvent and stirring at a temperature of 0° C. to −20° C., followed by crystallization and filtration, to yield the compound of formula IV1 as a solid.

2. A process for the preparation of the compound of formula IV2,

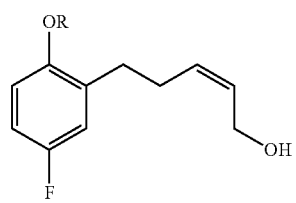
IV2 wherein R is a hydroxy-protecting group, which is selected from an aralkyl, alkoxyalkyl, allyl or silyl protecting group,
the process comprising the following steps:
reducing the compound of formula III via selective catalytic hydrogenation to give the compound of formula IV2 in cis-configuration,

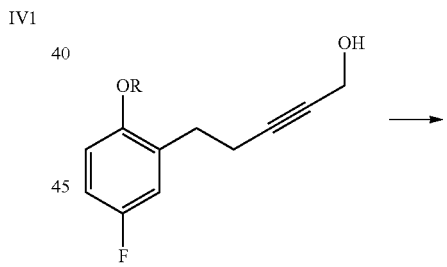
III

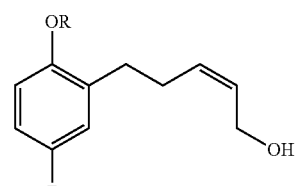
IV2 wherein R is defined as above;
and the following step: to the resulting compound of formula IV2, adding a non-polar organic solvent, and stirring at a temperature of 0° C. to −20° C., followed by crystallization and filtration, to yield the compound of formula IV2 as a solid.

3. A process for the preparation of racemic Nebivolol of formula I,

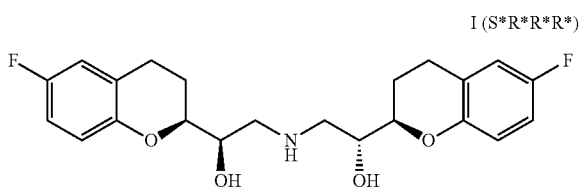 [SMILES: O[C@H](CNC[C@@H](O)[C@H]1CCc2cc(F)ccc2O1)[C@@H]1CCc2cc(F)ccc2O1]

wherein I (S*R*R*R*) represents racemate, which is a racemic mixture consisting of equimolar amounts of D-Nebivolol Ia (SRRR) and the enantiomer thereof L-Nebivolol Ib (RSSS) having the following configurations;

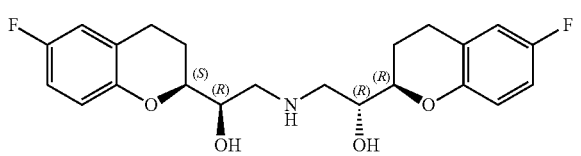

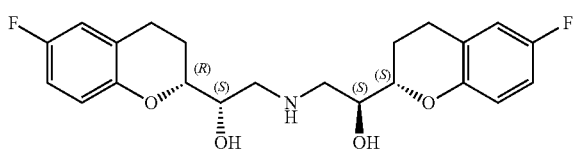

the process comprising the following steps:
1) reducing the compound of formula III with a metal composite hydride to give the compound of formula IV1 in trans-configuration, and optionally the following step: to the resulting compound of formula IV1, adding a non-polar organic solvent, and stirring at a temperature of 0° C. to −20° C., followed by crystallization and filtration, to yield the compound of formula IV1 as a solid,

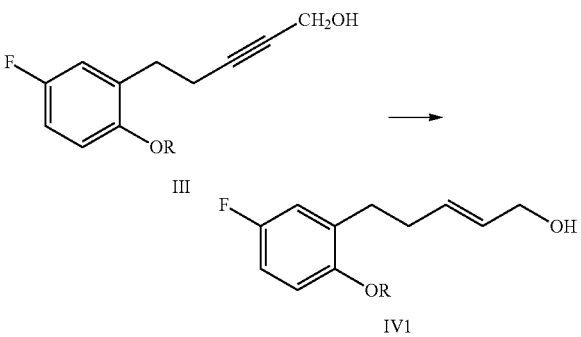

wherein R is a hydroxy-protecting group selected from an alkyl, haloalkyl, aralkyl, alkoxyalkyl, allyl, or silyl protecting group,
2) reducing the compound of formula III via selective catalytic hydrogenation to give the compound of formula IV2 in cis-configuration, and optionally the following step: to the resulting compound of formula IV2, adding a non-polar organic solvent, and stirring at a temperature of 0° C. to −20° C., followed by crystallization and filtration, to yield the compound of formula IV2 as a solid,

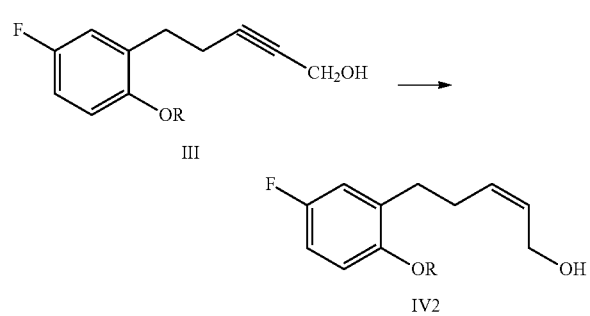

wherein R is defined as above 1), 3) epoxidation of the compound of formula IV1 in trans-configuration and the compound of formula IV2 in cis-configuration in the presence of an epoxidating reagent to give epoxide intermediates V and VI, respectively, wherein R is defined as above,

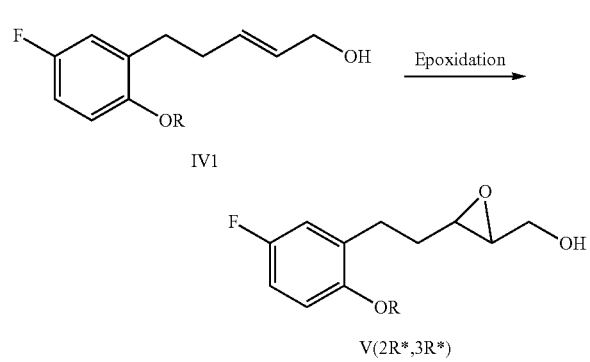

wherein the compound V is racemate, which is a racemic mixture consisting of equimolar amounts of the compound of formula Va and the enantiomer Vb, the relative configuration of which is represented as V (2R*,3R*)

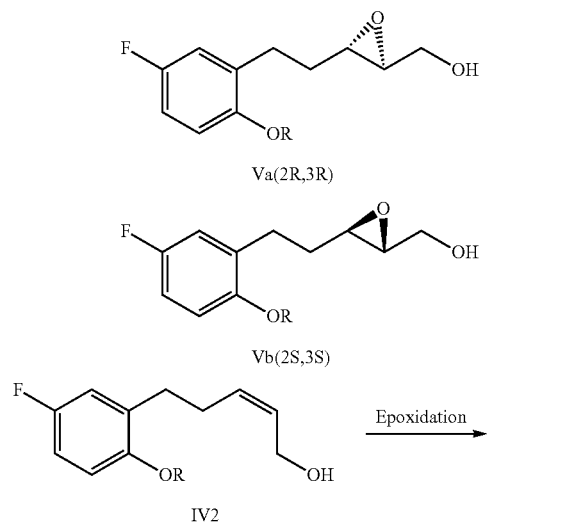

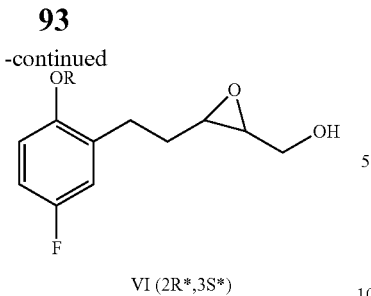

VI (2R*,3S*)

wherein the compound VI is racemate, which is a racemic mixture consisting of equimolar amounts of the compound of formula VIa and the enantiomer VIb, the relative configuration of which is represented as VI (2R*,3S*)

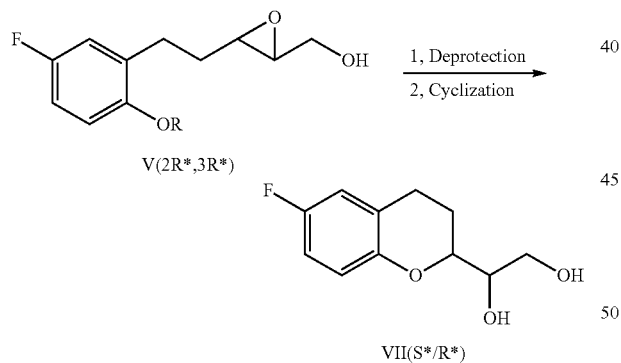

VIa(2R,3S)

VIb(2S,3R)

4) deprotecting the compound of formula V and the compound of formula VI, followed by a cyclization reaction, to give the intermediate compounds of formula VII (S*/R*) and formula VIII (R*/R*), respectively, wherein R is defined as above,

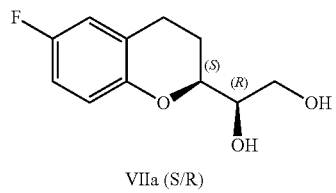

V(2R*,3R*)

1, Deprotection
2, Cyclization

VII(S*/R*)

wherein VII (S*/R*) is racemate, which is a racemic mixture consisting of equimolar amounts of the compound of formula VIIa (S/R) and the enantiomer VIIb (R/S), VIIa (S/R)

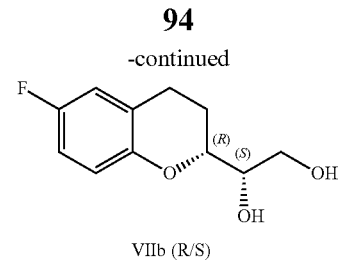

VIIb (R/S)

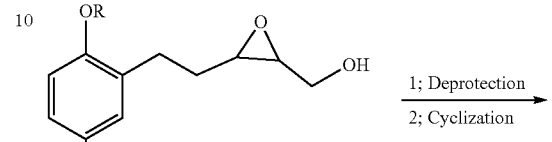

VI (2R*,3S*)

1; Deprotection
2; Cyclization

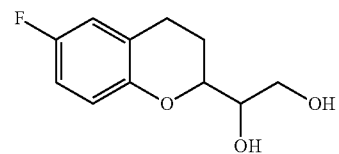

VII (R*/R*)

wherein VIII (R*/R*) is racemate, which is a racemic mixture consisting of equimolar amounts of the compound of formula VIIIa (R/R) and the enantiomer VIIIb (S/S),

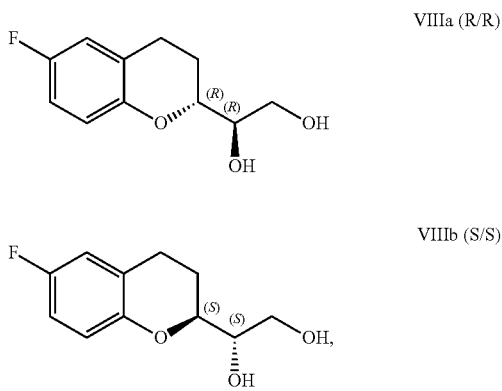

VIIIa (R/R)

VIIIb (S/S)

5) sulfonylating the compounds of formula VII and formula VIII with a sulfonyl halide of the formula M-SO$_2$X (wherein M is alkyl or substituted or unsubstituted aryl, X is halogen) in the presence of a catalyst and a base, to give the compounds IX (S*/R*) and X (R*/R*), respectively,

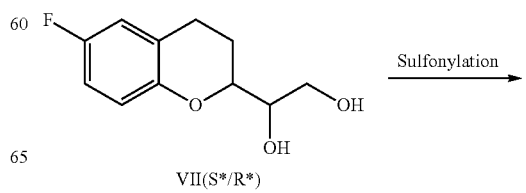

VII(S*/R*)

Sulfonylation

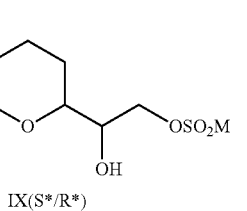

IX(S*/R*)

wherein IX (S*/R*) is racemate, which is a racemic mixture consisting of equimolar amounts of the compound of formula IXa (S/R) and the enantiomer IXb (R/S),

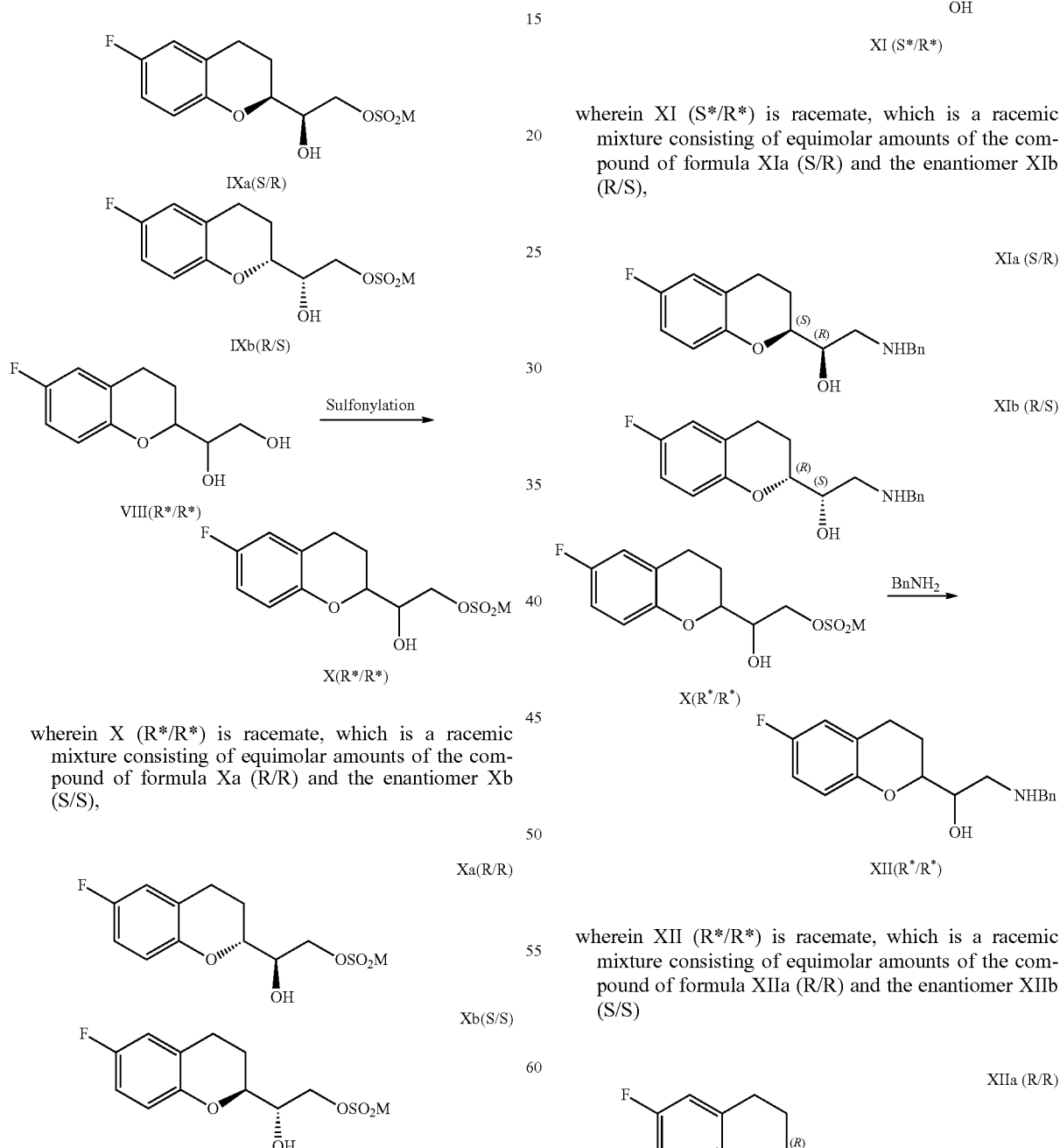

wherein X (R*/R*) is racemate, which is a racemic mixture consisting of equimolar amounts of the compound of formula Xa (R/R) and the enantiomer Xb (S/S), 6) reacting the compound of formula IX or X with benzyl amine to perform an alkylation of the benzyl amine, to give the corresponding compound XI or XII;

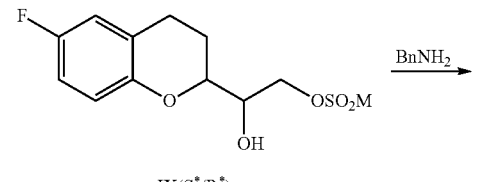

wherein XI (S*/R*) is racemate, which is a racemic mixture consisting of equimolar amounts of the compound of formula XIa (S/R) and the enantiomer XIb (R/S), wherein XII (R*/R*) is racemate, which is a racemic mixture consisting of equimolar amounts of the compound of formula XIIa (R/R) and the enantiomer XIIb (S/S)

-continued

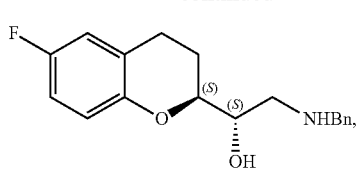

XIIb (S/S)

7) cross-coupling of the intermediate compounds IX (S*/R*) and XII (R*/R*), or cross-coupling of the intermediate compounds X (R*/R*) and XI (S*/R*), under basic conditions, to give the compounds XIII (S*R*R*R*) and XIII' (S*R*S*S*), wherein the definition of R" is the same as the above definition of M,

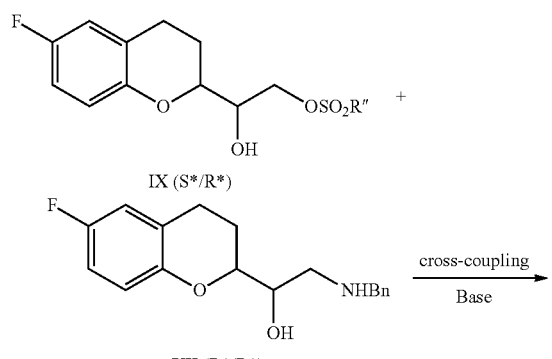

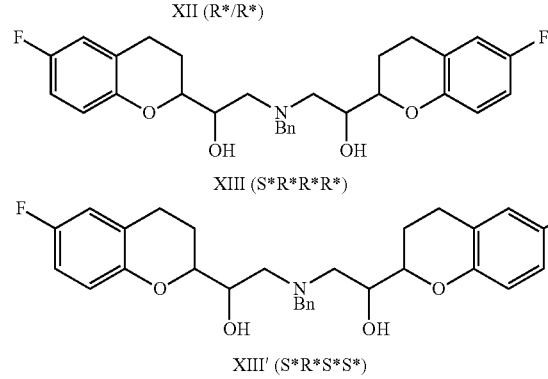

or

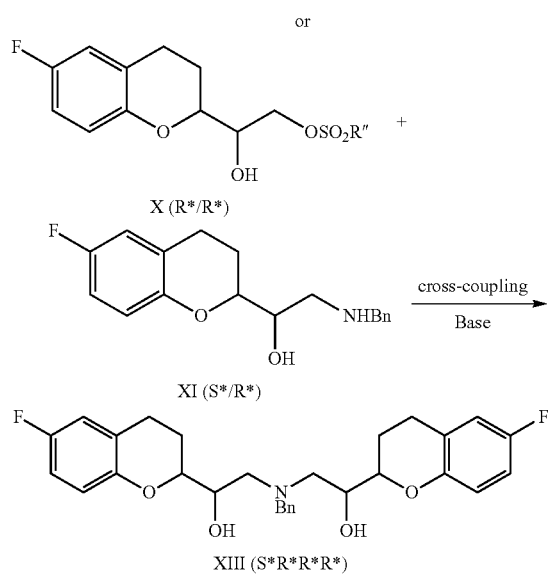

-continued

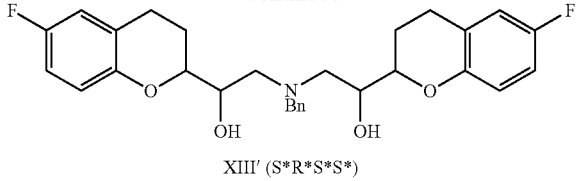

XIII' (S*R*S*S*)

wherein XIII (S*R*R*R*) is racemate, which is a racemic mixture consisting of equimolar amounts of the compound of formula XIIIa (SRRR) and the enantiomer XIIIb (RSSS),

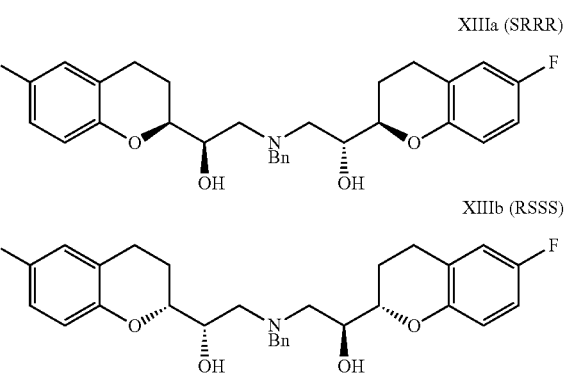

XIII' (S*R*S*S*) is racemate, which is a racemic mixture consisting of equimolar amounts of the compound of formula XIII' a (SRSS) and the enantiomer XIII'b (RSRR), 8) forming salts of the mixture of the compounds of formula XIII and formula XIII', and purifying them by recrystallization to remove the isomer XIII' (S*R*S*S*), to give the intermediate compound XIII (S*R*R*R*), and
9) deprotecting the intermediate compound XIII (S*R*R*R*) to yield the racemic Nebivolol of formula I

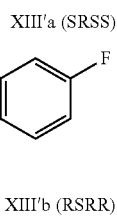 Deprotection →

-continued

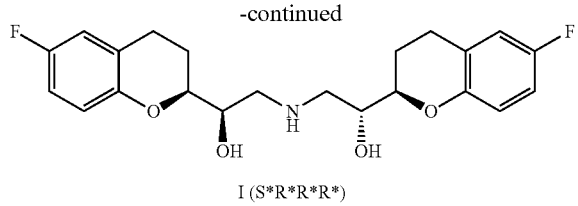

I (S*R*R*R*)

wherein I (S*R*R*R*) is racemate, which is a racemic mixture consisting of equimolar amounts of the compound of formula Ia (SRRR) and the enantiomer Ib (RSSS).

4. A process for the preparation of D-Nebivolol (formula Ia),

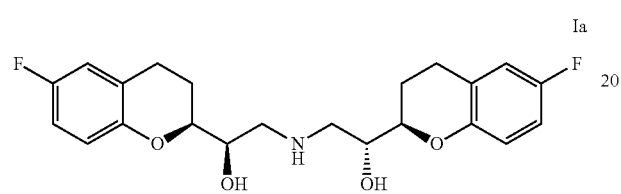

Ia the process comprising the following steps:

a') asymmetric epoxidation of the compound of formula IV1 and the compound of formula IV2 to give intermediate compounds Va and VIa, respectively, wherein R is a hydroxy-protecting group, which is selected from an alkyl, haloalkyl, aralkyl, alkoxyalkyl, allyl, or silyl protecting group;

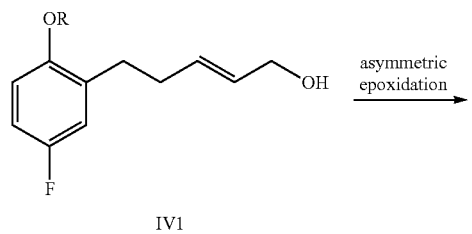

IV1

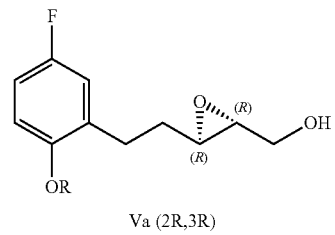

Va (2R,3R)

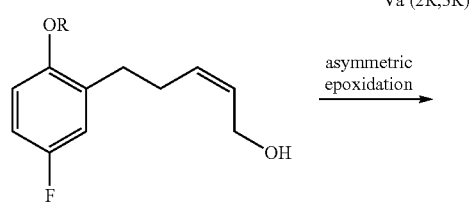

IV2

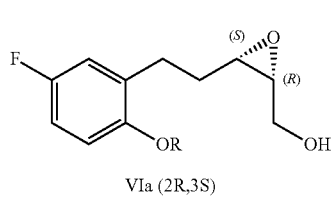

VIa (2R,3S)

b') deprotecting the intermediate compounds Va and VIa, followed by cyclization, to give the intermediate compounds VIIa and VIIIa, respectively, wherein R is defined as above,

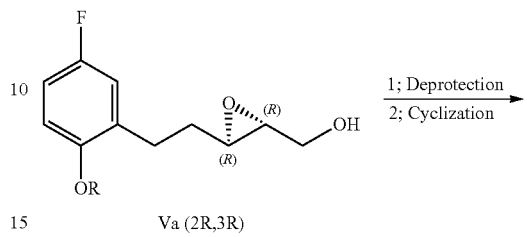

Va (2R,3R)

→ 1; Deprotection
2; Cyclization

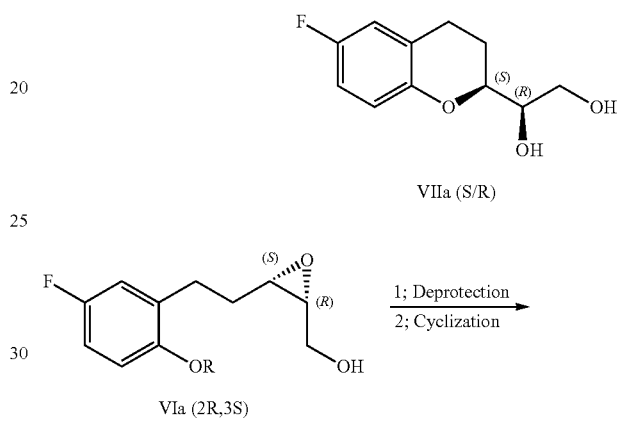

VIIa (S/R)

VIa (2R,3S)

→ 1; Deprotection
2; Cyclization

VIIIa (R/R)

c') sulfonating the intermediate compounds VIIa and VIIIa with a sulfonyl halide of the formula M-SO₂X (wherein M is alkyl or substituted or unsubstituted aryl, X is halogen) in the presence of a catalyst and a base, to give the intermediate compounds IXa and Xa, respectively,

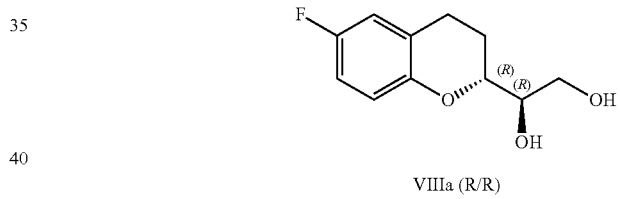

VIIa (S/R)

→ Sulfonylation

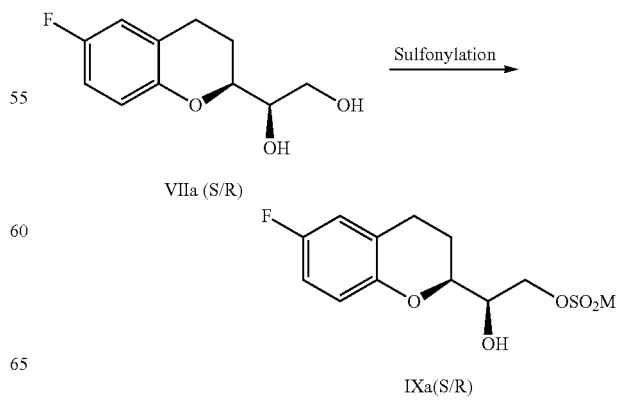

IXa (S/R)

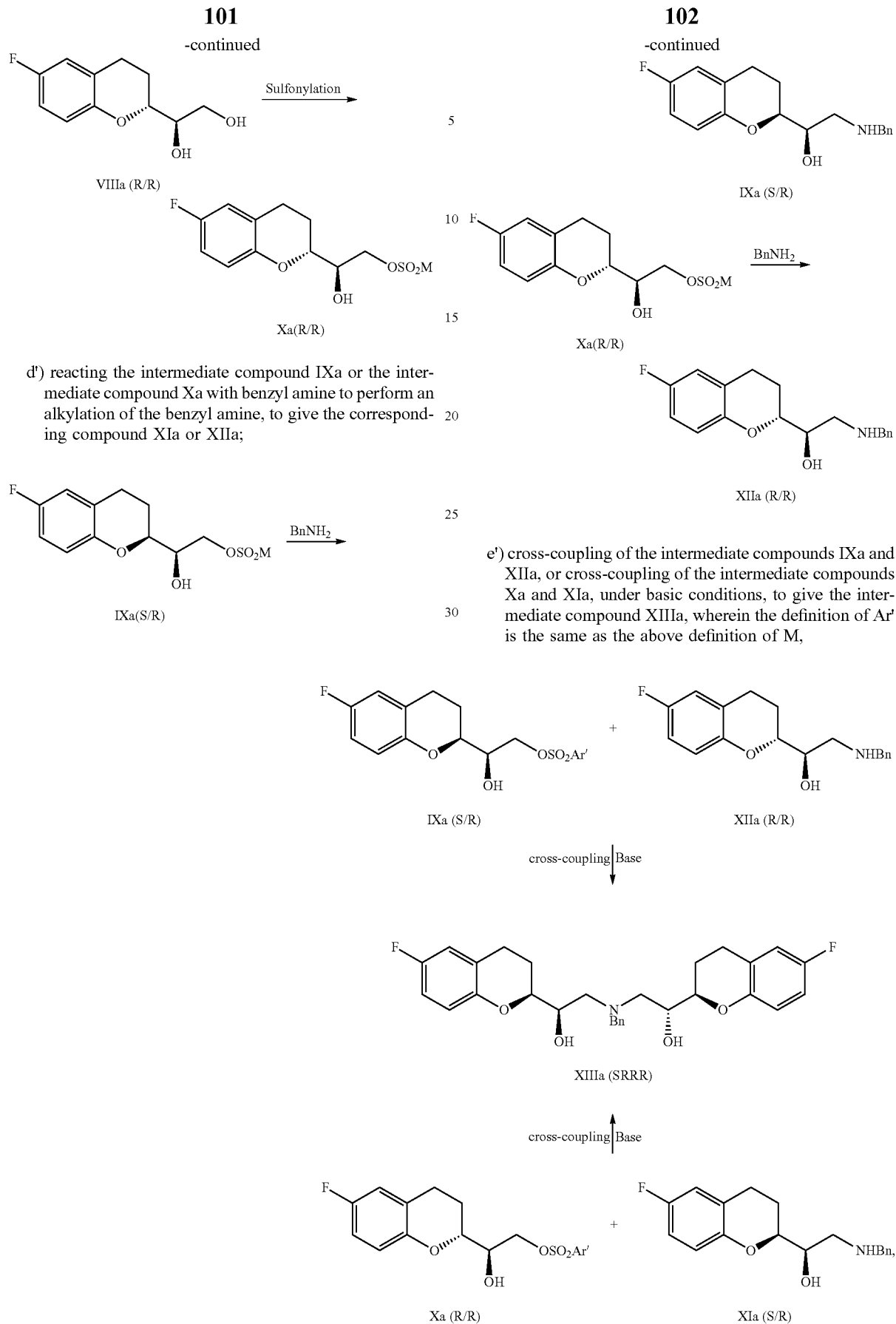

d') reacting the intermediate compound IXa or the intermediate compound Xa with benzyl amine to perform an alkylation of the benzyl amine, to give the corresponding compound XIa or XIIa;

e') cross-coupling of the intermediate compounds IXa and XIIa, or cross-coupling of the intermediate compounds Xa and XIa, under basic conditions, to give the intermediate compound XIIIa, wherein the definition of Ar' is the same as the above definition of M, and optionally converting the intermediate compound XIIIa to the hydrochloride thereof, and f') deprotecting the intermediate compound XIIIa to give D-Nebivolol (formula Ia)

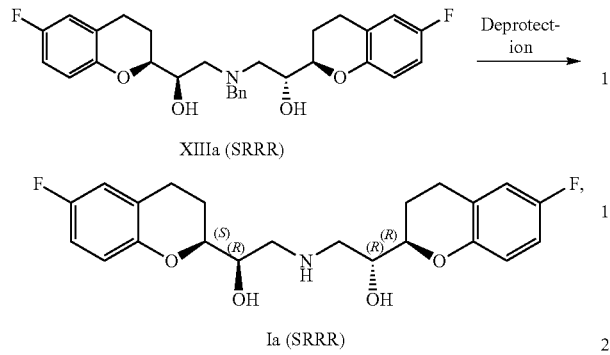

or converting the hydrochloride of the intermediate compound XIIIa to the intermediate compound XIIIa in free form by neutralization with base, followed by deprotection to give D-Nebivolol (formula Ia).

5. A process for the preparation of L-Nebivolol (formula Ib),

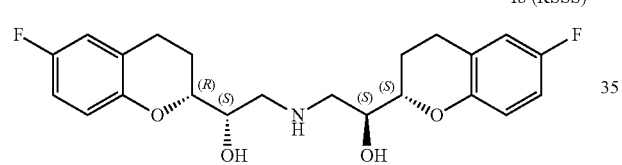

the process comprising the following steps:

a") asymmetric epoxidation of the compound of formula IV1 and the compound of formula IV2 to give intermediate compounds Vb and VIb, respectively, wherein R is a hydroxy-protecting group, which is selected from an alkyl, haloalkyl, aralkyl, alkoxyalkyl, allyl, or silyl protecting group,

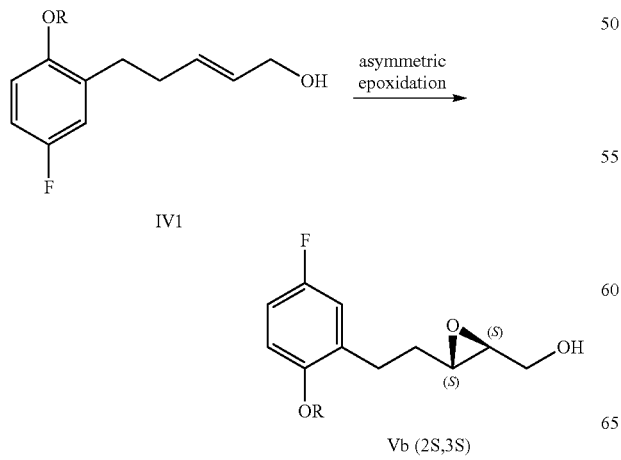

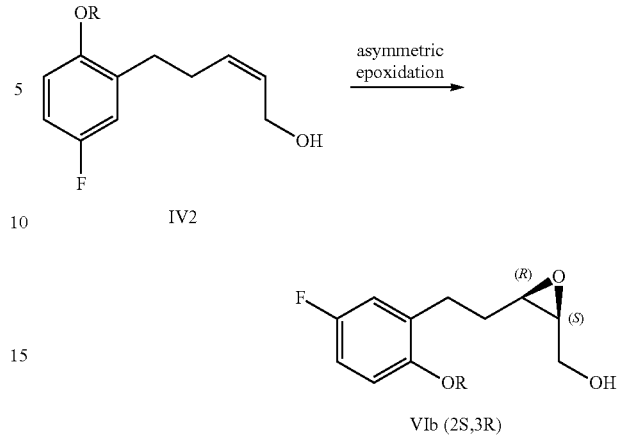

b") deprotecting the intermediate compounds Vb and VIb, followed by cyclization, to give the intermediate compounds VIIb and VIIIb, respectively, wherein R is defined as above,

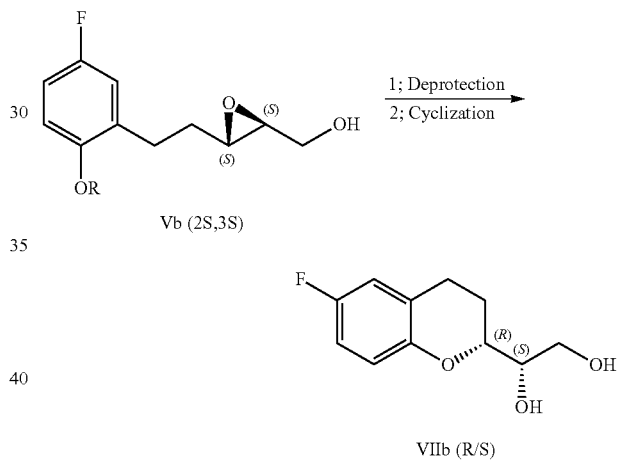

c") sulfonating the intermediate compounds VIIb and VIIIb with a sulfonyl halide of the formula M-SO₂X (wherein M is alkyl or substituted or unsubstituted aryl, X is halogen) in the presence of a catalyst and a base, to give the intermediate compounds IXb and Xb, respectively,

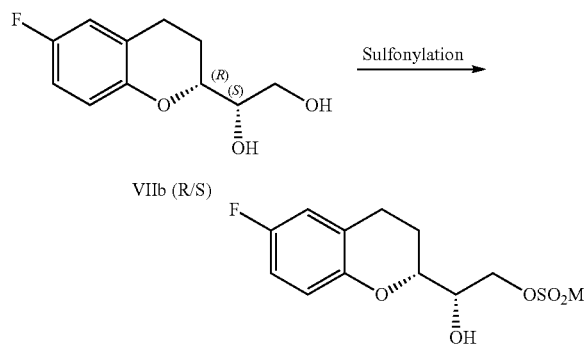
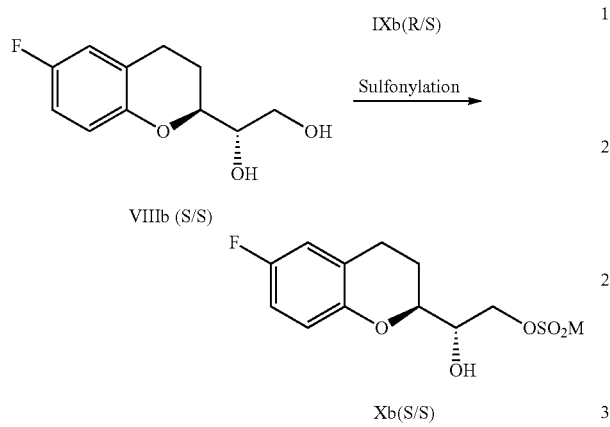

d″) reacting the intermediate compound IXb or the intermediate compound Xb with benzyl amine to perform an alkylation of the benzyl amine, to give the intermediate compound XIb or XIIb

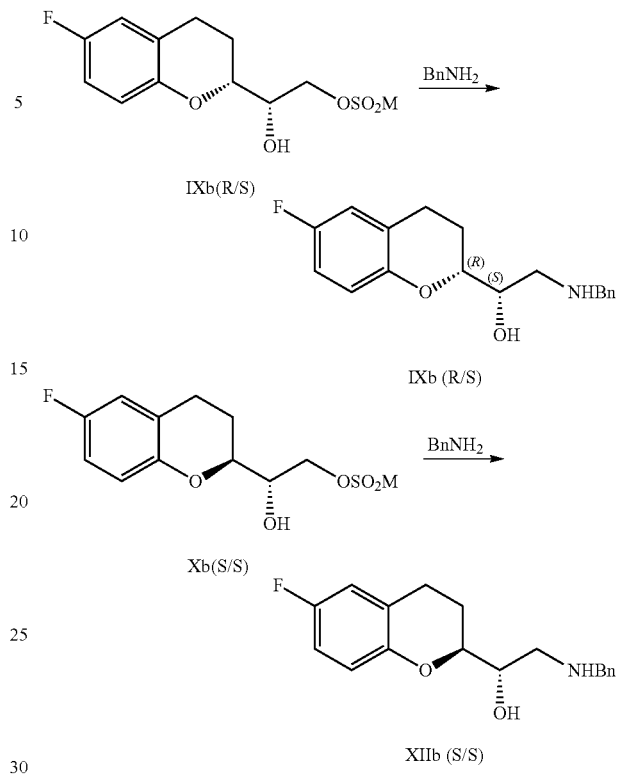

e″) cross-coupling of the intermediate compounds IXb and XIIb, or cross-coupling of the intermediate compounds Xb and XIb, under basic conditions, to give the intermediate compound XIIIb, wherein the definition of Ar' is the same as the above definition of M,

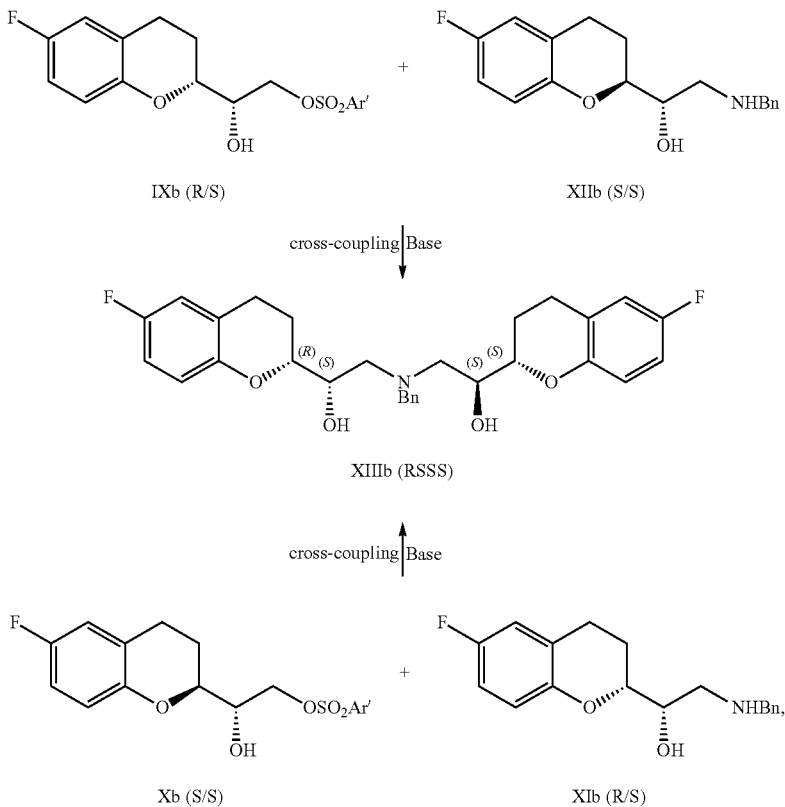

and optionally converting the intermediate compound XIIIb to the hydrochloride thereof, and f'') deprotecting the intermediate compound XIIIb to give L-Nebivolol (formula Ib)

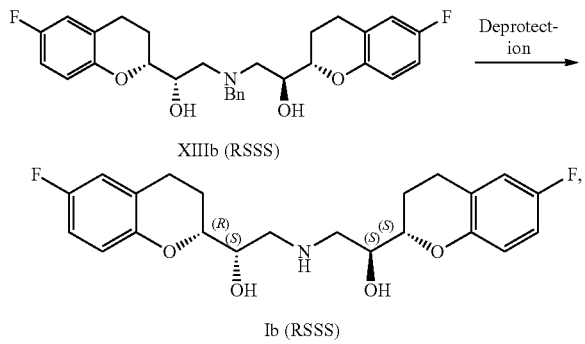

XIIIb (RSSS)

Ib (RSSS)

or converting the hydrochloride of the intermediate compound XIIIb to the intermediate compound XIIIb in free form by neutralization with base, followed by deprotection to give L-Nebivolol (formula Ib).

6. The process according to claim 4, wherein in step a'), Sharpless asymmetric epoxidation is used, and the chiral catalyst used in the reaction is D-(−)-diethyl tartrate or D-(−)-diisopropyl tartrate, the reagent in the reaction is titanium tetraisopropoxide, tert-butyl hydroperoxide or cumene hydroperoxide, the solvent in the reaction is methylene dichloride, and 3 A or 4 A molecular sieve is added into the reaction system.

7. The process according to claim 5, wherein in step a''), Sharpless asymmetric epoxidation is used, and the chiral catalyst used in the reaction is L-(+)-diethyl tartrate or L-(+)-diisopropyl tartrate, the reagent in the reaction is titanium tetraisopropoxide, tert-butyl hydroperoxide or cumene hydroperoxide, the solvent in the reaction is methylene dichloride, and 3 A or 4 A molecular sieve is added into the reaction system.

8. The process according to claim 6, wherein the protecting group R is a benzyl group —CH$_2$Ar, wherein Ar is unsubstituted or substituted aryl, and wherein in step b') the deprotection is carried out by hydrogenolysis in the presence of a catalyst to remove the benzyl protecting group, and cyclization is carried out in the presence of a base, the catalyst used in the hydrogenolysis is a Pd catalyst, and the base used in the cyclization is selected from alkali metal and alkaline earth metal hydroxide or carbonate, alkoxide, or organic heterocyclic base; or wherein the deprotection and the cyclization are carried out by hydrogenolysis using Pd/C as catalyst under basic conditions to simultaneously remove the benzyl protecting group and perform the cyclization, to directly give the cyclization product.

9. The process according to claim 1, wherein the hydroxy-protecting group R is a group selected from t-BuMe$_2$Si, t-BuPh$_2$Si, (i-Pr)$_3$Si, Et$_3$Si, methoxymethyl, benzyl and —CH$_2$Ar, wherein Ar is unsubstituted or substituted aryl; and/or wherein the non-polar organic solvent is selected from n-hexane, n-heptane, petroleum ether, diethyl ether, isopropyl ether or tert-butyl methyl ether, or a mixture of any two or more thereof.

10. The process according to claim 2, wherein the hydroxy-protecting group R is a group selected from t-BuMe$_2$Si, t-BuPh$_2$Si, (i-Pr)$_3$Si, Et$_3$Si, methoxymethyl, benzyl and —CH$_2$Ar, wherein Ar is unsubstituted or substituted aryl; and/or wherein the non-polar organic solvent is selected from n-hexane, n-heptane, petroleum ether, diethyl ether, isopropyl ether or tert-butyl methyl ether, or a mixture of any two or more thereof.

11. The process according to claim 3, wherein the hydroxy-protecting group R is a group selected from t-BuMe$_2$Si, t-BuPh$_2$Si, (i-Pr)$_3$Si, Et$_3$Si, methoxymethyl, benzyl and —CH$_2$Ar, wherein Ar is unsubstituted or substituted aryl; and/or wherein in step 1) and/or in step 2) the non-polar organic solvent is selected from n-hexane, n-heptane, petroleum ether, diethyl ether, isopropyl ether or tert-butyl methyl ether, or a mixture of any two or more thereof.

12. The process according to claim 3, wherein in step 1) the metal composite hydride is selected from LiAlH$_4$ and sodium bis(2-methoxyethoxy)aluminum dihydride, and/or wherein in step 2) the catalyst is selected from Lindlar catalyst and P-2 nickel boride/ethylenediamine catalyst.

13. The process according to claim 3, wherein in step 3) the epoxidating reagent is selected from MCPBA, trifluoroperacetic acid, dimethyldioxirane, a mixture of hydrogen peroxide and acetic acid, a mixture of VO(acac)$_2$ and tert-butyl hydroperoxide, and the system of pyridine-H$_2$O$_2$ in the presence of a catalytic amount of methylrhenium trioxide.

14. The process according to claim 4, wherein the hydroxy-protecting group R is a group selected from t-BuMe$_2$Si, t-BuPh$_2$Si, (i-Pr)$_3$Si, Et$_3$Si, methoxymethyl, benzyl and —CH$_2$Ar, wherein Ar is unsubstituted or substituted aryl.

15. The process according to claim 5, wherein the hydroxy-protecting group R is a group selected from t-BuMe$_2$Si, t-BuPh$_2$Si, (i-Pr)$_3$Si, Et$_3$Si, methoxymethyl, benzyl and —CH$_2$Ar, wherein Ar is unsubstituted or substituted aryl.

16. The process according to claim 8, wherein the Pd catalyst is selected from Pd/C, Pd(OH)$_2$, Pd(OAc)$_2$, PdCl$_2$, and Pd.

* * * * *